(12) United States Patent
Chen et al.

(10) Patent No.: US 8,697,607 B2
(45) Date of Patent: Apr. 15, 2014

(54) GENERATION AND APPLICATION OF STANDARDIZED UNIVERSAL LIBRARIES

(76) Inventors: Tao Chen, London (CA); Te-Ming Chen, Ontario (CA); Jianghan Li, legal representative, Bejing (CN)

(*) Notice: Subject to any disclaimer, the term of this patent is extended or adjusted under 35 U.S.C. 154(b) by 0 days.

(21) Appl. No.: 10/869,055

(22) Filed: Jun. 17, 2004

(65) Prior Publication Data

US 2005/0214782 A1   Sep. 29, 2005

Related U.S. Application Data

(63) Continuation-in-part of application No. PCT/CA02/01941, filed on Dec. 17, 2002.

(60) Provisional application No. 60/340,009, filed on Dec. 17, 2001.

(51) Int. Cl.
  *C40B 50/06* (2006.01)
  *C12Q 1/68* (2006.01)

(52) U.S. Cl.
  USPC .................................. 506/26; 435/6

(58) Field of Classification Search
  USPC .................................. 506/26; 435/6
  See application file for complete search history.

(56) References Cited

U.S. PATENT DOCUMENTS

| | | | |
|---|---|---|---|
| 5,223,409 A * | 6/1993 | Ladner et al. | 435/69.7 |
| 5,498,538 A * | 3/1996 | Kay et al. | 435/69.1 |
| 6,258,530 B1 * | 7/2001 | Huse | 435/6 |
| 6,582,908 B2 * | 6/2003 | Fodor et al. | 506/9 |
| 6,830,902 B1 * | 12/2004 | Astatke et al. | 435/91.1 |

OTHER PUBLICATIONS

U.S. Appl. No. 60/433,460, Tao Chen, Jinghan Li, Te-Ming Chen.
Chen et al., Molecular & Cellular Proteomics 2(9): 826, 2003.
Chen et al., Molecular & Cellular Proteomics 2(9): 868, 2003.
Chen et al., Molecular & Cellular Proteomics 2(9): 998, 2003.
K. Gabriel et al., "A Set of Plasmids Constitutively Producing Different RNA Levels in *Escherichia coli*" J.Mol.Biol. vol. 290: 385-389, 1999.

* cited by examiner

*Primary Examiner* — Amber D. Steele

(57) ABSTRACT

This invention provides quantitative, systematic and standardized High Throughput Screening (HTS) methods capable to the identification of both known and unknown sequences without prior knowledge of the sequences of interest. Either coding or non-coding sequences could be targeted, identified and analyzed systematically and respectively at genomic, transcriptional and translational levels with those methods. The genetic algorithms for sequence deducing and standardized universal libraries constructing are provided. The genetic algorithms are $61^{(n-m)}$, $61^n$, $64^{(n-m)}$, $64^n$, $20^{(n-m)}$ and $20^n$. Applications of the standardized universal libraries include gene expression profiling, signature sequence identification and sequence determination by PCR, cloning, dot-blot hybridization, ELISA, DNA and Peptide Arrays.

4 Claims, No Drawings

GENERATION AND APPLICATION OF STANDARDIZED UNIVERSAL LIBRARIES

PRIOR APPLICATION INFORMATION

Pursuant to 35 U.S.C.s. 119, 120 and 365, this application claims priority to U.S. application Ser. No. 60/340,009 filed on Dec. 17, 2001. This application is a continuation-in-part of international application PCT/CA02/01941 filed on Dec. 17, 2002, which is a continuation of U.S. application Ser. No. 60/340,009 filed on Dec. 17, 2001, all of which are incorporated herein by reference in their entirety.

COPYRIGHT NOTICE

Pursuant to 37 C.F.R. 1.71(e), the applicants notify that a portion of the disclosure of this patent document contains material which is subject to copyright protection. The copyright owner has no objection to the facsimile reproduction of the patent disclosure, as it appears in the Patent and Trademark Office patent file or records, but otherwise reserves all copyright rights whatsoever.

FIELD OF THE INVENTION

The instant invention relates to designs and applications of standardized universal oligonucleotide libraries and the corresponding derivative peptides for High Throughput Screening (HTS) technology platforms. Those standardized HTS technology platforms are capable of performing genome-wide screening, profiling, fingerprinting and cloning processes without prior knowledge of the sequence of a given gene of interest, for example, in clinical diagnosis, therapy development, drug discovery, forensic studies and scientific research.

BACKGROUND OF THE INVENTION

If the completion of Human Genome Project (HGP) is perceived as the scientific landmark of 2003, the creation of DNA microarrays containing a complete set of 50,000 cDNA probes for the entire human genome by Affymetrix Inc. could be regarded as another milestone of the year (Pennisi, Science 302: 211, 2003). However, the current genomic sequence data from humans, *Saccharomyces cerevisiae*, *Caenorhabditis elegans*, *Drosophila melanogaster* and *Escherichia coli* still can not include all the mutations and genetic divergence such as Single Nucleotide Polymorphisms (SNPs).

Additionally, this genome-wide probing system does not have the capacity to detect exogenous genes and their products. Some pathological processes such as infections often involve exogenous genetic factors. For drug targets and lead discovery and validation, for the clinical diagnosis and prognosis, for clinical treatment and therapy development, a standardized, universal DNA Array technology platform that has a full-range screening spectrum for all possible endogenous and exogenous genes seems more desirable.

The maintenance and replication of a genome-wide cDNA library demands quality controls. It can be time-consuming and add to the cost of production (Knight et al., Nature 414: 135-136, 2001). A cDNA library is a specialized library that may even have cell type specifics. Such characteristics set a limit for its applications. Another drawback is the probability of contamination during production. Zacharewski's laboratory has sequenced 1,189 cDNAs of a set of probes of DNA microarrays. Only 62% of them definitely represent the correct sequences (Halgren et al., Nucleic Acids Res. 29: 582-588, 2001). Up to 30% error rates of cDNA probes were also identified by three major centers of DNA microarrays (Knight, Nature 410: 860-861, 2001). Therefore, it is still in need to create new probe libraries, which have genuine genome-wide screening spectrum with more accuracy but low cost. Chemically synthesized oligonucleotides provide an alternative option. The process of chemical synthesis prevents problems from possible bacterial contamination and preserves the accuracy of designed sequences. Short oligonucleotides (9-30 mers) could be used as primer in Polymerase Chain Reaction (hereinafter PCR) whereas cDNA molecules generally could not, as most cDNA molecules are longer than 30 mers. For example, although expressed sequence tags (EST) have been widely used for gene discovery (Adams et al., Science 252: 1651-1656, 1991), they may not be able to be used as PCR primers directly. The length and GC content of EST are irregular. Thus, EST is unlikely for the use of standardized universal probes.

To address the above issues, the present invention proposes to construct a series of standardized universal probe libraries with all possible 61 or 64 genetic codes (codons) combinatorial according to a series of corresponding genetic algorithms. The inventive codon-based oligonucleotide probe libraries provide genuine genome-wide screening capability. It includes all possible point mutations and SNPs within the designed probe sequences. It has the capacity of targeting all possible endogenous and exogenous genes simultaneously for a given nucleic acid sample related to a biological or medical process or pathway. It is characterized by its unique all-purpose generic usage, regardless of genetic variations among cell types, tissues, organs, individuals and species. Moreover, codon-based oligonucleotide design has sequence orientation. A 5'-ATG oriented codon-based oligonucleotide library could be used as a library of upstream primers for PCR. With oligo-d(T)$_s$ as downstream primer, a corresponding cDNA library could be subsequently obtained from a given mRNA sample aided by RT-PCR. The cDNA library could then be used as probe library for cDNA Arrays. The protocols of making and using cDNA Arrays are known in the art (World Wide Website: stanford.edu/pbrown). The current invention presents oligonucleotide probes designed according to template strand of cDNA under DNA complementarity's rules. Hence, a brief review of gene structures for the probe design would be helpful.

While nucleic acids consist of four nucleotides with four distinct bases: Adenine (A), Thymine (T)/Uracil (U), Guanine (G) and Cytosine (C) respectively, the coding sequences of genes are organized in codons which in turn code for specific amino acids. Codons are arranged in an oriented, consecutive and linear manner with a unique starting and end point.

The codons (genetic code) consist of 64 nucleotide triplets: 61 codons encode the 20 essential L-amino acids (EAA) and three codons are stop codons. 5'-GTG, 5'-ATA, 5'-TTG, 5'-ACG and 5'-CTG may function as start codons such as, 5'-ATA is the start codon of mammalian mitochondria. 5'-ATG/5'-AUG is the dominant start codon. There are some exceptions. It is similar to stop codons. There are three dominant stop codons: 5'-TAA/5'-UAA, 5'-TGA/5'-UGA and 5'-TAG/5'-UAG. Exceptions exist. For example, in mammalian mitochondrial, 5'-AGA and 5-AGG are stop codons instead of coding for Arginine.

Although a specific coding region consists of a specific combination of a set of specific codons at a specific length, a given sequence with given length of Open Reading Frame (ORF) of a given gene could be identified among the group of linear consecutive DNA sequences consisting of all possible combinations of 61 codons that encode 20 (EAA). For example, each 5'-terminal sequence of a given ORF has a start codon at its 5'-end. Each 3'-terminal sequence of a given ORF has a stop codon at its 3-end. Thus, any and all terminal sequences of ORF of a given length could be deduced from either its 5'-end or 3'-end according to the genetic algorithm of $61^{(n-m)}$ under conditions: n−m=1 or n−m>1, n>m, n−m<infinity, neither n nor m is equal to zero, both n and m are integers, n is the unit of measurement of the length of ORF sequence, n represents the entire length of a given ORF sequence measured by codon or expressed codon (essential amino acid), m represents the length of the pre-determined sequence of terminal orientation for the entire sequence measured by codon or expressed codon (essential amino acid). For example, if 5'-ATG in 5'-ATGGCACTC is the pre-determined sequence of terminal orientation for the entire sequence, then n=3 and m=1. If n=3 and one 5'-ATG is at 5'-end, 3,721 distinct 5'-ATG oriented oligonucleotide sequences of three-codon-length long could be deduced according to algorithm of $61^{(n-m)}$. The length of three-codon equals nine-nucleotide (9 mers). The complete collection of above 3,721 distinctive 9-mer oligonucleotide sequences has formed a 9-mer codon-based oligonucleotide probe library accordingly.

5'-end terminal sequence of ORF of a given gene of a given length can be translated into a peptide sequence, which can be identified among the group of peptides of linear consecutive amino acids sequences consisting of all possible combinations of 20 (EM) with a L-amino acid encoded by a start codon at its N-terminal having the same unit number(s) of length as the corresponding 5'-terminal sequence of ORF. Methionine is encoded by 5'-ATG. Thus, any and all N-terminal peptide sequences of a given length could be deduced from its N-terminal(s) according to the genetic algorithm of $20^{(n-m)}$ as well under conditions: n−m=1 or n−m>1, n>m, n−m<infinity, neither n nor m is equal to zero, both n and m are integers, n is the unit of measurement of the length of peptide, n represents the entire length of a given peptide sequence measured by EAA (expressed codon), m represents the length of the pre-determined sequence of terminal orientation for the entire sequence measured by EAA (expressed codon). For example, if Methionine (M) in N-MKS Is the pre-determined sequence of terminal orientation for the entire sequence, then n=3 and m=1. If n=6 and one Methionine is at N-terminal (m=1), 3.2 million distinct N-Methionine oriented 6-EAA-length long peptide sequences could be deduced according to algorithm of $20^{(n-m)}$. The complete collection of the above 3.2 million distinctive 6-EAA-length long peptide sequences has formed a hexa-peptide library accordingly.

3'-end terminal sequence of ORF of a given gene of a given length can be translated into peptide sequence, which can be identified among the group of peptides of linear consecutive amino acids sequences consisting of all possible combinations of 20 (EAA) having the same unit number(s) of the length as the corresponding 3'-end terminal sequence of ORF. Thus, any and all C-terminal peptide sequences of a given length could be deduced from its C-terminal(s) according to the genetic algorithm of $20^{(n-m)}/20^n$ under conditions: n−m=1 or n−m>1, m=zero, n<infinity, n is not equal to zero, n is an integer, n is the unit of measurement of the length of peptide, one of the 20 EAA is at its C-terminal of each peptide of n-EAA-length long. For example, if n=5, 3.2 million distinct 5-EAA-length long peptide sequences of C-terminal orientation could be deduced according to algorithm of $20^n$. The complete collection of above 3.2 million distinctive 5-EAA-length long peptide sequences has formed a penta-peptide library accordingly.

The present invention defines 5'-start codon sequence as the common border of ORF and 5'-Untranslated Region (5'-UTR). Therefore, any 3'-end terminal sequence of 5'-UTR oriented by a start codon at its 3'-end of a given gene of a given length could be identified among the group of linear consecutive DNA sequences consisting of all possible combinations of 64 codons with a start codon at its 3'-end with the same given length. Thus, any and all 3'-end terminal sequences of 5'-UTR with a start codon at its 3'-end of a given length could be deduced from its 3'-end with a start codon according to the genetic algorithm of $64^{(n-m)}$ under conditions: n>m, n−m<infinity, neither n nor m is equal to zero, n and m are integers, n is the unit of measurement of the length of 5'-UTR sequence, n represents the entire length of a given 5'-UTR sequence measured by codon, m represents the length of the pre-determined sequence of terminal orientation for the entire 5'-UTR sequence measured by codon. When n=1 and m=1, position of codon is (m−n)+1. When n−m>1 and n−m<infinity, position of codon is (m−n). The negative sign in front of n indicates that the codon position is at 5'-UTR. For example, if n=3 and m=1 (one 5'-ATG of 5' towards 3' orientation is at 3'-end), 4,096 distinct 3'-GTA oriented oligonucleotide sequences of three-codon-length long could be deduced according to algorithm of $64^{(n-m)}$. The length of three-codon equals nine-nucleotide. The complete collection of above 4,096 distinctive 9-mer oligonucleotide sequences has formed a 9-mer codon-based oligonucleotide probe library accordingly.

The present invention defines a 5'-stop codon sequence as the common border of the ORF and 3'-Untranslated Region (3'-UTR). Therefore, a 5'-end terminal sequence of 3'-UTR with a stop codon at its 5'-end of a given gene of a given length can be identified among the group of linear consecutive DNA sequences consisting of all possible combinations of 64 codons with a stop codon at its 5'-end with the same length. Thus, any and all 5'-end terminal sequences of 3'-UTR with a stop codon at its 5'-end of a given length could be deduced from its 5'-end including a stop codon according to the genetic algorithm of $64^{(n-m)}$ under the conditions: n−m>1, n−m<infinity, neither n nor m is equal to zero, both n and m are integers, n is the unit of measurement of the length of 3'-UTR sequence, n represents the entire length of a given 3'-UTR sequence measured by codon, m represents the length of the pre-determined sequence of terminal orientation for the entire 3'-UTR sequence measured by codon. For example, if n=3 and m=1 (one 5'-TGA of 5' towards 3' orientation is at 5'-end), 4,096 distinct 5'-TGA oriented oligonucleotide sequences of three-codon-length long could be deduced according to algorithm of $64^{(n-m)}$. The length of three-codon equals nine-nucleotide. The complete collection of above 4,096 distinctive 9-mer oligonucleotide sequences has formed a 9-mer codon-based oligonucleotide probe library accordingly.

Exceptions exist. For example, 5'-TGA, which usually codes for the termination of the synthesis of a peptide chain, sometimes codes for selenocysteine, an amino acid which is not among the 20 essential amino acids. Other exceptions such as 5'-AGA and 5'-ATA are not usable in *Micrococcus Luteus* while 5'-CGG is not usable in Mycoplasmas and *Spiroplasmas* (Kanoi et al., J. Mol. Bio. 230: 51-56, 1993), (Oba et al., Proc. Natl. Acad. Sci. U.S.A. 88: 921-925, 1991). Both 5'-TAA and 5'-TAG encode Glutamine in Tetrahymena, Paramecium and Acetabularia of Cilliates and Algae while 5'-CTG encodes Serine in Candida cylindrica of Fungi (Tourancheau et al., EMBO J. 14: 3262-3267, 1995). However, all above genetic algorithms are applicable to those exceptions as long as the corresponding codon(s) are substituted accordingly. Therefore, the corresponding codon-based oligonucleotide probe library could be established as well.

The point mutations, deletions, insertion and single nucleotide polymorphisms (SNPs) may occur in the coding region or 5'-UTR or 3'-UTR. In terms of functionality, those genetic variation(s) in coding regions are actually a change(s) of codon(s) and/or ORF(s). For example, 5'-GCA encodes Alanine. If G, the single nucleotide of the first position of 5'-GCA, is swapped for an alternate (C, A and T), 5'-CCA encodes Proline; 5'-ACA encodes Threonine; 5'-TCA encodes Serine. If C, the single nucleotide of the second position of 5'-GCA, is swapped for an alternate (G, A and T), 5'-GGA encodes Glycine; 5'-GAA encodes Glutamic acid; 5'-GTA encodes Valine. If A, the single nucleotide of the third position of 5'-GCA, is swapped for an alternate (G, C and T), 5'-GCG encodes Alanine; 5'-GCC encodes Alanine; 5'-GCT encodes Alanine. 5'-GGA encodes Glycine. If G, the single nucleotide of the first position of 5'-GGA, is swapped for T, 5'-GGA will become 5'-TGA, terminator of the peptide chain. 5'-TAA, 5'-TGA and 5'-TAG encode peptide termination respectively. The substitution of any nucleotide at any position of the triplet codons of the three terminators will turn the terminator into a codon for a specific amino acid or another terminator. For example, If T, the single nucleotide of the first position of 5'-TGA, is swapped for an alternate (G, C and A), 5'-TGA, terminator of the peptide chain will become 5'-GGA, 5'-CGA and 5'-AGA which encodes Glycine, Arginine and Arginine respectively. If G, the single nucleotide of the second position of 5'-TGA, is swapped for an alternate (T, C and A), 5'-TGA, terminator of the peptide chain will become 5'-TTA, 5'-TCA and 5'-TAA which encodes Leucine, Serine and termination respectively. If A, the single nucleotide of the third position of 5'-TGA, is swapped for an alternate (G, C and T), 5'-TGA, terminator of the peptide chain will become 5'-TGG, 5'-TGC and 5'-TGT which encodes Tryptophan, Cysteine and Cysteine respectively. The substitution, replacement, deletion and insertion of single or multiple nucleotide(s) in the coding region could cause the shift of ORF(s) and the change(s) of codon(s), the termination of peptide chain and/or the merger of two or more peptide chains together. In appearance, the point mutation, deletion, insertion and SNPs in the coding region is a change(s) of nucleotide(s). In nature, it is actually a change(s) of codon(s) and/or ORF(s). Therefore, codon-based methods could address the nature of those phenomena more directly in comparison with the nucleotide-based methods.

Due to the reductions of the conservations of amino acids near both terminals of peptide chain, terminal sequence tag (TST) of either 5'-end or 3'-end of ORF or combinatorial may have the potential for signature sequence selection. Practically, oligonucleotides ranging from 6 to 24 mers are sufficient to function as probes in hybridization. Therefore, construction of Terminal Sequence Tag (TST) Libraries could become meaningful (Chen et al., Molecular & Cellular Proteomics 2(9): 826, 2003). Although there is often more than one 5'-ATG codon per single gene, such as the full length sequence of Glyceraldehyde-3-phosphate Dehydrogenase (GenBank Accession: NM_002046.2) which has ten 5'-ATG codons in its ORF at the first reading. The first suitable 5'-ATG is usually the start codon. The identification of every 5'-ATG/5'-AUG of a given single gene could facilitate the identification of the start codon and the start site of the ORF of a given gene. Technically, mRNA sequences between 5'-AUG sites and poly(A) could routinely be amplified by RT-PCR and visualized on Agarose gel by electrophoresis. The size of the cDNA fragments on the Agarose gel reflected the length of the targeted sequences. As a rule of thumb, the start codon sites are more included in cDNA fragments above the size of 0.6K base pairs (b.p.), if mRNA sample of human cells were used. It is estimated that there are 30,000 to 40,000 expressed genes for the entire human genome (Baltimore, Nature 409: 816-818, 2001). Assuming the average length of an ORF is 1,320 b.p. with 30 5'-ATG sites (World Wide Website: kazusa.or.ip), 900,000 to 1,200,000 possible 5'-ATG sites of ORF were estimated. The design of codon-based oligonudeotide would allow producing genome-wide probes libraries; from which contain 226,981 distinctive 12-mer or 13,845,841 distinctive 15-mer oligonucleotide probes respectively (TABLE 16). The number of the designed probes is sufficient to target those 900,000 to 1,200,000 possible 5'-ATG sites and their immediate downstream sequences by hybridization. Argarose gel electrophoresis could help to filter out many fragments lacking non-start codon sites, typically those under 0.6 k b.p. in size. Technically, the density of 400,000 probes per individual DNA microarray could go to 40 million probes on one single DNA microarray soon (Gwynne et al., Science 294:641-677, 2001). Particularly, using the photolithographic process, a large number of oligonucleotide probes could be synthesized on the surface of a wafer without increasing the cost of microarrays (Fodor et al., U.S. Pat. No. 5,510,270, 1996). In practice, a complete set of 13,845,841 distinctive 5'-ATG oriented oligonucleotide probes (13,845,841.times.40) could be immobilized on 14 individual DNA microarrays in future. Those numbers of probe sequences are no more astronomical figures in reality.

Practically, the selection of initiation site as targeting site has certain advantages over 5'-cap regions. The method of targeting 5'-cap region of mRNA is Rapid Amplification of cDNA Ends (RACE). It has been described by Frohman et al., Proc. Natl. Acad. Sci. U.S.A. 85: 8998-9002, 1988; Maruyama et al., Gene 138: 171-174, 1994. RACE uses Calf Intestinal Phosphatase (CIP) to remove 5'-end phosphates of uncapped mRNA molecules while leaving the 5'-capped mRNA intact. Subsequently, Tobacco Acid Pyrophosphatase (TAP) is added to reaction to remove the 5'-cap of 5'-capped mRNA molecules. After removal, the 5'-phosphate of the uncapped mRNA is exposed to the environment. Then, the oligonucleotide designed as the PCR primer and T4 RNA ligase is added to the reaction. The 3'-hydroxyl group of the oligonucleotide will ligate to the 5'-phosphate group of the mRNA in a reaction catalyzed by T4 RNA ligase. Thus, RACE eliminates the uncapped mRNAs and selects ones with a 5'-cap for further PCR aided cloning. The disadvantage is that mRNA molecules with full-length sequence without a 5'-cap may be eliminated from samples. Furthermore, it is not unusual for there to be a several hundred base pair long distance between the 5'-cap and the start codon of mRNA in vertebrates. The relatively rich GC content of 5'-UTR in many cases suggests that a high degree of secondary structure may exist (Kozak, J. Cell Biol. 115: 887-903, 1991). That may lead to problems which will have a negative Impact on PCR priming from 5'-UTR adjacent to 5'-cap. It is also noted that non-template nucleotides could be added to 3'-ends of cDNAs during RACE process (Chen et al., Biotechniques 30: 574-582, 2001). Chen et al. has recommended that RACE should be used cautiously in determining the terminal sequences of nucleic acids.

The present invention allows targeting of the site of 5'-ATG to be substituted by any one of 61 amino acid coding codons for ORFS or 64 codons for 5'-UTRs and 3'-UTRs. Based on the present Inventive genomic algorithms, a given site of ORF or 5'-UTR or 3'-UTR and their corresponding downstream or upstream sequences could be targeted specifically by the inventive probes.

The study of the probabilities of priming site in DNA of 45,000 base pair indicated that P(O), the probability of no priming site of 12-mer oligonucleotides, is 0.995. P(1), the probability of exactly one priming site of 12-mer oligonucleotides, is 0.005. P(>1), the probability of more than one priming site of 12-mer oligonucleotides, is <$10^{-4}$ (<10.sup.-4) (Studier, Proc. Natl. Acad. Sci. U.S.A. 86: 6917-6921, 1989). Theoretically, an oligonucleotide with the length of 15 to 18 mers or above could be able to detect a single copy gene from the human genomic DNA. In practice, a 12-mer oligonucleotide is capable of detecting an mRNA molecule. Long oligonucleotides (>10 mers) may decrease the specificity if its binding affinity is high (Herschlag et al., Proc. Natl. Acad. Sci. U.S.A. 88: 6921-6925, 1991).

It is known in the art that an oligonucleotide as short as a 6 mers could perform reliable hybridization (Drmanac et al., DNA and Cell Biology 9: 527-534, 1990) and prime efficiently (Feinberg et al., Anal. Biochem. 132: 6-13, 1983). The results of 6-mer Oligonucleotide arrays have been reported (Timofeev et al., Nucleic Acids Res. 29(12): 2626-2634, 2001). The advantage of using short oligonucleotide is the higher capacity of discriminating mismatches than longer probes in hybridization (Drmanac et al., DNA and Cell Biology 9: 527-534, 1990). Beattie et al. have demonstrated experimentally that 9-mer oligonucleotides tethered to glass were capable of capturing their complementary DNA strands as long as 1,300 bases in length with good discrimination against mismatches in hybridization (Beattie et al., Mol. Biotechnol. 4: 213-225, 1995). Recent research has demonstrated the usage of 9-mer oligonucleotide arrays in DNA fingerprinting (Reyes-Lopez et al., Nucleic Acids Res. 31(2): 779-789, 2003). 9-mer oligonucleotide has been proven to be sufficient to perform as a PCR primer in aqueous phase (Williams et al., Nucleic Acids Res. 18: 6531-6535, 1990). Additionally, if Locked Nucleic Acid hereinafter LNA had been incorporated, short oligonucleotides would exhibit increasing thermal stabilities towards complementary DNA and RNA in PCR and hybridization (Babu et al., Nucleic Acids Res. 22: 1317-1319, 2003). Milner et al. speculated that longer oligonucleotides might have internal base pairing which prevent duplex formation, or that duplex formation was inhibited by dangling ends of oligonucleotides that could not fit into the folded structure of mRNA (Milner et al., Nat. Biotechnol. 15: 537-541, 1997). Considering the increasing probability of forming secondary structure(s) that accompanies the increasing length of an oligonucleotide; a short oligonucleotide has distinct advantages over a longer one though longer ones are more specific. Short oligonucleotides are also relatively inexpensive and suitable for large-scale production.

In the art, some oligonucleotide probes and PCR primers were designed specifically against their corresponding template sequences directly. Some were designed based on nucleotides using the algorithm of $4.\sup.n$ (n is the unit of measurement of the length of oligonucleotide. n represents nucleotide) that has been widely used and prevailed up to date. Algorithm of $4.\sup.n$ has a fundamental impact on oligonucleotide designs and production though some were designed systematically and others were designed arbitrarily. Those are oligonucleotide probes for general usage (Studier, Proc. Natl. Acad. Sci. U.S.A. 86: 6917-6921, 1989) (Szybalski et al., Gene 90: 177-178, 1990), oligonucleotide probes for generic oligonulceotide mlcroarray (Llpshutz et al., Nature Genetics 21, 20-24, 1999) (Barinaga, Science 253: 1489, 1991) as well as PCR primers for RT-PCR differential display (Liang et al., Science 257: 967-971, 1992).

The oligonucleotide library constructed by all possible combinations of A.T.G.C. according to algorithm of $4.\sup.n$ was proposed (Studier, Proc. Natl. Acad. Sci. U.S.A. 86: 6917-6921, 1989) (Szybalski, Gene 90: 177-178, 1990). Huse introduced the concept of random tuplets in the method of oligonucieotide's synthesis. A tuplet can be a dinucleotide, a trinucleotide or can also be four or more nucleotides (Huse, U.S. Pat. No. 5,523,388, 1996 and U.S. Pat. No. 5,808,022, 1998). The proposal of synthesizing a diverse population of expressible oligonucleotides having a desirable bias of random codon sequences, which encode a desirable bias of amino acids, was suggested by Huse (Huse, U.S. Pat. App. No.2001/0024782, 2001) (Huse, U.S. Pat. No. 6,258,530, 2001). Huse proposed an algorithm of $20.\sup.n$ (20", n is the unit of measurement of the length of oligonucleotide. n represents nucleotide.) for the calculation of all possible combinations of four-nucleotide/bases of n-nucleotide-lenqth long oligonucleotide sequences. However, neither algorithm $4.\sup.n$ nor $20.\sup.n$ has orientation capacity. None of the oligonucleotides of the oligonucleotide library constructed in accordance with algorithm of $4.\sup.n$ or algorithm of $20.\sup.n$ could be able to discriminate the template strand (anti-sense) from non-template strand (sense) of a DNA double helix and vice versa in hybridization. Another disadvantage is that both algorithms inevitably include huge amounts of non-sense codons in the sequences of oligonucleotides that virtually do not exist in ORF. For example, for 6-mer oligonucleotides (six nucleotides in the length), 4,096 ($4.\sup.9$) oligonucleotide sequences were deduced by Studier and Szybalski's method; 64,000,000 ($20.\sup.6$) oligonucleotide sequences were deduced by Huse's method. Only 61 ($61.\sup.1$) 5'-ATG oriented 6-mer oligonucleotide sequences were deduced by the inventive methods. Obviously, algorithm of $61.\sup.(n-1)$ is the most effective one for designing oligonucleotide libraries. The redundant non-sense codons in probe sequences created by algorithm of $4.\sup.n$ are problems when they were massively employed to target ORF sequences on HTS technology platforms such as DNA Microarrays. The negative impacts on noise control, fidelity, reliability and cost effective can hardly be ignored.

DNA Microarrays, a format of DNA Array technology platforms, is a systematic approach of detecting gene expression patterns in a quantitative, parallel, simultaneous and massive manner (Fodor et al., Science 251: 767-773, 1991); (Schena et al., Science 270: 467-470, 1995); (Fodor et al., U.S. Pat. No. 5,510,270, 1996 and U.S. Pat. No. 5,800,992, 1998); (Southern et al., U.S. Pat. No. 5,700,637, 1997); (Chu et al., Trends in Blotechnol. 17: 217-218, 1999). It usually consists of hundreds to thousands of known DNA sequences immobilized on a miniaturized solid surface as the probes. Each distinctive DNA sequence immobilized has its own well-defined position on the substrate. Through hybridization, DNA Microarrays could identify and demonstrate the responsive sequences, expression dynamics and patterns of genes of a given sample. It can visualize the results of the hybridization of thousands of cDNA molecules in one single experiment. Nucleic acids of a given test and control samples were usually previously labelled with fluorescent molecules, such as Cy3 and Cy5 respectively. There are cases wherein the nucleic acids of a given sample were radioactively labelled, for example with $^{33}P$, $^{32}P$ and $^{33}S$. Oligonucleotide Arrays usually range in length from 4 mers to 80 mers. Though longer oligonucleotides are more specific, they are usually more costly to make and more difficult to accurately synthesize. Those oligonucleotides were either pre-synthesized or synthesized in situ. For example, Affymetrix's GeneChip arrays are synthesized by light-directed combinatorial chemical approaches which allow manufacture of high density oligonucleotide arrays consisting of above 0.5 million distinctive oligonucleotides on $1.2 \times 1.2$ cm.sup.2 glass surfaces (Fodor et al., Science, 251: 767-773, 1991). Concerning the probe design, Inc. has developed generic oligonucleotide arrays. The design was based on all possible combinations of four nucleotides or bases (A.T.G.C.) according to algorithm of 4.sup.n. (Lipshutz et al., Nat. Genet. 21: 20-24, 1999). In fact, it is the same model and system proposed by Studier. As a systematical approach, the disadvantages can hardly to be ignored. First, the oligonucleotide set or library constructed by all possible combinations of four nucleotides cannot discriminate target sequences among non-coding, coding and regulatory regions. Second, even within a targeting coding region, template strand (anti-sense) and non-template strand (sense) would be targeted indifferently by those generic oligonucleotides in hybridization. Third, one of the analytical areas of gene functionality is in coding regions, but the algorithm of 4.sup.n is not a codon-based approach. The redundancy is phenomenal and hinders the accuracy of hybridization. It increases the cost of production and complicates the operation. For example, for 24-mer oligonucleotides, the number of all possible combinations of oligonucleotides based on algorithm of 61.sup.(n−1) is 382,742,836,021 [61.sup.(8−1)] while the number of all possible combinations of oligonucleotides based on algorithm of 4.sup.n Is 281,474, 976,710,656 (4.sup.24). The relationship between codon and nucleotide regarding the length of an oligonucleotide is as follows: n-codon-length long oligonucleotide equals 3.times. n-nucleotide-length long oligonucleotide. n represents codon while 3 multiply n represents nucleotide. The redundancy is 89.6 times more than the virtual ORF sequences (TABLE 17). Furthermore, producing a 24-mer oligonucleotide library for oligonucleotide arrays by the present invention is 89.6 times more cost-effective in production than the design based on algorithm of 4.sup.n. That efficiency will increase further with the elongation of the length of oligonucleotide following algorithm of 4.sup.3.times.n divided by 61.sup.(n−1) (TABLE 17). The redundancy of oligonucleotide sequence with specified length could be calculated in accordance with the algorithm of $4^{3n}-61^{(n-1)}$ (TABLE 17). Since the generic oligonucleotide arrays were constructed according to algorithm of 4.sup.n., the GC contents among the oligonucleotide probes vary from 0% to 100%. Once thousands of oligonucleotides with variable GC content are immobilized on one piece of solid support, all of them will be exposed to a unique hybridization environment. Thus, a considerable number of the oligonucleotide probes may have to hybridize under un-optimized conditions. Consequently, false positive or negative hybridization results might be produced. Applying 2.4 to 3.0 M tetramethyl ammonium or tetraethyl ammonium chloride (Wood et al., Proc. Nati. Acad. Sci. U.S.A. 82: 1585-1588, 1985) as buffer (Fodor et al., U.S. Pat No. 6,197,506, 2001) may reduce some effects of the GC bias in hybridization to a certain degree. However, the effect of such reagents has its limitations.

The standardization and optimization of oligonucleotide probe design are among the major challenges to DNA Array developers. A novel, standardized and universal probing system (libraries) having the capacity of genuine genome-wide screening without any redundancy is desirable. Ideally, the standardized oligonucleotide arrays are all-purpose probe platforms. It can target regardless of genetic variations among cells, tissues, organs, individual, species and diverse life processes such as various pathways of both normal and pathological states. It is capable of detecting and targeting all low-abundance transcripts as well as medium and high-abundance transcripts of a given nucleic acid sample at the same time. The targeting range could include all possible endogenous and exogenous genes known and unknown simultaneously and systematically for a given nucleic acid sample. Tactically, the one-for-all approach Is one of the most effective and economical designs for both users and manufactures of DNA Arrays.

The citation of a reference herein and hereafter shall not be construed as an admission that such reference is prior art to the present invention.

SUMMARY OF THE INVENTION

The invention envisions a coding region, such as ORF of a gene as a linear polymer selected from a group consisting of all possible combinations of 61 amino acid coding codons with a start codon at its 5'-end and a stop codon at its 3'-end. 61 amino acid coding codons are referred to 61 codons hereinafter. This is different from the traditional concept which perceives a gene as a linear DNA sequence selected from a group consisting of all combinations of four distinct nucleotide of A, T, G and C whether coding region, 5'-UTR or 3'-UTR. With the invention, any coding region, such as ORF is selected from a group consisting of all possible combinations of 61 codons with a start codon at its 5'-end and a stop codon at its 3'-end. A 5'-UTR is selected from a group consisting of all possible combinations of 64 codons with a start codon at its 3'-end. A 3'-UTR is selected from a group consisting of all possible combinations of 64 codons with a stop codon adding at its 5'-end. Applying innovative concepts makes it possible to differentiate the genes of mammalian genomic DNA origin from mitochondrial genes. The genes of mammalian mitochondria possess unique characteristics: for example, 5'-ATA replaces 5'-ATG for Met; 5'-TGA encodes Tip instead of termination. Therefore, a given coding region of a given gene of mammalian mitochondria could be envisioned as one selected from the group of linear DNA sequences consisting of all possible combinations of 59 codons in which 5'-ATA substitutes 5'-ATG and 5'-TGA substitutes for 5'-AGA and 5'-AGG of the group of 61 codons. Such a linear DNA sequence has 5'-ATA at its 5'-end as the start codon and one of 5'-AGA, 5'-AGG and 5'-TAA at its 3'-end as stop codon. The invention envisions a gene product such as a peptide or polypeptide as a linear polymer selected from a group consisting of all possible combinations of 20 essential amino acids (EAA) with an amino acid encoded by a 5'-start codon, such as Methionine at its N-terminal. The 20 EAA are perceived as the expressed codons of 61 codons in the view of this invention.

(1) A library with 5'-end start codon orientation: the library of oligonucleotides consists of all possible combinations of 61 codons (TABLE 1) with a start codon, such as 5'-ATG, as 5'-end terminal codon for each oligonucleotide at a given length (TABLE 7) and a peptide library corresponding to amino acids sequences deduced from amino acid coding sequences (TABLE 15). The length of the entire sequence (n) of each oligonucleotide including pre-determined sequence of orientation (m) in within was measured by codon. n is an integer. m is an integer. n>m. m=1. 5'-ATG is pre-determined sequence of orientation within the entire sequence of each oligonucleotide of the library. The length of pre-determined sequence of orientation (m) was measured by codon or expressed codon. As will be appreciated by one of skill in the art, the result of this arrangement is that the oligonucleotides will preferentially hybridize to regions of template strand (antisense) of genomic DNA, or $1^{st}$ single strand of cDNA upstream of and including an antisense start codon, such as 5'-CAT within the antisense coding region of antisense ORF of 5' towards 3' orientation due to the fact that sequences corresponding to termination codons are specifically excluded.

(2) A library with 3'-end antisense start codon orientation: the library of antisense oligonucleotides consists of all possible combinations of 61 antisense amino acid coding codons (TABLE 2) with an antisense start codon, such as 5'-CAT, as the 3'-end terminal antisense codon for each antisense oligonucleotide at a given length (TABLE 11). 61 antisense amino acid coding codons are referred to 61 antisense codons hereafter. The length of the entire antisense sequence (n) of each antisense oligonucleotide including pre-determined antisense sequence of orientation (m) in within was measured by antisense codon. n is an Integer. m is an integer. n>m. m=1. 5'-CAT is pre-determined antisense sequence of orientation of the entire antisense sequence within each antisense oligonucleotide of the library. The length of pre-determined antisense sequence of orientation (m) was measured by antisense codon. As will be appreciated by one of skill in the art, these antisense oligonucleotides will preferentially hybridize to regions of nontemplate strand (sense) of genomic DNA, or mRNA or $2^{nd}$ single strand of cDNA downstream of and including a start codon such as 5'-ATG within the coding region of ORF of 5' towards 3' orientation due to the fact that antisense sequences corresponding to termination codons are specifically excluded.

(3) A library with 3'-end stop codon orientation: the library of oligonucleotides consists of all possible combinations of 61 codons (TABLE 1) with a stop codon, such as 5'-TGA as 3'-end terminal codon for each oligonucleotide at a given length (TABLE 8) and a peptide library corresponding to amino acids sequences deduced from amino acid coding sequences excluding 3'-end stop codon (TABLE 16). The length of the entire sequence (n) of each oligonucleotide including pre-determined sequence of orientation (m) in within was measured by codon. n is an integer. m is an integer. n>m. m=1. 5'-TGA Is pre-determined sequence of orientation within the entire sequence of each oligonucleotide of the library. The length of pre-determined sequence of orientation (m) was measured by codon or expressed codon. As will be appreciated by one of skill in the art, the result of this arrangement is that the oligonucleotides will preferentially hybridize to regions of template strand (antisense) of genomic DNA, or $1^{st}$ single strand of cDNA downstream of and including an antisense stop codon such as 5'-TCA within the antisense coding region of antisense ORF of 5' towards 3' orientation due to the fact that sequences corresponding to termination codons are specifically excluded.

(4) A library with 5'-end antisense stop codon orientation: the library of antisense oligonucleotides consists of all possible combinations of 61 antisense codons (TABLE 2) with an antisense stop codon, such as 5'-TCA, as 5'-end antisense terminal codon for each antisense oligonucleotide at a given length (TABLE 12). The length of the entire antisense sequence (n) of each antisense oligonucleotide including pre-determined antisense sequence of orientation (m) in within was measured by antisense codon. n is an integer. m is an integer. n>m. m=1. 5'-TCA is pre-determined antisense sequence of orientation within the entire antisense sequence of each antisense oligonucleotide of the library. The length of pre-determined antisense sequence of orientation (m) was measured by antisense codon. As will be appreciated by one of skill in the art, these antisense oligonucleotides will preferentially hybridize to regions of nontemplate strand (sense) of genomic DNA, or mRNA or $2^{nd}$ single strand of cDNA upstream of and including a stop codon such as 5'-TGA within the coding region of ORF of 5' towards 3' orientation due to the fact that antisense sequences corresponding to termination codons are specifically excluded.

(5) A library with orientations of either 5'-end two-codon-restriction-enzyme-recognition sequence or 3'-end two-codon-restriction-enzyme-recognition sequence (TABLE 5): For example, the library of oligonucleotides consists of all possible combinations of 61 codons (TABLE 1) with a two-codon-restriction-enzyme-recognition sequence, such as 5'-GACGTC (Aat II), as 5'-end terminal oriented two consecutive codons for each oligonucleotide at a given length and a peptide library corresponding to amino acids sequences deduced from amino acid coding sequences. The length of the entire sequence (n) of each oligonucleotide including pre-determined sequence of orientation (m) in within was measured by codon. n is an integer. m is an integer. n>m. m=2. 5'-GACGTC (Aat II) is pre-determined sequence of orientation within the entire sequence of each oligonucleotide of the library. The length of pre-determined sequence of orientation (m) was measured by codon or expressed codon. As will be apparent to one of skill in the art, the restriction-endonuclease-recognition sequences that are on amino acid codons basis and termination codons within their recognition sequences are omitted from the library. The result of this arrangement is that the oligonucleotides will preferentially hybridize to regions of template strand (antisense) of genomic DNA, or $1^{st}$ single strand of cDNA upstream of and including an antisense-two-codon-restriction-endonuclease-recognition sequence, such as 5'-GACGTC (Aat II), within the antisense coding region of antisense ORF of 5' towards 3' orientation due to the fact that sequences corresponding to termination codons are specifically excluded.

(6) A library with orientations of either 3'-end antisense-two-codon-restriction-endonuclease-recognition sequence or 5'-end antisense-two-codon-restriction-endonuclease-recognition sequence (TABLE 5): For example, the library of antisense oligonucleotides consists of all possible combinations of 61 antisense codons (TABLE 2) with an antisense-two-codon-restriction-endonuclease-recognition sequence, such as 5'-GACGTC (Aat II), as 3'-end terminal two consecutive antisense codons for each antisense oligonucleotide at a given length. The length of the entire antisense sequence (n) of each antisense oligonucleotide including pre-determined antisense sequence of orientation (m) in within was measured by antisense codon. n is an integer. m is an integer. n>m. m=2. 5'-GACGTC (Aat II) is pre-determined antisense sequence of orientation within the entire antisense sequence of each antisense oligonucleotide of the library. The length of pre-determined antisense sequence of orientation (m) was measured by antisense codon. As will be apparent to one of skill in the art, antisense restriction endonuclease recognition sequences that are on the antisense amino acid codon basis and antisense termination codons within their antisense recognition sequence are omitted from the library. The result of this arrangement Is that these antisense oligonucleotides will preferentially hybridize to regions of nontemplate (sense) strand of genomic DNA, or mRNA or $2^{nd}$ single strand of cDNA downstream of and including a two-codon-restriction-enzyme-recognition sequence, such as 5'-GACGTC (Aat II), within the coding region of ORF of 5' towards 3' orientation due to the fact that antisense sequences corresponding to termination codons are specifically excluded.

(7) A library with orientations of either 5'-end two-codon-restriction-enzyme-recognition sequence or 3'-end twocodon-restriction-enzyme-recognition sequence (TABLE 6): For example, the library of oligonucleotides consists of all possible combinations of 64 codons (TABLE 4) with a two-codon-restriction-enzyme-recognition sequence, such as 5'-TCATGA (BspH I), as 5'-end terminal oriented two consecutive codons for each oligonucleotide at a given length. The length of the entire sequence (n) of each oligonucleotide including pre-determined sequence of orientation (m) in within was measured by codon. n is an integer. m is an integer. n>m. m=2. 5'-TCATGA (BspH I) is pre-determined sequence of orientation within the entire sequence of each oligonucleotide of the library. The length of pre-determined sequence of orientation (m) was measured by codon. As will be apparent to one of skill in the art, the restriction endonuclease recognition sequences that are on codon basis include termination codons within their recognition sequences are included in the library. The result of this arrangement is that the oligonucleotides will preferentially hybridize to regions of template strand (antisense) of genomic DNA, or $1^{st}$ single strand of cDNA upstream of and including an antisense-two-codon-restriction-endonuclease-recognition sequence, such as 5'-TCATGA (BspH I), within the antisense 5'-UTR or downstream of and including an antisense-two-codon-restriction-endonuclease-recognition sequence, such as 5'-TCATGA (BspH I), within the antisense 3'-UTR regions of 5' towards 3' orientation due to the fact that sequences corresponding to termination codons are specifically included.

(8) A library with orientations of either 3'-end antisense-two-codon-restriction-endonuclease-recognition sequence or 5'-end antisense-two-codon-restriction-endonuclease-recognition sequence (TABLE 6): For example, the library of antisense oligonucleotides consists of all possible combinations of 64 antisense codons (TABLE 6) with an antisense-two-codon-restriction-endonuclease-recognition sequence, such as 5'-TCATGA (BspH I), as the 3'-end terminal two consecutive antisense codons for each antisense oligonucleotide at any given length. The length of the entire antisense sequence (n) of each antisense oligonucleotide including pre-determined antisense sequence of orientation (m) in within was measured by antisense codon. n is an integer. m is an integer. n>m. m=2. 5'-TCATGA (BspH I) is pre-determined antisense sequence of orientation within the entire antisense sequence of each antisense oligonucleotide of the library. The length of pre-determined antisense sequence of orientation (m) was measured by antisense codon. As will be apparent to one of skill in the art, antisense restriction endonuclease recognition sequences that are on the antisense codon basis and include antisense termination codons within their antisense recognition sequence are included in the library. The result of this arrangement is that these antisense oligonucleotides will preferentially hybridize to regions of nontemplate (sense) strand of genomic DNA, or mRNA or $2^{nd}$ single strand of cDNA downstream of and including a two-codon-restriction-enzyme-recognition sequence, such as 5'-TCATGA (BspH I) within 5'-UTR or downstream of and including an two-codon restriction endonuclease recognition sequence, such as 5'-TCATGA (BspH I), within 3'-UTR regions of 5' towards 3' orientation due to the fact that antisense sequences corresponding to termination codons are specifically included.

(9) A library with 3'-end start codon orientation: the library of oligonucleotides consists of all possible combinations of 64 codons (TABLE 3) with a start codon, such as 5'-ATG, as 3'-end terminal codon for each oligonucleotide at a given length (TABLE 9). The length of the entire sequence (n) of each ollgonucleotide including pre-determined sequence of orientation (m) in within was measured by codon. n is an integer. m is an integer. n>m. m=1. 5'-ATG is pre-determined oriented-sequence sequence of orientation within the entire sequence of each oligonucleotide of the library. The length of pre-determined sequence of orientation (m) was measured by codon. As will be appreciated by one of skill in the art, the result of this arrangement is that the oligonucleotides will preferentially hybridize to Antisense 5'-Untranslated Region (Antisense 5'-UTR) of template strand (antisense) of genomic DNA, or $1^{st}$ single strand of cDNA downstream of and including an antisense start codon such as 5'-CAT of antisense ORF and within Antlsense 5'-UTR of 5' towards 3' orientation due to the fact that sequences corresponding to termination codons are specifically included.

(10) A library with 5'-end antisense start codon orientation: the library of antisense oligonucleotides consists of all possible combinations of 64 antisense codons (TABLE 4) with an antisense start codon, such as 5'-CAT, as the 5'-end terminal antisense codon for each antisense oligonucleotide at a given length (TABLE 13). The length of the entire antisense sequence (n) of each antisense oligonucleotide including pre-determined antisense sequence of orientation (m) in within was measured by antisense codon. n is an integer. m is an integer. n>m. m=1. 5'-CAT is pre-determined antisense sequence of orientation within the entire antisense sequence of each antisense oligonucleotide of the library. The length of pre-determined antisense sequence of orientation (m) was measured by antisense codon. As will be appreciated by one of skill in the art, these antisense oligonucleotides will preferentially hybridize to 5'-Untranslated Region (5'-UTR) of nontemplate strand (sense) of genomic DNA, or mRNA or $2^{nd}$ single strand of cDNA upstream of and including a start codon such as 5'-ATG of ORF and within 5'-UTR of 5' towards 3' orientation due to the fact that antisense sequences corresponding to termination codons are specifically included.

(11) A library with 5'-end stop codon orientation: the library of oligonucleotides consists of all possible combinations of 64 codons (TABLE 3) with a stop codon, such as 5'-TGA, as 5'-end terminal codon for each oligonucleotide at a given length (TABLE 10). The length of the entire sequence (n) of each oligonucleotide including pre-determined sequence of orientation in within was measured by codon. n is an integer. m is an integer. n>m. m=1. 5'-TGA Is pre-determined sequence of orientation within the entire sequence of each oligonucleotide of the library. The length of pre-determined sequence of orientation (m) was measured by codon. As will be appreciated by one of skill in the art, the result of this arrangement is that the oligonucleotides will preferentially hybridize to Antisense 3'-Untranslated Region (Antisense 3'-UTR) of template strand (antisense) of genomic DNA, or $1^{st}$ single strand of cDNA upstream of and including an antisense stop codon, such as 5'-TCA of antisense ORF and within the antisense 3'-UTR of 5' towards 3' orientation due to the fact that sequences corresponding to termination codons are specifically included.

(12) A library with 3'-end antisense stop codon orientation: the library of antisense oligonucleotides consists of all possible combinations of 64 antisense codons (TABLE 4) with an antisense stop codon, such as 5'-TCA, as the 3'-end terminal antisense codon for each antisense oligonucleotide at a given length (TABLE 14). The length of the entire antisense sequence (n) of each antisense oligonucleotide including pre-determined antisense sequence of orientation (m) in within was measured by antisense codon. n is an integer. m is an integer. n>m. m=1. 5'-TCA is pre-determined sequence antisense sequence of orientation within the entire antisense sequence of each antisense oligonucleotide of the library. The length of pre-determined antisense sequence of orientation (m) was measured by antisense codon. As will be appreciated by one of skill in the art, these antisense oligonucleotides will preferentially hybridize to 3'-Untranslated Region (3'-UTR) of nontemplate strand (sense) of genomic DNA, or mRNA or $2^{nd}$ single strand of cDNA downstream of and including a stop codon such as 5'-TGA of ORF and within 3'-UTR of 5' towards 3' orientation due to the fact that antisense sequences corresponding to termination codons are specifically included.

There is also provided an oligonucleotide library comprising a plurality of oligonucleotides, wherein each of the oligonucleotides is represented by the formula 5'-(Cs).sub.n–3', wherein $C_s$ represents an amino acid coding codon in sense orientation, n is an integer and n represents the length of said oligonucleotide measured by codon.

There is also provided an oligonucleotide library comprising a plurality of oligonucleotides, wherein each of the oligonucleotides is represented by the formula 5% $(C_A)$.sub.n–3', wherein $C_A$ represents an amino acid coding codon in antisense orientation, n is an integer and n represents the length of said oligonucleotide measured by codon.

There is also provided a peptide library comprising a plurality of peptides, wherein each of said peptides is deduced from an said oligonucleotide represented by said formula 5'-(Cs).sub.n–3', wherein $C_s$ represents an amino acid coding codon in sense orientation, n is an integer and n represents the length of said oligonucleotide measured by codon.

There is also provided an oligonucleotide library comprising a plurality of oligonucleotides, wherein each of said oligonucleotides is represented by said formula 5'-$(V_s)$.sub.n–3', wherein $V_s$ represents a codon, n is an integer, and n represents the length of the said oligonucleotide measured by codon(s), each said oligonucleotide further comprising a linker at either 5'-end or 3'-end of said oligonucleotide, the said linker being selected from the group consisting of: a termination codon in sense orientation; a termination codon in antisense orientation; a codon in sense orientation; two consecutive codons In sense orientation; two consecutive codon restriction endonuclease recognition site in sense orientation; two consecutive codon restriction endonuclease recognition site in antisense orientation; three consecutive codons in sense orientation; a consecutive oligo-d(T)$_s$ consisting of a plurality of thymidine nucleotides; a codon comprising one universal base; a codon comprising two universal bases; a codon comprising three universal bases; and combinations thereof.

The present invention provides a general universal genetic algorithm, from which stems a series of universal genetic algorithms. It provides a universal calculation formula for the total number of sequences at a given length measured by either the number of codon or L-amino acid encoded by codon as the unit when the orientation has been determined. The orientation for a sequence of a gene could be either 5'- or 3'-orientation. The orientation for a peptide sequence, the product of a gene, could be either N-terminal or C-terminal orientation. The length measured by codons can convert to the length measured by single nucleotides by multiplying by 3.

The algorithms are applicable to sense and anti-sense strands of a gene and all the corresponding gene products, such as mRNA, cDNA, anti-sense RNA, anti-sense cDNA, peptide and protein. The general universal genetic algorithm is presented herein:

$$Y = X^{(n-m)}$$

(1) Definition of X
Nucleic Acids:
X: The number of all distinct codons. X is a variable. X is an integer. X is not equal zero. X is from 1 to infinity. At the current evolutionary stage: For all distinct codons, X=64. For all distinct codons that encode L-amino acid, X=61.
Peptides:
X: The number of all distinct L-amino acids encoded by at least one codon. X is a variable. X is an integer. X is not equal zero. X is from 1 to infinity. At the current evolutionary stage: 20 distinct essential L-amino acids that are encoded by 61 distinct corresponding codons. X=20.

(2) Definition of n
Nucleic Acids:
n: number of all codons arranged linearly without overlapping per sequence including pre-determined sequence of orientation (m) in within. n is a variable. n is an integer. n is not equal zero. n<infinity. n represents the length of sequence measured by codon (triplet of nucleotides). n represents serial numbers of codons counted from either 5'-or 3'-end of a sequence.
Peptides:
n: number of all L-amino acids arranged linearly without overlapping per sequence including pre-determined sequence of orientation (m) in within. n is a variable. n is an integer. n is not equal zero. n<infinity. n represents the length of sequence measured by L-amino acids encoded by codons. n represents the number of amino acids counted from either N-terminal or C-terminal end of a peptide or protein sequence.

(3) Definition of m
Nucleic Acids:
m: number of all codons of pre-determined sequence of orientation per entire sequence of either 5'- or 3'-orientation. For example, if there are no pre-determined sequence of orientation at the beginning per entire sequence of either 5'- or 3'-orientation, m=zero; if a sequence started from adjacent downstream to 5'-ATG in 5'-orientation, m=1; if a sequence started from adjacent upstream to 3'-AGT (5'-TGA) in 3'-orientation, m=1; if a sequence started from adjacent downstream to 5'-GAATTC (EcoR I recognition sequence) in 5'-orientation, m=2; if a sequence started from adjacent downstream to 5'-CACACAGGAGAAAAGCCA (SEQ ID No. 1) (conservative motif of six amino acids of a zinc finger gene family) in 5'-orientation, m=6. m is a variable. m is from zero to n. m≤n. m is an integer.
Peptides:
m: number of all amino acids of pre-determined sequence of orientation per entire sequence of either N-terminal or C-terminal orientation. For example, if there are no the predetermined sequence of orientation at the beginning per entire sequence of either N-terminal or C-terminal orientation, m=zero; if a sequence started from adjacent downstream to an amino acid encoded by a start codon, such as Methionine encoded by 5'-ATG, in N-terminal orientation, m=1; if a sequence started adjacent upstream to from one amino acid encoded by a codon in C-terminal orientation, m=1; if a sequence started from adjacent downstream to N-EF (two amino acids encoded by EcoR I recognition sequence) in N-terminal orientation, m=2; if a sequence started from adjacent downstream to NH$_2$-HTGEFP (SEQ ID No. 2) (conservative motif of six amino acids of zinc finger gene family) in N-terminal orientation, m=6. m is a variable. m is from zero to n. m≤n. m is an integer.

(4) Definition of the Negative Sign

A negative sign in front of codon means that the position of codon is in 5'-UTR.

(5) Definition of Y

Nucleic Acids:

Y is the total number of n-codon-length long sequences. Y represents the total number of sequences of ORF of a given length (n). Y represents the total number of sequences of 5'-UTR of a given length (n). Y represents the total number of sequences of 3'-UTR of a given length (n).

Peptides:

Y is the total number of n-amino-acids-length long sequences. Y represents the total number of sequences of peptide or protein of a given length (n).

(6) Applications

Nucleic Acids:

(a) If X=61 and m=0; Y=61.sup.n

It is applicable to ORF sequences of n-codon-length long between 5'- and 3'-ends.

(b) If X=61, m=1; Y=61.sup.(n−1)

It is applicable to ORF sequences of n-codon-length long oriented by a codon, such as a start codon at 5'-end or a stop codon at 3'-end (The first position of codon at 5'-terminal of ORF sequences could be occupied by a given codon excluding stop codon. Or the first position of codon at 3'-terminal of ORF sequences could be occupied by a given codon including stop codon).

(c) If X=61, n>m, m=2; Y=61.sup.(n−2)

It is applicable to ORF sequences of n-codon-length long oriented by a two-codon restriction enzyme recognition sequence at either 5'-end or 3'-end. The termination codons are specifically excluded.

(d) If X=61, (n−m)>1; Y=61.sup.(n−m)

It is applicable to ORF sequences of n-codon-length long oriented by a pre-determined oriented sequence that consists of m codons at either 5'-end or 3'-end. The termination codons are specifically excluded.

(e) If X=64, m=1, (n−m)>1; Y=64.sup.(1−n)

It is applicable to 5'-UTR sequences of n-codon-length long oriented by a start codon at 3'-end (the last position of codon at 3'-end of 5'-UTR is covalently linked with a start codon, such as 5'-ATG, per sequence).

(f) If X=64, m=1, (n−m)>1; Y=64.sup.(n−1)

It is applicable to 3'-UTR sequences of n-codon-length long oriented by a stop codon at 5'-end (the last position of codon at 5'-end of 3'-UTR is covalently linked with a stop codon, such as 5'-TGA, per sequence).

(g) If X=64, n>m, m=2; Y=64.sup.(n−2)

It is applicable to 5'-UTR sequences of n-codon-length long oriented by a two-codon restriction enzyme recognition sequence at either 5'-end or 3'-end. The termination codons are included. It is applicable to 3'-UTR sequences of n-codon-length long oriented by a two-codon restriction enzyme recognition sequence at either 5'-end or 3'-end. The termination codons are included.

(h) If X=64, (n−m)>1; Y=64.sup.(n−m)

It is applicable to 5'-UTR sequences of n-codon-length long oriented by a pre-determined sequence of orientation that consists of m codons at either 5'-end or 3'-end. The termination codons are included. It is applicable to 3'-UTR sequences of n-codon-length long oriented by a pre-determined sequence of orientation that consists of m codons at either 5'-end or 3'-end. The termination codons are included.

Peptides:

(a) If X=20, n=m or n>m, m=0; Y=20.sup.n

It is applicable to sequences of n-amino-acids-length long at either C-terminal or between N-terminal and C-terminal.

(b) If X=20, n>m, m=1; Y=20.sup.(n−1)

It is applicable to sequences of n-amino-acids-length long oriented by a given amino acid encoded by a codon, such as a Methionine encoded by a start codon at either N-terminal or C-terminal.

(c) If X=20, n>m, m=2; Y=20.sup.(n−2)

It is applicable to sequences of n-amino-acids-lenqth long oriented by two consecutive amino acid encoded by two-codon-restriction-enzyme-recognition sequence at either N-terminal or C-terminal.

(d) If X=20, (n−m)>1; Y=20.sup.(n−m)

It is applicable to sequences of n-amino-acids-length long oriented by m pre-determined amino acids sequence encoded by codons at either N-terminal or C-terminal.

With knowledge of each of the 64 codons and 20 L-amino acids, the inventive universal genetic algorithm of Y=X.sup.(n−m) provides a quantitative vehicle to deduce all possible sequence(s) of either nucleic acid or peptide of a given length. Starting with the universal genetic algorithm, a series of further genetic algorithms have been derived therefrom, as discussed herein. It provides a universal calculation formula for the total number of sequences of either nucleic acids or peptides of a given length measured by either codon or L-amino acid encoded by codon when the orientation direction has been determined. The length measured by codons can convert to the length measured by single nucleotides by multiplying three (×3). The inventive methodologies are codon-based, which selectively exclude nonsense codons that do not exist in the ORF sequence in the designing oligonucleotide sequences. A series of libraries, such as oligonucleotide probe libraries have been established accordingly as presented herein. The said oligonucleotides can be utilized in reactions in aqueous phases, such as RT-PCR, PCR, Touchdown PCR, Real-time PCR, and DD-RT-PCR or on the surface of solid phases, such as DNA Microarrays, Dot and filter hybridizations.

According to a terminology aspect of the invention, wherein $I_S$ represents an initiation codon in sense orientation, wherein $T_S$ represents a termination codon in sense orientation, wherein $C_S$ represents an amino acid coding codon in sense orientation, wherein $V_S$ represents a codon in sense orientation, wherein $R_S$ represents a two codon (six nucleotides) restriction endonuclease recognition site in sense orientation with the proviso that neither of the two codons is a termination codon, wherein $E_S$ represents a two codon (six nucleotides) restriction endonuclease recognition site in sense orientation, wherein oligo-d(T)$_S$ represents a plurality of consecutive thymidine nucleotides, wherein $I_A$ represents an initiation codon in antisense orientation, wherein $T_A$ represents a termination codon in antisense orientation, wherein $C_A$ represents an amino acid coding codon in antisense orientation, wherein $V_A$ represents a codon in antisense orientation, wherein $R_A$ represents a two codon (six nucleotides) restriction endonuclease recognition site in antisense orientation with the proviso that neither of the two codons is a termination codon, wherein $E_A$ represents a two codon (six nucleotides) restriction endonuclease recognition site in antisense orientation, wherein A represents an amino acid, wherein M represents an amino acid encoded by an initiation codon, wherein $R_E$ is one of the amino acid sequences encoded by $R_S$, wherein said universal bases are selected from the group comprising 5'-nitroindole-2'-deoxyriboside, 3-nitropyrrole, inosine, pypoxanthine and combinations thereof.

According to a first aspect of the invention, there is a kit(s) provided for identifying targeting sequences within a sample comprising at least one of the following:

a 5' start codon (sense) panel comprising a plurality of oligonucleotides, wherein each of said oligonucleotides is represented by the formula 5'-$I_S(C_S)_{n1}$-3', wherein n1 represents the length of said $(C_S)_{n1}$ measured by codon, n1 is variable and an integer;

a 5' start codon (antisense) panel comprising a plurality of oligonucleotides, wherein each of the oligonucleotides is represented by the formula 5'-$(C_A)_{n2}I_A$-3', wherein n2 represents the length of said $(C_A)_{n2}$ measured by codon, n2 is variable and an integer;

a 5' UTR (sense) panel comprising a plurality of oligonucleotides, wherein each of the oligonucleotides is represented by the formula 5'-$(V_S)_{n3}I_S$-3', wherein n3 represents the length of said $(V_S)_{n3}$ measured by codon, n3 is variable and an integer;

a 5' UTR (antisense) panel comprising a plurality of oligonucleotides, wherein each of the oligonucleotides is represented by the formula 5'-$I_A(V_A)_{n4}$-3', wherein n4 represents the length of said $(V_A)_{n4}$ measured by codon, n4 is variable and an integer;

a 3' stop codon (sense) panel comprising a plurality of oligonucleotides, wherein each of the oligonucleotides is represented by the formula 5'-$(C_S)_{n5}T_S$-3', wherein n5 represents the length of said $(C_S)_{n5}$ measured by codon, n5 is variable and an integer;

a 3' stop codon (antisense) panel comprising a plurality of oligonucleotides, wherein each of the oligonucleotides is represented by the formula 5'-$T_A(C_A)_{n6}$-3', wherein n6 represents the length of said $(C_A)_{n6}$ measured by codon, n6 is variable and an integer;

a 3' UTR (sense) panel comprising a plurality of oligonucleotides, wherein each of the oligonucleotides is represented by the formula 5'-$T_S(V_S)_{n7}$-3', wherein n7 represents the length of said $(V_S)_{n7}$ measured by codon, n7 is variable and an integer;

a 3' UTR (antisense) panel comprising a plurality of oligonucleotides, wherein each of the oligonucleotides is represented by the formula 5'-$(V_A)_{n8}T_A$-3', wherein n8 represents the length of said $(V_A)_{n8}$ measured by codon, n8 is variable and an integer;

a 5' restriction endonuclease (sense) panel comprising a plurality of oligonucleotides, wherein each of the oligonucleotides is represented by the formula 5'-$R_S(C_S)_{n9}$-3', wherein n9 represents the length of said $(C_S)_{n9}$ measured by codon, n9 is variable and an integer;

a 5' restriction endonuclease (antisense) panel comprising a plurality of oligonucleotides, wherein each of the oligonucleotides is represented by the formula 5'-$(C_A)_{n10}R_A$-3', wherein n10 represents the length of said $(C_S)_{n}10$ measured by codon, n10 is variable and an integer;

a 3' restriction endonuclease (sense) panel comprising a plurality of oligonucleotides, wherein each of the oligonucleotides is represented by the formula 5'-$(C_S)_{n11}R_S$-3', wherein n11 represents the length of said $(C_S)_{n11}$ measured by codon, n11 is variable and an integer;

a 3' restriction endonuclease (antisense) panel comprising a plurality of oligonucleotides, wherein each of the oligonucleotides is represented by the formula 5'-$R_A(C_A)_{n12}$-3', wherein n12 represents the length of said $(C_A)_{n12}$ measured by codon, n12 is variable and an integer;

a 5' restriction endonuclease (sense) panel comprising a plurality of oligonucleotides, wherein each of the oligonucleotides is represented by the formula 5'-$E_S(V_S)_{n13}$-3', wherein n13 represents the length of said $(V_S)_{n13}$ measured by codon, n13 is variable and an integer;

a 5' restriction endonuclease (antisense) panel comprising a plurality of oligonucleotides, wherein each of the oligonucleotides is represented by the formula 5'-$(V_A)_{n14}E_A$-3', wherein n14 represents the length of said $(V_A)_{n14}$ measured by codon, n14 is variable and an integer;

a 3' restriction endonuclease (sense) panel comprising a plurality of oligonucleotides, wherein each of the oligonucleotides is represented by the formula 5'-$(V_S)_{n15}E_S$-3', wherein n15 represents the length of said $(V_S)_{n15}$ measured by codon, n15 is variable and an integer;

a 3' restriction endonuclease (antisense) panel comprising a plurality of oligonucleotides, wherein each of the oligonucleotides is represented by the formula 5'-$E_A(V_A)_{n16}$-3-3', wherein n16 represents the length of said $(V_A)_{n16}$ measured by codon, n16 is variable and an integer;

a between 5' and 3' (sense) panel comprising a plurality of oligonucleotides, wherein each of the oligonucleotides is represented by the formula 5'-$(C_S)_{n17}$-3', wherein n17 represents the length of said $(C_S)_{n17}$ measured by codon, n17 is variable and an integer;

a between 5' and 3' (antisense) panel comprising a plurality of oligonucleotides, wherein each of the oligonucleotides is represented by the formula 5'-$(C_A)_{n18}$-3', wherein n18 represents the length of said $(C_A)_{n18}$ measured by codon, n18 is variable and an integer;

an oligonucleotide panel comprising a plurality of oligonucleotides, wherein each of the said oligonucleotides is represented by the formula 5'-$(C_S)_{n19}$-3', wherein each said oligonucleotide further comprises a linker at either 5'-end or 3'-end of said oligonucleotide, the said linker is an amino acid coding codon in sense orientation, n19 represents the length of said $(C_S)_{n19}$ measured by codon, n19 is variable and an integer;

an oligonucleotide panel comprising a plurality of oligonucleotides, wherein each of the said oligonucleotides is represented by the formula 5'-$(C_S)_{n20}$-3', wherein each said oligonucleotide further comprises a linker at either 5'-end or 3'-end of said oligonucleotide, the said linker is two consecutive amino acid coding codons in sense orientation, n20 represents the length of said $(C_S)_{n20}$ measured by codon, n20 is variable and an integer;

an oligonucleotide panel comprising a plurality of oligonucleotides, wherein each of the said oligonucleotides is represented by the formula 5'-$(C_S)_{n21}$-3', wherein each said oligonucleotide further comprises a linker at either 5'-end or 3'-end of said oligonucleotide, the said linker is three consecutive amino acid coding codons in sense orientation, n21 represents the length of said $(C_S)_{n21}$ measured by codon, n21 is variable and an integer;

an oligonucleotide panel comprising a plurality of oligonucleotides, wherein each of the said oligonucleotides is represented by the formula 5'-$(C_S)_{n22}$-3', wherein each said oligonucleotide further comprises a linker at either 5'-end or 3'-end of said oligonucleotide, the said linker is a codon comprising one universal base, n22 represents the length of said $(C_S)_{n22}$ measured by codon, n22 is variable and an integer;

an oligonucleotide panel comprising a plurality of oligonucleotides, wherein each of the said oligonucleotides is represented by the formula 5'-$(C_S)_{n23}$-3', wherein each said oligonucleotide further comprises a linker at either 5'-end or 3'-end of said oligonucleotide, the said linker is a codon comprising two universal bases, n23 represents the length of said $(C_S)_{n23}$ measured by codon, n23 is variable and an integer;

an oligonucleotide panel comprising a plurality of oligonucleotides, wherein each of the said oligonucleotides is represented by the formula 5'-$(C_S)_{n24}$-3', wherein each said oligonucleotide further comprises a linker at either 5'-end or 3'-end of said oligonucleotide, the said linker is a codon comprising three universal bases, n24 represents the length of said $(C_S)_{n24}$ measured by codon, n24 is variable and an integer;

an oligonucleotide panel comprising a plurality of oligonucleotides, wherein each of the said oligonucleotides is represented by the formula 5'-$(C_A)_{n25}$-3', wherein wherein each said oligonucleotide further comprises a linker at either 5'-end or 3'-end of said oligonucleotide, the said linker is an amino acid coding codon in antisense orientation, n25 represents the length of said $(C_A)_{n25}$ measured by codon, n25 is variable and an integer;

an oligonucleotide panel comprising a plurality of oligonucleotides, wherein each of the said oligonucleotides is represented by the formula 5'-$(C_A)_{n26}$-3', wherein wherein each said oligonucleotide further comprises a linker at either 5'-end or 3'-end of said oligonucleotide, the said linker is two consecutive amino acid coding codons in antisense orientation, n26 represents the length of said $(C_A)_{n26}$ measured by codon, n26 is variable and an integer;

an oligonucleotide panel comprising a plurality of oligonucleotides, wherein each of the said oligonucleotides is represented by the formula 5'-$(C_A)_{n27}$-3', wherein wherein each said oligonucleotide further comprises a linker at either 5'-end or 3'-end of said oligonucleotide, the said linker is three consecutive amino acid coding codons in antisense orientation, n27 represents the length of said $(C_A)_{n27}$ measured by codon, n27 is variable and an integer;

an oligonucleotide panel comprising a plurality of oligonucleotides, wherein each of the said oligonucleotides is represented by the formula 5'-$(C_A)_{n28}$-3', wherein wherein each said oligonucleotide further comprises a linker at either 5'-end or 3'-end of said oligonucleotide, the said linker is a codon comprising one universal base, n28 represents the length of said $(C_A)_{n28}$ measured by codon, n28 is variable and an integer;

an oligonucleotide panel comprising a plurality of oligonucleotides, wherein each of the said oligonucleotides is represented by the formula 5'-$(C_A)_{n29}$-3', wherein wherein each said oligonucleotide further comprises a linker at either 5'-end or 3'-end of said oligonucleotide, the said linker is a codon comprising two universal bases, n29 represents the length of said $(C_A)_{n29}$ measured by codon, n29 is variable and an integer;

an oligonucleotide panel comprising a plurality of oligonucleotides, wherein each of the said oligonucleotides is represented by the formula 5'-$(C_A)_{n30}$-3', wherein wherein each said oligonucleotide further comprises a linker at either 5'-end or 3'-end of said oligonucleotide, the said linker is a codon comprising three universal bases, n30 represents the length of said $(C_A)_{n30}$ measured by codon, n30 is variable and an integer;

an oligonucleotide panel comprising a plurality of oligonucleotides, wherein each of the said oligonucleotides is represented by said formula 5'-$(V_S)_{n31}$-3', wherein each said oligonucleotide further comprising a linker at either 5'-end or 3'-end of said oligonucleotide, the said linker is a codon in sense orientation, n31 represents the length of said $(V_S)_{n31}$ measured by codon, n31 is variable and an integer;

an oligonucleotide panel comprising a plurality of oligonucleotides, wherein each of the said oligonucleotides is represented by said formula 5'-$(V_S)_{n32}$-3', wherein each said oligonucleotide further comprising a linker at either 5'-end or 3'-end of said oligonucleotide, the said linker is two consecutive codons in sense orientation, n32 represents the length of said $(V_S)_{n32}$ measured by codon, n32 is variable and an integer;

an oligonucleotide panel comprising a plurality of oligonucleotides, wherein each of the said oligonucleotides is represented by said formula 5'-$(V_S)_{n33}$-3', wherein each said oligonucleotide further comprising a linker at either 5'-end or 3'-end of said oligonucleotide, the said linker three consecutive codons in sense orientation, n33 represents the length of said $(V_S)_{n33}$ measured by codon, n33 is variable and an integer;

an oligonucleotide panel comprising a plurality of oligonucleotides, wherein each of the said oligonucleotides is represented by said formula 5'-$(V_S)_{n34}$-3', wherein each said oligonucleotide further comprising a linker at either 5'-end or 3'-end of said oligonucleotide, the said linker is a codon comprising one universal base, n34 represents the length of said $(V_S)_{n34}$ measured by codon, n34 is variable and an integer;

an oligonucleotide panel comprising a plurality of oligonucleotides, wherein each of the said oligonucleotides is represented by said formula 5'-$(V_S)_{n35}$-3', wherein each said oligonucleotide further comprising a linker at either 5'-end or 3'-end of said oligonucleotide, the said linker is a codon comprising two universal bases, n35 represents the length of said $(V_S)_{n35}$ measured by codon, n35 is variable and an integer;

an oligonucleotide panel comprising a plurality of oligonucleotides, wherein each of the said oligonucleotides is represented by said formula 5'-$(V_S)_{n36}$-3', wherein each said oligonucleotide further comprising a linker at either 5'-end or 3'-end of said oligonucleotide, the said linker is a codon comprising three universal bases, n36 represents the length of said $(V_S)_{n36}$ measured by codon, n36 is variable and an integer;

an oligonucleotide panel comprising a plurality of oligonucleotides, wherein each of the said oligonucleotides is represented by said formula 5'-$(V_S)_{n37}$oligo-d$(T)_S$-3', wherein the length of said d$(T)_S$ is measured by nucleotide, the said s is variable and an integer, the value of the said s is from 21 to 6, wherein n37 represents the length of said $(V_S)_{n37}$ measured by codon, n37 is variable and an integer;

an oligonucleotide panel comprising a plurality of oligonucleotides, wherein each of the said oligonucleotides is represented by said formula 5'-oligo-d$(T)_S$-3', wherein the length of said d$(T)_S$ is measured by nucleotide, the said s is variable and an integer, the value of the said s is from 21 to 6; and combinations thereof.

According to one said formula, each of the said oligonucleotides of entire length is organized into different sets, each said sets has at least two identical oligonucleotides, the said sets are further organized into different GC identical panels within the specific selections of GC content; wherein each said oligonucleotides of entire length is represented by n, the said n is a variable and integer, the said n represents n1+1, n2+1, n3+1, n4+1, n5+1, n6+1, n7+1, n8+1, n9+2, n10+2, n11+2, n12+2, n13+2, n14+2, n15+2, n16, n17, n18, n19+1, n20+2, n21+3, n22+1, n23+1, n24+1, n25+1, n26+2, n27+3, n28+1, n29+1, n30+1, n31+1 n32+2, n33+3, n34+1, n35+1, n36+1, and n37+s respectively; wherein the said specific selections of GC content are 0%, 16.67%, 33.33%, 50%, 66.67%, 83.33% and 100% when n equals two; wherein the said specific selections of GC content are 0%, 11.11%, 22.22%, 33.33%, 44.44%, 55.56%, 66.67%, 77.78%, 88.89% and 100% when n equals three; wherein the said specific selections of GC content are 0%, 8.33%, 16.67%, 25%, 33.33%, 41.67%, 50%, 58.33%, 66.67%, 75%, 83.33%, 91.67% and 100% when n equals four; wherein the said specific selections of GC content are 0%, 6.67%, 13.33%, 20%, 26.67%, 33.33%, 40%, 46.67%, 53.33%, 60%, 66.67%, 73.33%, 80%, 86.67%, 93.33% and 100% when n equals five; wherein the said specific selections of GC content are 0%, 5.56%, 11.11%, 16.67%, 22.22%, 27.78%, 33.33%, 38.89%, 44.44%, 50%, 55.56%, 61.11%, 66.67%, 72.22%, 77.78%, 83.33%, 88.89%, 94.44% and 100% when n equals six; wherein the said specific selections of GC content are 0%, 4.76%, 9.52%, 14.29%, 19.05%, 23.81%, 28.57%, 33.33%, 38.10%, 42.86%, 47.62%, 52.38%, 57.14%, 61.90%, 66.67%, 71.43%, 76.19%, 80.95%, 85.71%, 90.48%, 95.24% and 100% when n equals seven, wherein the said specific selections of GC content are 0%, 4.17%, 8.33%, 12.50%, 16.67%, 20.83%, 25%, 29.17%, 33.33%, 37.50%, 41.67%, 45.53%, 50%, 54.17%, 58.33%, 62.50%, 66.67%, 70.83%, 75%, 79.17%, 83.33%, 87.50%, 91.67%, 95.83% and 100% when n equals eight (TABLE 18);

each of the said oligonucleotide GC identical panel, wherein each of the said oligonucleotides is represented by a formula selected from a group of formulae described above, wherein each of the said oligonucleotides is immobilized to a solid support in a set of each said oligonucleotide at a specific discrete position to form an oligonucleotide array, the said set comprising at least two copies of the said oligonucleotide, the said oligonucleotide array comprising at least two said sets, the said solid support is silicon or glass or polymers, or plastics or plastic plates or nylon or nitrocellulose filters, polyacrylamide gel pads, beads, for example, streptavidin beads, magnetic beads, micro beads, nanoparticles or other suitable supports known in the art. As will be appreciated by one of skilled in the art, the panels may be used alone or in combination.

According to a second aspect of the invention, there is a kit(s) provided for identifying targeting antibodies within a sample comprising at least one of the following:

a N-terminal restriction endonuclease peptide panel comprising a plurality of peptides, wherein each of the peptides is represented by the formula N-terminal-$R_{E(A)n38}$-C-terminal, wherein n38 represents the length of $(A)_{n38}$ measured by amino acid, n38 is variable and an integer;

a C-terminal restriction endonuclease peptide panel comprising a plurality of peptides, wherein each of the peptides is represented by the formula N-terminal-$(A)_{n39}R_E$-C-terminal, wherein n39 represents the length of $(A)_{n39}$ measured by amino acid, n39 is variable and an integer;

a N-terminal peptide panel comprising a plurality of peptides, wherein each of the peptides is represented by the formula N-terminal-$M(A)_{n40}$-C-terminal, wherein n40 represents the length of $(A)_{n40}$ measured by amino acid, n40 is variable and an integer;

a C-terminal peptide panel comprising a plurality of peptides, wherein each of the peptides is represented by the formula N-terminal-$(A)_{n41}$-C-terminal, wherein n41 represents the length of $(A)_{n41}$ measured by amino acid, n41 is variable and an integer;

a peptide panel comprising a plurality of peptides, wherein each of the peptides is represented by the formula N-terminal-$(A)_{n42}$-C-terminal, wherein each said peptide further comprises a linker at neither N-terminal or C-terminal of said peptide, the said linker being is an amino acid encoded by an initiation codon, wherein n42 represents the length of $(A)_{n42}$ measured by amino acid, n42 is variable and an integer;

a peptide panel comprising a plurality of peptides, wherein each of the peptides is represented by the formula N-terminal-$(A)_{n43}$-C-terminal, wherein each said peptide further comprises a linker at neither N-terminal or C-terminal of said peptide, the said linker being is an amino acid encoded by a codon, wherein n43 represents the length of $(A)_{n43}$ measured by amino acid, n43 is variable and an integer;

a peptide panel comprising a plurality of peptides, wherein each of the peptides is represented by the formula N-terminal-$(A)_{n44}$-C-terminal, wherein each said peptide further comprises a linker at neither N-terminal or C-terminal of said peptide, the said linker being is two consecutive amino acids encoded by two codons, wherein n44 represents the length of $(A)_{n44}$ measured by amino acid, n44 is variable and an integer;

a peptide panel comprising a plurality of peptides, wherein each of the peptides is represented by the formula N-terminal-$(A)_{n45}$-C-terminal, wherein each said peptide further comprises a linker at neither N-terminal or C-terminal of said peptide, the said linker being is two consecutive amino acid deduced from a two codon restriction endonuclease recognition site, wherein n45 represents the length of $(A)_{n45}$ measured by amino acid, n45 is variable and an integer;

a peptide panel comprising a plurality of peptides, wherein each of the peptides is represented by the formula N-terminal-$(A)_{n46}$-C-terminal, wherein each said peptide further comprises a linker at neither N-terminal or C-terminal of said peptide, the said linker being is three two consecutive amino acids encoded by three codons, wherein n46 represents the length of $(A)_{n46}$ measured by amino acid, n46 is variable and an integer; and combinations thereof.

All above said peptides are organized into different sets, each of the said sets has at least two identical peptides or more, wherein each of the said peptides is represented by a formula selected from a group of formulae described above, wherein each of the said peptides is immobilized to a solid support in a set of each said peptide at a specific discrete position to form a peptide array, the said set comprising at least two copies of the said peptide, the said peptide array comprising at least two said sets, the said solid support is silicon or glass or polymers, or plastics or plastic plates or nylon or nitrocellulose filters, polyacrylamide gel pads, beads, for example, streptavidin beads, magnetic beads, micro beads, nanoparticles or other suitable supports known in the art. As will be appreciated by one of skilled in the art, the panels may be used alone or in combination.

According to a third aspect of the invention, there is a kit(s) provided PCR oligonucleotide primer(s) for identifying and amplifying targeting sequences within a sample comprising at least one oligonucleotide selected from the group consisting of:

an oligonucleotide represented by the formula 5'-$I_S(C_S)_{n1}$-3', wherein n1 represents the length of said $(C_S)_{n1}$ measured by codon, n1 is variable and an integer;

an oligonucleotide represented by the formula 5'-$(C_A)_{n2}I_A$-3', wherein n2 represents the length of said $(C_A)_{n2}$ measured by codon, n2 is variable and an integer;

an oligonucleotide represented by the formula 5'-$(V_S)_{n3}I_S$-3', wherein n3 represents the length of said $(V_S)_{n3}$ measured by codon, n3 is variable and an integer;

an oligonucleotide represented by the formula 5'-$I_A(V_A)_{n4}$-3', wherein n4 represents the length of said $(V_A)_{n4}$ measured by codon, n4 is variable and an integer;

an oligonucleotide represented by the formula 5'-$(C_S)_{n5}T_S$-3', wherein n5 represents the length of said $(C_S)_{n5}$ measured by codon, n5 is variable and an integer;

an oligonucleotide represented by the formula 5'-$T_A(C_A)_{n6}$-3', wherein n6 represents the length of said $(C_A)_{n6}$ measured by codon, n6 is variable and an integer;

an oligonucleotide represented by the formula 5'-$T_S(V_S)_{n7}$-3', wherein n7 represents the length of said $(V_S)_{n7}$ measured by codon, n7 is variable and an integer;

an oligonucleotide represented by the formula 5'-$(V_A)_{n8}TA$-3', wherein n8 represents the length of said $(V_A)_{n8}$ measured by codon, n8 is variable and an integer;

an oligonucleotide represented by the formula 5'-$R_S(C_S)_{n9}$-3', wherein n9 represents the length of said $(C_S)_{n9}$ measured by codon, n9 is variable and an integer;

an oligonucleotide represented by the formula 5'-$(C_A)_{n10}R_A$-3', wherein n10 represents the length of said $(C_S)_{n10}$ measured by codon, n10 is variable and an integer;

an oligonucleotide represented by the formula 5'-$(C_S)_{n11}R_S$-3', wherein n11 represents the length of said $(C_S)_{n11}$ measured by codon, n11 is variable and an integer;

an oligonucleotide represented by the formula 5'-$R_A(C_A)_{n12}$-3', wherein n12 represents the length of said $(C_A)_{n12}$ measured by codon, n12 is variable and an integer;

an oligonucleotide represented by the formula 5'-$E_S(V_S)_{n13}$-3', wherein n13 represents the length of said $(V_S)_{n13}$ measured by codon, n13 is variable and an integer;

an oligonucleotide represented by the formula 5'-$(V_A)_{n14}E_A$-3', wherein n14 represents the length of said $(V_A)_{n14}$ measured by codon, n14 is variable and an integer;

an oligonucleotide represented by the formula 5'-$(V_S)_{n15}E_S$-3', wherein n15 represents the length of said $(V_S)_{n15}$ measured by codon, n15 is variable and an integer;

an oligonucleotide represented by the formula 5'-$EA(V_A)_{n16}$-3', wherein n16 represents the length of said $(V_A)_{n16}$ measured by codon, n16 is variable and an integer;

an oligonucleotide represented by the formula 5'-$(C_S)_{n17}$-3', wherein n17 represents the length of said $(C_S)_{n17}$ measured by codon, n17 is variable and an integer;

an oligonucleotide represented by the formula 5'-$(C_A)_{n18}$-3', wherein n18 represents the length of said $(C_A)_{n18}$ measured by codon, n18 is variable and an integer;

an oligonucleotide represented by the formula 5'-$(C_S)_{n19}$-3', wherein each said oligonucleotide further comprises a linker at either 5'-end or 3'-end of said oligonucleotide, the said linker is an amino acid coding codon in sense orientation, n19 represents the length of said $(C_S)_{n19}$ measured by codon, n19 is variable and an integer;

an oligonucleotide represented by the formula 5'-$(C_S)_{n20}$-3', wherein each said oligonucleotide further comprises a linker at either 5'-end or 3'-end of said oligonucleotide, the said linker is two consecutive amino acid coding codons in sense orientation, n20 represents the length of said $(C_S)_{n20}$ measured by codon, n20 is variable and an integer;

an oligonucleotide represented by the formula 5'-$(C_S)_{n21}$-3', wherein each said oligonucleotide further comprises a linker at either 5'-end or 3'-end of said oligonucleotide, the said linker is three consecutive amino acid coding codons in sense orientation, n21 represents the length of said $(C_S)_{n21}$ measured by codon, n21 is variable and an integer;

an oligonucleotide represented by the formula 5'-$(C_S)_{n22}$-3', wherein each said oligonucleotide further comprises a linker at either 5'-end or 3'-end of said oligonucleotide, the said linker is a codon comprising one universal base, n22 represents the length of said $(C_S)_{n22}$ measured by codon, n22 is variable and an integer;

an oligonucleotide represented by the formula 5'-$(C_S)_{n23}$-3', wherein each said oligonucleotide further comprises a linker at either 5'-end or 3'-end of said oligonucleotide, the said linker is a codon comprising two universal bases, n23 represents the length of said $(C_S)_{n23}$ measured by codon, n23 is variable and an integer;

an oligonucleotide represented by the formula 5'-$(C_S)_{n24}$-3', wherein each said oligonucleotide further comprises a linker at either 5'-end or 3'-end of said oligonucleotide, the said linker is a codon comprising three universal bases, n24 represents the length of said $(C_S)_{n24}$ measured by codon, n24 is variable and an integer;

an oligonucleotide represented by the formula 5'-$(C_A)_{n25}$-3', wherein wherein each said oligonucleotide further comprises a linker at either 5'-end or 3'-end of said oligonucleotide, the said linker is an amino acid coding codon in antisense orientation, n25 represents the length of said $(C_A)_{n25}$ measured by codon, n25 is variable and an integer;

an oligonucleotide represented by the formula 5'-$(C_A)_{n26}$-3', wherein wherein each said oligonucleotide further comprises a linker at either 5'-end or 3'-end of said oligonucleotide, the said linker is two consecutive amino acid coding codons in antisense orientation, n26 represents the length of said $(C_A)_{n26}$ measured by codon, n26 is variable and an integer;

an oligonucleotide represented by the formula 5'-$(C_A)_{n27}$-3', wherein wherein each said oligonucleotide further comprises a linker at either 5'-end or 3'-end of said oligonucleotide, the said linker is three consecutive amino acid coding codons in antisense orientation, n27 represents the length of said $(C_A)_{n27}$ measured by codon, n27 is variable and an integer;

an oligonucleotide represented by the formula 5'-$(C_A)_{n28}$-3', wherein wherein each said oligonucleotide further comprises a linker at either 5'-end or 3'-end of said oligonucleotide, the said linker is a codon comprising one universal base, n28 represents the length of said $(C_A)_{n28}$ measured by codon, n28 is variable and an integer;

an oligonucleotide represented by the formula 5'-$(C_A)_{n29}$-3', wherein wherein each said oligonucleotide further comprises a linker at either 5'-end or 3'-end of said oligonucleotide, the said linker is a codon comprising two universal bases, n29 represents the length of said $(C_A)_{n29}$ measured by codon, n29 is variable and an integer;

an oligonucleotide represented by the formula 5'-$(C_A)_{n30}$-3', wherein wherein each said oligonucleotide further comprises a linker at either 5'-end or 3'-end of said oligonucleotide, the said linker is a codon comprising three universal bases, n30 represents the length of said $(C_A)_{n30}$ measured by codon, n30 is variable and an integer;

an oligonucleotide represented by the formula 5'-$(V_S)_{n31}$-3', wherein each said oligonucleotide further comprising a linker at either 5'-end or 3'-end of said oligonucleotide, the said linker is a codon in sense orientation, n31 represents the length of said $(V_S)_{n31}$ measured by codon, n31 is variable and an integer;

an oligonucleotide represented by the formula 5'-$(V_S)_{n32}$-3', wherein each said oligonucleotide further comprising a linker at either 5'-end or 3'-end of said oligonucleotide, the said linker is two consecutive codons in sense orientation, n32 represents the length of said $(V_S)_{n32}$ measured by codon, n32 is variable and an integer;

an oligonucleotide represented by the formula 5'-$(V_S)_{n33}$-3', wherein each said oligonucleotide further comprising a linker at either 5'-end or 3'-end of said oligonucleotide, the said linker three consecutive codons in sense orientation, n33 represents the length of said $(V_S)_{n33}$ measured by codon, n33 is variable and an integer;

an oligonucleotide represented by the formula 5'-$(V_S)_{n34}$-3', wherein each said oligonucleotide further comprising a linker at either 5'-end or 3'-end of said oligonucleotide, the said linker is a codon comprising one universal base, n34 represents the length of said $(V_S)_{n34}$ measured by codon, n34 is variable and an integer;

an oligonucleotide represented by the formula 5'-$(V_S)_{n35}$-3', wherein each said oligonucleotide further comprising a linker at either 5'-end or 3'-end of said oligonucleotide, the said linker is a codon comprising two universal bases, n35 represents the length of said $(V_S)_{n35}$ measured by codon, n35 is variable and an integer;

an oligonucleotide represented by the formula 5'-$(V_S)_{n36}$-3', wherein each said oligonucleotide further comprising a linker at either 5'-end or 3'-end of said oligonucleotide, the said linker is a codon comprising three universal bases, n36 represents the length of said $(V_S)_{n36}$ measured by codon, n36 is variable and an integer;

an oligonucleotide represented by the formula 5'-oligo-d$(T)_S$-3', wherein the length of said d$(T)_S$ is measured by nucleotide, the said s is variable and an integer, the value of the said s is from 21 to 6; and combinations thereof.

According to a fourth aspect of the invention, there is a method(s) of generating and amplifying a cDNA library provided comprising:

admixing an mRNA sample containing a plurality of different mRNA molecules with an oligonucleotide library, wherein each of the oligonucleotides is represented by the formula 5'-$(C_s)_{n1}$-3' alone, or with an oligonucleotide library, wherein each of the oligonucleotides is represented by the formula 5'-$I_s(C_s)_{n1}$-3' alone, or with an oligonucleotide library, wherein each of the oligonucleotides is represented by the formula oligo-d$(T)_s$ alone or and combinations thereof;

incubating said mRNA, said oligonulceotides and said oligo-d$(T)_s$ in the presence of reagents needed for reverse transcription under conditions suitable for mRNA reverse transcription, thereby producing first stands of a cDNA library; and incubating the said first stands of the cDNA library in the presence of reagents needed for cDNA synthesis under conditions suitable for cDNA synthesis, thereby producing double stranded of a cDNA library; and incubating the said double stranded cDNA library with each of the said oligonulceotides and oligo-d$(T)_s$ in each respective single-container, such as a plastic single-tube in the presence of reagents needed for PCR DNA amplification under conditions suitable for each respective PCR DNA amplification, collecting all respective single-containers after incubation, thereby producing a PCR amplified cDNA library; and isolating each of the said cDNA molecules of each of the said PCR amplified cDNA library in the presence of reagents needed for cDNA molecules isolation under conditions suitable for cDNA molecules isolation; and cloning each of the said cDNA molecules into an appropriate DNA vector in the presence of reagents needed for cDNA molecules cloning under conditions suitable for cDNA molecules cloning; and amplifying each of the said DNA vector containing each said cDNA molecules in each respective single-container in the presence of reagents needed for DNA vector amplification under conditions suitable for DNA vector amplification, collecting all respective single-containers after amplifying, thereby producing a DNA vector amplified cDNA library, the said DNA vector amplified cDNA library contains the said cDNA molecules.

According to a fifth aspect of the invention, there is a method(s) of preparing a cDNA array provided comprising:

Each of the said cDNA molecules obtained according to above a fourth aspect of the invention, wherein each of the said cDNA molecules is immobilized to a solid support in a set of each said cDNA molecule at a specific discrete position to form a cDNA array, the said set comprising at least two copies of the said cDNA molecule, the said cDNA array comprising at least two said sets, the said solid support is silicon or glass or polymers, or plastics or plastic plates or nylon or nitrocellulose filters, polyacrylamide gel pads, beads, for example, streptavidin beads, magnetic beads, micro beads, nanoparticles or other suitable supports known in the art.

According to a sixth aspect of the Invention, there is an electronic database panel(s) provided comprising a plurality of oligonucleotide sequences wherein each of the oligonucleotide sequences is represented by a formula selected from a group of formulae comprising: 5'-$I_S(C_S)_{n1}$-3', 5'-$(C_A)_{n2}I_A$-3', 5'-$(V_S)_{n3}I_S$-3', 5'-$I_A(V_A)_{n4}$-3', 5'-$(C_S)_{n5}T_S$-3', 5'-$T_A(C_A)_{n6}$-3', 5'-$T_S(V_S)_{n7}$-3', 5'-$(V_A)_{n8}T_A$-3', 5'-$R_S(C_S)_{n9}$-3', 5'-$(C_A)_{n10}R_A$-3', 5'-$(C_S)_{n11}R_S$-3', 5'-$R_A(C_A)_{n12}$-3', 5'-$E_S(V_S)_{n13}$-3', 5'-$(V_A)_{n14}E_A$-3', 5'-$(V_S)_{n15}E_S$-3', 5'-$(V_S)_{n15}E_S$-3', 5'-$EA(V_A)_{n16}$-3', 5'-$(C_S)_{n17}$-3', 5'-$(C_A)_{n18}$-3', and combinations thereof; each of the said oligonucleotide sequences has at the least one computer readable annotation, each of the said oligonucleotides sequences could be used as a "query sequence" in the search against the said database, each of the said oligonucleotides sequences could be represented or displayed in a word processing file, wherein the said file is Microsoft Word or ASCII file stored in a database application, wherein the said database is Sybase or Oracle or DB2 or other suitable database known in the art; and the said electronic database panel(s) is accessible via computer readable media comprising CD-ROM, floppy discs, hard disc storage medium and other suitable media known in the art; and the said electronic database panel(s) could also be accessed online via Internet. As will be appreciated by one of skilled in the art, the panels may be used alone or in combination.

According to a seven aspect of the invention, there is an electronic database panel(s) provided comprising a plurality of peptide sequences wherein each of the peptide sequences is represented by a formula selected from a group of formulae comprising: N-terminal-$R_E(A)_{n38}$-C-terminal, N-terminal-$(A)_{n39}R_E$-C-terminal, N-terminal-M$(A)_{n40}$-C-terminal, N-terminal-$(A)_{n41}$-C-terminal, and combinations thereof; each of the said peptide sequences has at the least one computer readable annotation, each of the said peptides sequences could be used as a "query sequence" in the search against the said database, each of the said peptides sequences could be represented or displayed in a word processing file, wherein the said file is Microsoft Word or ASCII file stored in a database application, wherein the said database is Sybase or Oracle or DB2 or other suitable database known In the art; and the said electronic database panel(s) is accessible via computer readable media comprising CD-ROM, floppy discs, hard disc storage medium and other suitable media known in the art; and the said electronic database panel(s) could also be accessed online via Internet. As will be appreciated by one of skilled in the art, the panels may be used alone or in combination.

As will be appreciated by one of skilled in the art, n1 to n46 individually may be any positive, non-zero integer. That is, within a given kit or panel, n1 may be 3 and n2 may be 2; alternatively, for example, both n1 and n2 may be 2. In other embodiments, n1 to n46 may individually be an Integer from 1-8, from 1-7, from 1-6, from 1-5 or from 1-4.

As will be appreciated by one of skilled in the art, a given single panel may consist of 2 or more sets of oligonucleotides or of peptides of one of the above-described formulae; 5 or more sets of oligonucleotides or of peptides of one of the above-described formulae; 10 or more sets of oligonucleotides or of peptides of one of the above-described formulae; 15 or more sets of oligonucleotides or of peptides of one of the above-described formulae; 20 or more sets of oligonucleotides or of peptides of one of the above-described formulae; 25 or more sets of oligonucleotides or of peptides of one of the above-described formulae; or 50 or more sets of oligonucleotides or of peptides of one of the above-described formulae; 100 or more sets of oligonucleotides or of peptides of one of the above-described formulae; or 200 or more sets of oligonucleotides or of peptides of one of the above-described formulae; 300 or more sets of oligonucleotides or of peptides of one of the above-described formulae; or 500 or more sets of oligonucleotides or of peptides of one of the above-described formulae; 1,000 or more sets of oligonucleotides or of peptides of one of the above-described formulae; or 2,000 or more sets of oligonucleotides or of peptides of one of the above-described formulae; 3,000 or more sets of oligonucleotides or of peptides of one of the above-described formulae; or 5,000 or more sets of oligonucleotides or of peptides of one of the above-described formulae; 10,000 or more sets of oligonucleotides or of peptides of one of the above-described formulae; or 20,000 or more sets of oligonucleotides or of peptides of one of the above-described formulae; 50,000 or more sets of oligonucleotides or of peptides of one of the above-described formulae; or 100,000 or more sets of oligonucleotides or of peptides of one of the above-described formulae; 200,000 or more sets of oligonucleotides or of peptides of one of the above-described formulae; or 500,000 or more sets of oligonucleotides or of peptides of one of the above-described formulae: and in one preferred embodiment, the said GC Identical Panels could be further sub-classified according to GC content after the incorporation of LNA. In another preferred embodiment, the Tm of the said GC Identical Panels could be further adjusted by the incorporation of appropriate number of LNA. In yet other embodiments, a panel may comprise substantially all of the oligonucleotides or peptides of one of the above-described formulae. In other embodiments of the invention, each oligonucleotide or peptide of the panel may consist essentially of an oligonucleotide or peptide according to the specific formula for the respective panel, as discussed herein and hereinafter.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

"Oligonucleotide" refers to polymeric forms of nucleotides of a given length of a given single-stranded nucleic acid molecule. As used herein, the length of oligonucleotide is preferably measured by codon. In general, the length is at least one codon long, or preferably at least two, three, four, five, six, seven, eight, nine or ten codons long but preferably no more than ten codons long. It includes deoxyribonucleotides, ribonucleotides and their corresponding analogs and derivatives thereof. For example, Locked Nucleic Acid (LNA), Peptide Nucleic Acid (PNA) and Universal base belong to the said analogs and derivatives. Oligonucleotides include all formats of chemical modifications which are both on and in between of nucleotides within a given oligonucleotide. For example, methylation of the naturally occurring nucleotides and analogs is a format of chemical modifications. Modifications of internucleotide linkages, for example but by no means limited to methyl phosphonates, phosphoroamidites, phosphotriesters, phosphorothioates, phosphorodithioates and the like are included. Oligonucleotides may be labelled with radio isotopes, for example, $.^{32}P$ or $.^{33}P$ or $.^{35}S$. Alternatively oligonucleotides may be labelled with other molecules that provide a detectable signal, either directly or indirectly, for example but by no means limited to fluorescent dyes and biotin.

"Panel" refers to a plurality of reagents, for example, oligonucleotides or peptides. The panel may be immobilized to or on a suitable solid support. Suitable solid supports include but are by no means limited to silicon, glass, polymers, plastics, plastic plates, nylon or nitrocellulose filters, polyacrylamide gel pads, beads, for example, streptavidin beads, magnetic beads, micro beads, nanoparticles and the like. While the singular form is used, a panel may comprise a single library immobilized to several separate suitable solid supports. As will be appreciated by one of skill in the art, when the panel includes a suitable solid support, the oligonucleotides or peptides may be immobilized directly to a suitable solid support or an activated surface of a suitable solid support or may be linked by a suitable linker to a suitable solid support as known in the art. The entire panel or individual oligonucleotides or peptides thereof may be in a substantially aqueous phase.

"Set" refers to an organizational format for a plurality of reagents, such as oligonucleotides or peptides on a panel. Each set has at least two copies of a oligonucleotide or at least two copies of a peptides. Usually, each set possesses at least more than two copies of an oligonucleotide or more than two copies of a peptide. In some embodiments, each of the said set may have at least two copies of one distinctive oligonulceotide or peptide. In some embodiments, each of the said distinctive oligonucleotide or peptide in a set has the identical length. In some embodiments, all the said distinctive oligonucleotides or peptides of all the sets of the entire panel may have the identical length. In other embodiments, all the said distinctive oligonucleotides or peptides of all the sets of the entire panel may have both the identical length and GC content.

"GC Identical Panel" refers to a format of an oligonucleotide panel. The GC identical Panel consists of sets of oligonucleotides that are all identical in GC content. In one preferred embodiment, none of the oligonulceotide sequences of a set are identical to other sets within a given panel; but the said oligonulceotide sequences are all identical in GC content in each set within a panel. In another preferred embodiment, none of the oligonulceotide sequences of a set are identical to other sets within a given panel, but the said oligonulceotide sequences are all identical In GC content and length in each set within a panel.

"Genetic signature" refers to a biological characteristic of, for example, a gene, mRNA, peptide, an ORF sequence, a nucleic acid sequence, a peptide sequence, antigen, antibody, cell, cell line, tissue, organ, individual or organism. Examples of genetic signatures include but are by no means limited to locations and the immediate adjacent regions of start and stop codons within a gene, locations and the immediate adjacent regions of restriction enzyme sites within a gene, locations and the immediate adjacent regions of promoter sequences within a gene, presence of antigens of a specific amino acid sequence, presence of antibodies recognizing a specific amino acid sequence in a sample, expression pattern(s) or expression fingerprint(s) or expression profile(s) of mRNA(s), cDNA(s), gene(s), genome, peptide(s), Protein(s), cell(s), cell line(s) and the like.

"Hybridization" refers to an interaction between two strands of nucleic acids by hydrogen bonds in accordance with the rules of Watson-Crick DNA complementarity, Hoogstein binding, or other sequence-specific binding known in the art. Hybridization can be performed under different stringent conditions known in the art. Under appropriate stringent conditions, hybridization between the two complementary strands could reach 60% or above, 70% or above, 80% or above, 90% or above in the reactions.

"Substantially all" refers to the fact that a sufficient number of individuals or sets or groups or panels are present that the desired result can be obtained or determined. For example, regarding the use of an oligonucleotide library, "substantially all" members of a specific formula means that enough of the respective oligonucleotides represented by the specific formula are present in the library such that it is a reasonable prediction that the desired result will be obtained. Examples of suitable desired results are discussed in detail herein. As will be appreciated by one of skill in the art, the exact value of "substantially all" is context dependent and will of course depend on many factors, such as how the library is being used, the length of the peptides or oligonucleotides, the GC content and Tm of oligonucleotides, the way of Tm adjustment and how the material being screened as well as other factors. "Substantially all" may be for example 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 99.99% of the oligonucleotides or peptides represented by a specific formula.

"Consisting essentially of" means that the described molecules consist of those nucleotides or peptides as described in the formulae listed as well as other components which are in the scope and spirit of the invention. In the case of the oligonucleotides, examples include but are by no means limited to oligonucleotides containing Universal base or Locked Nucleic Acid (LNA) or Peptide Nucleic Acid (PNA), as described herein.

"Discrete" in regards the positioning of a peptide or oligonucleotide on a support refers to the fact that the oligonucleotide or peptide or set thereof is positioned such that a signal therefore can be detected unambiguously. As will be appreciated by one of skilled in the art, what is and isn't a discrete position will depend largely on the reporting signal used, the platform and the detection method as well as other factors well known to one of skilled in the art.

"Plurality" refers to 2 or more.

"Strands of the Double Helix of Nucleic Acids" means that there are two strands of each helix of a nucleic acid molecule: Sense strand (non-template strand or coding strand) and antisense strand (template strand or non-coding strand).

"Orientation" refers to two orientations of each single strand of nucleic acids: 5'-towards-3' and 3'-towards-5'. It also refers to two orientations of each peptide sequence: N-terminal towards C-terminal and C-terminal towards N-terminal.

"Any codon" refers to any one of the 64 nucleotide triplets of the genetic code.

"Sense" orientation or strand refers to the coding strand or the complementary strand of the non-coding strand or the complementary strand of the antisense strand or the non-template strand of a double stranded DNA molecule.

"Antisense" orientation or strand refers to the non-coding strand or complementary strand of the coding strand or complementary strand of the sense strand or the template strand of a double-stranded DNA molecule.

"Amino acid coding codon" refers to a codon of a given genetic code encoding for an amino acid. In most cases, 61 codons code for the 20 essential amino acids. As an example, in one genetic code, in sense orientation, 5'-AGG codes for arginine. The said genetic code in antisense orientation codon is 5'-CCT.

"Initiation codon" refers to a codon that may function as the start codon. In most cases, the initiation codon in sense orientation is 5'-ATG; the initiation codon in antisense orientation is 5'-CAT. As discussed herein, other initiation codons may be used in the invention, for example, 5'-ATA, which is the start codon in mammalian mitochondria. Other initiation codons include but are by no means limited to 5'-GTG, 5'-ATA, 5'-TTG, 5'-ACG and 5'-CTG.

"Termination codon" refers to a codon that may function as the stop codon. In most cases, there are three dominant stop codons in sense orientation: 5'-TAA, 5'-TGA and 5'-TAG. There are three dominant stop codons in antisense orientation: 5'-TTA, 5'-TCA and 5'-CTA.

"Locked Nucleic Acid" refers to but is by no means limited to an oligonucleotide that contains one or more 2'-O, 4'-methylene-beta-D-robofuranosyl nucleotide monomer(s) which is a member of Locked Nucleic Acid (LNA) family. LNA is water soluble. It possesses increasing thermal stability, mismatch discriminating capacity and high affinity towards complementary DNA and RNA molecules. It improves the performance of short PCR primer and oligonucleotide probe significantly.

"Universal base" refers to molecules capable of substituting for binding to any one of A, C, G, T and U in nucleic acids by forming hydrogen bonds without significant structure destabilization. The oligonucleotide incorporated with the universal base analogues is able to function as a probe in hybridization, as a primer in PCR and DNA sequencing. Examples of universal bases include but are by no means limited to 5'-nitroindole-2'-deoxyriboside, 3-nitropyrrole, inosine and pypoxanthine.

"Oligo-d(T)$_s$" refers to a plurality of consecutive thymidine nucleotides represented by the formula 5'-oligo-d(T)$_s$-3', wherein the length of said d(T)$_s$ is measured by nucleotide, the said s is a variable and integer, the value of the said s is from 21 to 6.

I. Constructions of Standardized Universal Library

Each of the distinct polydeoxyoligonucleotides or polyoligonucleotides thereafter of a given length which was measured and quantified by the number of codons are linear polymers of molecules covalently joined by deoxynucleotides or nucleotides respectively. Each of the distinct deoxyoligonucleotides is covalently joined together with each other by phosphodiester bonds between 3'-hydroxyl group of the preceding nucleotide and 5'-phosphate group of the immediately adjacent nucleotide in 5' towards 3' orientation. The same is true for the oligonucleotides.

Each of the distinct polydeoxyoligonucleotides or polyoligonucleotides thereafter of a given length which was measured and quantified by the number of codons is translated into peptide sequences which consist of L-amino acids respectively. Each of the distinct L-amino acid of the translated peptides is covalently joined together with each other by peptide bonds between carboxylic acid groups of the preceding amino acid and amino groups of the immediately adjacent amino acid in N-terminal towards C-terminal orientation.

Each of the distinct translated peptides thereafter is used as a distinct antigen in the production of the primary specific monoclonal or multiclonal antibodies respectively. Each of the distinct monoclonal or multiclonal antibodies produced by using each distinct translated peptide is used as a distinct antigen in the production of the secondary specific monoclonal and multiclonal antibodies respectively.

1. The Series Standardized Universal ORF Sense Oligonucleotide Libraries with 5'-End Start Codon Orientation For example, at each 5' end of the most ORF sequences, 5'-ATG occupies the first codon position which orients the entire ORF sequence from 5' end towards 3' end. The second codon position in the succession of ORF sequence is occupied by one of the 61 codons (TABLE 1). The third codon position in the succession of the ORF sequence is occupied by one of the 61 codons as well as each of the subsequent sequential codon positions in 5' end towards 3' end orientation thereafter (TABLE 7). The numbers of the distinctive 5'-ATG oriented ORF sequences increase quantitatively with increasing length. The said numbers could be calculated as long as the specific length (n) and (m) were given according to algorithm of $61^{(n-m)}$. In one embodiment, 9 mers 5'-ATG oriented ORF sequence is three-codon length long. 5'-ATG is the pre-determined one-codon length long oriented sequence. Therefore, n=3, m=1, E=n−m. E is exponent. $61^{(3-1)}$=3,721. The total numbers of distinctive 9 mers 5'-ATG oriented ORF sequences are 3,721(TABLE 17). The $n^{th}$ codon occupies the nucleotide positions (3n−2) to (3n) in 5'-ATG oriented n-codon length long sequence (TABLE 7). Each of the nucleotide positions of the $n^{th}$ codon in 5'-oriented triplet format is (3n−2), (3n−1) and (3n) respectively.

In one preferred embodiment, a collection of all the 3,721 distinctive 9 mers 5'-ATG oriented ORF sequences has formed a standardized universal 9 mers oligonucleotide library, which is capable to be used as a standardized universal and all-purpose 9 mers oligonucleotide probe and primer library.

2. The Series Standardized Universal ORF Sense Oligonucleotide Libraries with 3'-End Stop Codon Orientation As discussed above, there are three major stop codons (5'-TAA, 5'-TGA, 5'-TAG). Only one stop codon is at 3'-end of a given ORF sequence. In a given ORF, For example, one stop codon (5'-TGA) at 3' end occupies the first codon position which orients the entire ORF sequence from 3' end to 5' end. The second codon position in the succession of the ORF sequence is occupied by one of the 61 codons (TABLE 1). The third codon position in the succession of the ORF sequence is occupied by one of the 61 codons as well as each of the subsequent sequential codon positions in 3' end towards 5' end orientation thereafter (TABLE 8). The numbers of the distinctive 5'-TGA oriented ORF sequences increase with increasing length. The said numbers could be calculated as long as the specific length (n) and (m) were given according to algorithm of $61^{(n-m)}$. In one embodiment, 9 mers 5'-TGA oriented ORF sequence is three-codon length long. 5'-TGA is the pre-determined one-codon length long oriented sequence. Therefore, n=3, m=1, E=n−m. E is exponent. $61^{(3-1)}$=3,721. The total numbers of distinctive 9 mers 5'-TGA oriented ORF sequences are 3,721(TABLE 17). The $n^{th}$ codon occupies nucleotide positions (3n) to (3n−2) in 5'-TGA oriented n-codon length long sequence (TABLE 8). Each of the nucleotide positions of the $n^{th}$ codon in 5'-oriented triplet format is (3n), (3n−1) and (3n−2) respectively. Thus, the total numbers of distinctive 9 mers 5'-TGA oriented sequences are 3,721. The total numbers of distinctive 9 mers 5'-TAG oriented sequences are 3,721. The total numbers of distinctive 9 mers 5'-TAA oriented sequences are 3,721.

In one preferred embodiment, a collection of all the above distinctive 9 mers stop codon oriented sequences (3,721. times. 3) has formed a standardized universal 9 mers oligonucleotide library, which can be used as a standardized, universal and all-purpose 9 mers oligonucleotide probe and primer library.

3. The Series Standardized Universal ORF Sense Oligonucleotide Libraries of Restriction Endonuclease Recognition Sequence of Two-Codon Orientations The restriction endonuclease recognition sequence of two-codons is selected from the group of restriction endonucleases, without limiting the generality of the foregoing, which exclude any and all stop codons within the recognition sequence comprising: Aat II, Acc65 I, Acl I, Afe I, Afl II, Age I, Apa I, ApaL I, Ase I, Avr II, BamHI, BfrBI, Bgl II, Bmel580 I, BmgB I, BseY I, Btr I, BsiW I, BspD I, BspE I, BsrB I, BsrG I, BssH II, BssS I, Bst B I, BstZ17 I, Cla I, Dra I, Eag I, EcoR I, EcoR V, Fsp I, Hind III, Hpa I, Kas I, Kpn I, Mfe I, Mlu I, Msc I, Nae I, Nar I, Nco I, Nde I, NgoM IV, Nhe I, Nru I, Nsi I, PaeR7 I, Pci I, Pml I, PspOM I, Pst I, Pvu I Pvu II, Sac I, Sac II, Sal I, Sca I, Sfo I, Sma I, SnaB I, Spe I, Sph I, Ssp I, Stu I, Tli I, Xba I, Xho I, Xma I, Acc I, BsaW I, BsiHKA I, Bsp1286 I, MspAl I, Sty I (TABLE 5).

The excluded restriction endonucleases with two-codon recognition sequence are Bcl I, BspH I and Psi I.

(a) The Series Standardized Universal ORF Sense Oligonucleotide Libraries of Restriction Endonuclease Recognition Sequence of Two-Codon with 5'-Orientation For example, 5'-GACGTC is the two-codon recognition sequence of Aat II. At each 5' end of ORF sequence, 5'-GACGTC occupies the consecutive first and second codon positions which orient the entire ORF sequence from 5' end towards 3' end. The third codon position in the succession of the ORF sequence is occupied by one of the 61 codons (TABLE1). The fourth codon position in the succession of the ORF sequence is occupied by one of the 61 codons as well as each of the subsequent sequential codon positions in 5' end towards 3' end orientation thereafter. The numbers of the distinctive 5'-GACGTC oriented ORF sequences increase quantitatively to the length increasing. The said numbers could be calculated as long as the specific length (n) and (m) were given according to algorithm of $61^{(n-m)}$. In one embodiment, 12 mers 5'-GACGTC oriented ORF sequence is four-codon length long. 5'-GACGTC is the pre-determined two-codon length long oriented sequence. Therefore, n=4, m=2, E=n−m. E is exponent. $61^{(4-2)}$=3,721. The total numbers of distinctive 12 mers 5'-GACGTC oriented ORF sequences are 3,721. The $n^{th}$ codon occupies the nucleotide positions (3n−2) to (3n) in 5'-GACGTC oriented n-codon length long sequence. Each of the nucleotide positions of the $n^{th}$ codon in 5'-oriented triplet format is (3n−2), (3n−1) and (3n) respectively.

In one preferred embodiment, a collection of all the 3,721 distinctive 12 mers 5'-GACGTC oriented ORF sequences has formed a standardized universal 12 mers oligonucleotide library, which is capable to be used as a standardized, universal and all-purpose 12 mers oligonucleotide probe and primer library.

(b) The Series Standardized Universal ORF Sense Oligonucleotide Libraries of Restriction Endonuclease Recognition Sequence of Two-Codon with 3'-Orientation For example, 5'-GACGTC is the two-codon recognition sequence of Aat II. At each 3' end of ORF sequence, 5'-GACGTC occupies the consecutive first and second codon positions which orient the entire ORF sequence from 3' end towards 5' end. The third codon position in the succession of the ORF sequence is occupied by one of the 61 codons (TABLE1). The fourth codon position in the succession of the ORF sequence is occupied by one of the 61 codons as well as each of the subsequent sequential codon positions in 3' end towards 5' end orientation thereafter. The numbers of the distinctive 5'-GACGTC oriented ORF sequences increase with increasing length. The said numbers could be calculated as long as the specific length (n) and (m) were given according to algorithm of $61^{(n-m)}$. In one embodiment, 12 mers 5'-GACGTC oriented ORF sequence is four-codon length long. 5'-GACGTC is the pre-determined two-codon length long oriented sequence. Therefore, n=4, m=2, E=n−m. E is exponent. $61^{(4-2)}=3,721$. The total numbers of distinctive 12 mers 5'-GACGTC oriented ORF sequences are 3,721. The $n^{th}$ codon occupies the nucleotide positions (3n) to (3n−2) in 5'-GACGTC oriented n-codon length long sequence. Each of the nucleotide positions of the $n^{th}$ codon in 5'-oriented triplet format is (3n), (3n−1) and (3n−2) respectively.

In one preferred embodiment, a collection of all the 3,721 distinctive 12 mers 5'-GACGTC oriented ORF sequences has formed a standardized universal 12 mers oligonulceotide library, which is capable to be used as a standardized, universal and all-purpose 12 mers oligonulceotide probe and primer library.

4. The Series Standardized Universal 5'-UTR and 3'-UTR Sense Oligonucleotide Libraries of Restriction Endonuclease Recognition Sequence of Two-Codon Orientations The restriction endonuclease recognition sequence of two-codons is selected from the group of restriction endonucleases, without limiting the generality of the foregoing, which include any and all stop codons within the recognition sequence comprising: Aat II, Acc65 I, Acl I, Afe I, Afl II, Age I, Apa I, ApaL I, Ase I, Avr II, BamHI, BfrBI, Bgl II, Bmel580 I, BmgB I, BseY I, Btr I, BsiW I, BspD I, BspE I, BsrB I, BsrG I, BssH II, BssS I, Bst B I, BstZ17 I, Cla I, Dra I, Eag I, EcoR I, EcoR V, Fsp I, Hind III, Hpa I, Kas I, Kpn I, Mfe I, Mlu I, Msc I, Nae I, Nar I, Nco I, Nde I, NgoM IV, Nhe I, Nru I, Nsi I, PaeR7 I, Pci I, Pml I, PspOM I, Pst I, Pvu I Pvu II, Sac I, Sac II, Sal I, Sca I, Sfo I, Sma I, SnaB I, Spe I, Sph I, Ssp I, Stu I, Tli I, Xba I, Xho I, Xma I, Acc I, BsaW I, BsiHKA I, Bsp1286 I, MspAl I, Sty I, Bcl I, BspH I and Psi I (TABLE 6).

(a) The Series Standardized Universal 5'-UTR and 3'-UTR Sense Oligonucleotide Libraries of Restriction Endonuclease Recognition Sequence of Two-Codon with 5'-Orientation For example, 5'-GACGTC is the two-codon recognition sequence of Aat II. At each 5' end of non-coding sequence, 5'-GACGTC occupies the consecutive first and second codon positions which orient the entire non-coding sequence from 5' end towards 3' end. The third codon position in the succession of the non-coding sequence is occupied by one of the 64 codons (TABLE 3). The fourth codon position in the succession of the non-coding sequence is occupied by one of the 64 codons as well as each of the subsequent sequential codon positions in 5' end towards 3' end orientation thereafter. The numbers of the distinctive 5'-GACGTC oriented non-coding sequences increase with increasing length. The said numbers could be calculated as long as the specific length (n) and (m) were given according to algorithm of $64^{(n-m)}$. In one embodiment, 12 mers 5'-GACGTC oriented non-coding sequence is four-codon length long. 5'-GACGTC is the pre-determined two-codon length long oriented sequence. Therefore, n=4, m=2, E=n−m. E is exponent. $64^{(n-2)}=4,096$. The total numbers of distinctive 12 mers 5'-GACGTC oriented non-coding sequences are 4,096. The $n^{th}$ codon occupies the nucleotide positions (3n−2) to (3n) in 5'-GACGTC oriented n-codon length long sequence. Each of the nucleotide positions of the $n^{th}$ codon in 5'-oriented triplet format is (3n−2), (3n−1) and (3n) respectively.

In one preferred embodiment, a collection of all the 4,096 distinctive 12 mers 5'-GACGTC oriented non-coding sequences has formed a standardized universal 12 mers oligonucleotide library, which is capable to be used as a standardized, universal and all-purpose 12 mers oligonucleotide probe and primer library.

(b) The Series Standardized Universal ORF Sense Oligonucleotide Libraries of Restriction Endonuclease Recognition Sequence of Two-Codon at the 3'-End Orientation For example, 5'-GACGTC is the two-codon recognition sequence of Aat II. At each 3' end of non-coding sequence, 5'-GACGTC occupies the consecutive first and second codon positions which orient the entire non-coding sequence from 3' end towards 5' end. The third codon position in the succession of the non-coding sequence is occupied by one of the 64 codons (TABLE 3). The fourth codon position in the succession of the non-coding sequence is occupied by one of the 64 codons as well as each of the subsequent sequential codon positions in 3' end towards 5' end orientation thereafter. The numbers of the distinctive 5'-GACGTC oriented non-coding sequences increase with increasing length. The said numbers could be calculated as long as the specific length (n) and (m) were given according to algorithm of $64^{(n-m)}$. In one embodiment, 12 mers 5'-GACGTC oriented non-coding sequence is four-codon length long. 5'-GACGTC is the pre-determined two-codon length long oriented sequence. Therefore, n=4, m=2, E=n−m. E is exponent. $64^{(n-2)}=4,096$. The total numbers of distinctive 12 mers 5'-GACGTC oriented non-coding sequences are 4,096. The $n^{th}$ codon occupies the nucleotide positions (3n) to (3n−2) in 5'-GACGTC oriented n-codon length long sequence. Each of the nucleotide positions of the $n^{th}$ codon in 5'-oriented triplet format is (3n), (3n−1) and (3n−2) respectively.

In one preferred embodiment, a collection of all the 4,096 distinctive 12 mers 5'-GACGTC oriented non-coding sequences has formed a standardized universal 12 mers oligonucleotide library, which can be used as a standardized, universal and all-purpose 12 mers oligonucleotide probe and primer library.

5. The Series Standardized Universal ORF Sense Oligonucleotide Libraries between 5'-and 3'-Orientations (a) The Series Standardized Universal ORF Sense Oligonucleotide Libraries between 5' and 3' of 5'-End Orientation At each 5' end of ORF sequence, one of the 61 codons (TABLE 1) occupies the first codon position which orients the entire ORF sequence from 5' end towards 3' end. The second codon position in the succession of the ORF sequence is occupied by one of the 61 codons (TABLE 1). The third codon position in the succession of the ORF sequence is occupied by one of the 61 codons as well as each of the subsequent sequential codon positions in 5' end towards 3' end orientation thereafter. The numbers of the distinctive 5'-one-codon oriented ORF sequences increase with increasing length. The said numbers could be calculated as long as the specific length (n) and (m) were given according to algorithm of $61^{(n-m)}$. In one embodiment, 9 mers 5'-one-codon oriented ORF sequence is three-codon length long. 5'-one-codon is the pre-determined one-codon length long oriented sequence. Therefore, n=3, m=1, E=n−m. E is exponent. $61^{(3-1)}=3,721$. The total numbers of distinctive 9 mers 5'-one-codon oriented ORF sequences are 226,981 ($3,721 \times 61$). The $n^{th}$ codon occupies the nucleotide positions (3n−2) to (3n) in 5'-one-codon oriented n-codon length long sequence. Each of the nucleotide positions of the $n^{th}$ codon in 5'-oriented triplet format is (3n−2), (3n−1) and (3n) respectively.

In one preferred embodiment, a collection of all the 226,981 distinctive 9 mers one-codon oriented ORF sequences has formed a standardized universal 9 mers oligonucleotide library, which can be used as a standardized, universal and all-purpose 9 mers oligonucleotide probe and primer library.

(b) The Standardized Universal ORF Oligonucleotide Libraries between 5' and 3' of 3'-End Orientation At each 3' end of ORF sequence, one of the 61 codons (TABLE 1) occupies the first codon position which orients the entire ORF sequence from 3' end towards 5' end. The second codon position in the succession of the ORF sequence is occupied by one of the 61 codons (TABLE 1). The third codon position in the succession of the ORF sequence is occupied by one of the 61 codons as well as each of the subsequent sequential codon positions in 3' end towards 5' end orientation thereafter. The numbers of the distinctive 5'-one-codon oriented ORF sequences increase with increasing length. The said numbers could be calculated as long as the specific length (n) and (m) were given according to algorithm of $61^{(n-m)}$. In one embodiment, 9 mers 5'-one-codon oriented ORF sequence is three-codon length long. 5'-one-codon is the pre-determined one-codon length long oriented sequence. Therefore, n=3, m=1, E=n−m. E is exponent. $61^{(3-1)}=3,721$. The total numbers of distinctive 9 mers 5'-one-codon oriented ORF sequences are 226,981 (3,721.times.61). The $n^{th}$ codon occupies the nucleotide positions (3n) to (3n−2) in 5'-one-codon oriented n-codon length long sequence. Each of the nucleotide positions of the $n^{th}$ codon in 5'-oriented triplet format is (3n−2), (3n−1) and (3n) respectively.

In one preferred embodiment, a collection of all the 226, 981 distinctive 9 mers one-codon oriented ORF sequences has formed a standardized universal 9 mers oligonucleotide library, which can be used as a standardized, universal and all-purpose 9 mers oligonucleotide probe and primer library.

5. The Standardized Universal ORF Sense Hexamer Oligonucleotide Library

In one embodiment, two codons were selected from the group consisting of the 61 codons (TABLE 1) at each time. By adding all possible combinations of two codons from the 61 codons without any overlap and repetition, The Universal ORF Sense Hexamer Oligonucleotide Library is synthesized. It comprises 3,721 distinct deoxyoligonucleotides or 3,721 distinct oligonucleotides. Each of the deoxyoligonucleotides or oligonucleotides is two-codon length long (3.times.2 nucleotides) with 5' orientation. Any and all of the stop codons is excluded. The algorithm for the construction of the Standardized Universal ORF Sense Hexamer Oligonucleotide Library is $61^n$ which is under the conditions of n=2, $61^2=3,721$ and one of the 61 codons is occupied each of the first codon position of 5'-end distinct 3,721 hexamer oligonucleotides.

In one preferred embodiment, a collection of all the 3,721 distinctive hexamer oligonucleotide sequences has formed a standardized universal hexamer oligonucleotide library, which can be used as a standardized, universal and all-purpose hexamer oligonucleotide probe and primer library.

6. The Series Standardized Universal 5'-UTR Sense Oligonucleotide Libraries of 3'-End Start Codon Orientation For example, one start codon, such as 5'-ATG is added at 3' end of 5'-UTR, 5'-ATG occupies the first codon position which orients the entire 5'-UTR sequence from 3' end towards 5' end. The second codon position in the succession of 5'-UTR sequence is occupied by one of the 64 codons (TABLE 3). The third codon position in the succession of 5'-UTR sequence is occupied by one of the 64 codons as well as each of the subsequent sequential codon positions in 3' end towards 5' end orientation thereafter (TABLE 10). The numbers of the distinctive 5'-ATG oriented 5'-UTR sequences increase with increasing length. The said numbers could be calculated as long as the specific length (n) and (m) were given according to algorithm of $64^{(n-m)}$. In one embodiment, 9 mers 5'-ATG oriented 5'-UTR sequence is three-codon length long. 5'-ATG is the pre-determined one-codon length long oriented sequence. Therefore, n=3, m=1, E=n−m. E is exponent. $64^{(3-1)}=4,096$. The total numbers of distinctive 9 mers 5'-ATG oriented 5'-UTR sequences are 4,096. The negative sign in front of n only indicates that codon position is in 5'-UTR. Therefore, the comparison of the absolute value of n and m does not take the negative sign into consideration. Based on the said principle, when m<n<infinity, the codon position is (m−n); the n h codon occupies 5'-ATG oriented 5'-UTR nucleotide positions 3(1−n) to 3(1−n)+2 in 3'-towards 5'-orientation when n>m, m=1. According to the said principle, each of the nucleotide positions of the $n^{th}$ codon in 5' oriented triplet formation is 3(1−n), 3(1−n)+1 and 3(1−n)+2 respectively when n>m, m=1.

In one preferred embodiment, a collection of all 4,096 distinctive 9 mers 5'-ATG oriented 5'-UTR sequences has formed a standardized universal 9 mers oligonucleotide library, which can be used as a standardized, universal and all-purpose 9 mers oligonucleotide probe and primer library.

7. The Series Standardized Universal 3'-UTR Oligonucleotide Libraries of 5'-End Stop Codon Orientation As discussed above, there are three major stop codons (5'-TAA, 5'-TGA, 5'-TAG). For example, one stop codon; such as 5'-TGA is added at 5' end of 3'-UTR, 5'-TGA occupies the first codon position which orients the entire 3'-UTR sequence from 5' end to 3' end. The second codon position in the succession of 3'-UTR sequence is occupied by one of the 64 codons(TABLE 3). The third codon position in the succession of 3'-UTR sequence is occupied by one of the 64 codons as well as each of the subsequent sequential codon positions in 5' end towards 3' end orientation thereafter (TABLE 10). The numbers of the distinctive 5'-TGA oriented 3'-UTR sequences increase with increasing length. The said numbers could be calculated as long as the specific length (n) and (m) were given according to algorithm of $64^{(n-m)}$. In one embodiment, 9 mers 5'-TGA oriented 3'-UTR sequence is three-codon length long. 5'-TGA is the pre-determined one-codon length long oriented sequence. Therefore, n=3, m=1, E=n−m. E is exponent. $64^{(3-1)}=4,096$. The total numbers of distinctive 9 mers 5'-TGA oriented 3'-UTR sequences are 4,096. The $n^{th}$ codon occupies the nucleotide positions (3n−2) to (3n) of the 5'-TGA oriented 3'-UTR sequence of n-codon length long (TABLE 10). Each of the nucleotide positions of the $n^{th}$ codon in 5'-oriented triplet format is (3n−2), (3n−1) and (3n) respectively.

In one preferred embodiment, a collection of all the distinctive 9 mers 5'-stop codon oriented 3'-UTR sequences (4,096 times. 3) has formed a standardized universal 9 mers oligonucleotide library, which can be used as a standardized, universal and all-purpose 9 mers oligonucleotide probe and primer library.

8. The Series Standardized Universal Antisense Oligonucleotde Libraries of Antisense Start Codon Orientation Antisense oligonucleotides with their analogues and derivatives, such as LNA are designed to bind their complementary sequences of mRNA. The bindings often inhibit the expression of the target peptides and proteins. Its application has a wide spectrum range from clinical therapy (Stein et al., Science 261: 1004-1012, 1993) to food processing industry (Bachem et al., Bio/Technol. 12: 1101-1105, 1994).

One of the major concerns of antisense oligonucleotides is the specificity of the modulations to the flow of genetic information. In theory, the longer the length is, the more specific antisense oligonucleotides will be. In practice, 12-25 nucleotide-long antisense oligonucleotides were frequently employed in experiments (Woolf et al., Proc. Natl. Acad. Sci. USA 89: 7305-7309, 1992). The specificity of inhibition of short antisense oligonucleotides (7-8 nucleotide-long with C-5 propyne primidines and phosphorothioate internucleotide linkages) has also been explored (Wagner et al., Nat. Biotechnol. 14: 840-844, 1996). Another concern is the suitable targeting areas for antisense oligonucleotide. There are a number of typical targeting locations of genes for antisense design, such as the 5'-cap region, the translation initiation region and the termination region. 5'-ATG and downstream sequence are generally regarded as the more promising target locations for antisense inhibition (Chen et al., Molecular & Cellular Proteomics 2(9): 998, 2003).

For example, at each 3'-end of antisense ORF sequence, the first antisense codon position is solely occupied by antisense start codon, such as 3'-TAC in 3' towards 5' orientation. The second antisense codon position adjacent to the 5' end of the anti-sense start codon, such as 3'-TAC is occupied by one of 61 antisense codons (TABLE 2) in 3' towards 5' orientation. The third antisense codon position in the succession of the antisense ORF sequence is occupied by one of the 61 antisense codons as well as each of the subsequent sequential antisense codon positions in 3' towards 5' orientation thereafter. The numbers of the distinctive 3'-TAC oriented antisense ORF sequences increase with increasing length. The said numbers could be calculated as long as the specific length (n) and (m) were given according to algorithm of $61^{(n-m)}$. In one embodiment, 3'-TAC oriented antisense ORF sequence is three-antisense-codon length long. 3'-TAC is the pre-determined one-antisense-codon length long oriented antisense sequence. Therefore, n=3, m=1, E=n−m. E is exponent. $61^{(3-1)}=3,721$. The total numbers of distinctive 9 mers 3'-TAC oriented antisense ORF sequences are 3,721.

In one preferred embodiment, a collection of all the 3,721 distinctive 9 mers 3'-TAC oriented antisense ORF sequences has formed a standardized universal 9mers antisense oligonucleotide library, which can be used as a standardized and all-purpose, universal 9mers antisense oligonucleotide probe and primer library.

9. The Series Standardized Universal Peptide Libraries of N-terminal Orientation For example, Methionine or Formylmethionine occupies the first amino acid position of the peptide of N-terminal. The second amino acid position immediately adjacent to Methionine or Formylmethionine is occupied by one of the 20 Essential Amino Acids (EM) in N-terminal towards C-terminal orientation. The third amino acid position in the succession of the peptide sequence is occupied by one of the 20 EAA as well as each of the subsequent sequential amino acid positions in N-terminal towards C-terminal orientation thereafter (TABLE 15). The numbers of the distinctive Methionine or Formylmethionine oriented peptide increase with increasing length. The said numbers could be calculated as long as the specific length (n) and (m) were given according to the algorithm of $20^{(n-m)}$. In one embodiment, Methionine oriented 6-peptide sequence is six amino acids length long. Methionine is the pre-determined one-amino-acid length long oriented sequence. Therefore, n=6, m=1, E=n−m. E is exponent. $20^{(6-1)}=3,200,000$. The total numbers of distinctive Methionine oriented 6-peptide sequences are 3,200,000 (TABLE 15).

In one preferred embodiment, a collection of all the 3,200,000 distinctive Methionine oriented 6-peptide sequences has formed a standardized universal 6-peptide library, which is capable to be used as a standardized, universal and all-purpose 6-peptide antigen or epitope library.

10. The Series Standardized Universal Peptide Libraries of C-terminal Orientation As discussed above, one stop codon is at the 3'-end of ORF sequence wherein peptide is released during protein synthesis. For example, the first amino acid position of C-terminal of peptide or protein may be occupied by one of the 20 EAA in C-terminal towards N-terminal orientation. The second amino acid position in the succession of C-terminal oriented peptide sequence is occupied by one of the 20 EAA in C-terminal towards N-terminal orientation. The third amino acid position in the succession of the peptide sequence is occupied by one of the 20 EAA as well as each of the subsequent sequential amino acid positions in C-terminal towards N-terminal orientation thereafter (TABLE 16). The numbers of the distinctive C-terminal oriented peptide increase with increasing length. The said numbers could be calculated as long as the specific length (n) and (m) were given according to algorithm of $20^{(n-m)}$. In one embodiment, One of the 20 EAA oriented 6-peptide sequence is six amino acids length long. One of the 20 EAA is the pre-determined one-amino-acid length long oriented sequence. Therefore, n=6, m=1, E=n−m. E is exponent. $20^{(6-1)}=3,200,000$. The total number of distinctive C-terminal oriented 6-peptide sequences is 64,000,000 (3,200,000×20). In one preferred embodiment, a collection of all the 64,000,000 distinctive C-terminal oriented 6-peptide sequences has formed a standardized universal 6-peptide library, which can be used as a standardized, universal and all-purpose 6-peptide antigen or epitope library.

11. The Series Standardized Universal Peptide Libraries between N-terminal and C-terminal Orientations (a) The Series Standardized Universal Peptide Libraries between N-terminal and C-Terminal of N-Terminal Orientation For example, the first amino acid position at N-terminal is occupied by one of the 20 EAA. The second amino acid position immediately adjacent to the first amino acid position is occupied by one of the 20 EAA in N-terminal towards C-terminal orientation. The third amino acid position in the succession of the peptide sequence is occupied by one of the 20 EAA as well as each of the subsequent sequential amino acid positions in N-terminal towards C-terminal orientation thereafter. Therefore, the $n^{th}$ amino acid position is occupied by one of the 20 essential amino acids in N-terminal towards C-terminal orientation within a peptide sequence of n amino acids long. There are total $20^{(n-1)} \times 20$ or $20^E \times 20$ distinct n-peptide long peptide of N-terminal oriented sequences. The numbers of the distinctive N-terminal oriented peptide increase with increasing length. The said numbers could be calculated as long as the specific length (n) and (m) were given according to algorithm of $20^{(n-m)}$. In one embodiment, when n=6, m=1, E=n−m, $20^{(6-1)}=3,200,000$. The total number of distinctive N-terminal oriented 6-peptide sequences is 64,000,000 (3,200,000× 20).

In one preferred embodiment, a collection of all the above 64,000,000 distinctive N-terminal oriented 6-peptide sequences has formed a standardized universal 6-peptide library, which can be used as a standardized, universal and all-purpose 6-peptide antigen or epitope library.

(b) The Series Standardized Universal Peptide Libraries between N-terminal and C-terminal of C-terminal Orientation For example, the first amino acid position at C-terminal is occupied by one of the 20 EAA. The second amino acid position immediately adjacent to the first amino acid position is occupied by one of the 20 EAA in C-terminal towards N-terminal orientation. The third amino acid position in the succession of the peptide sequence is occupied by one of the 20 EAA as well as each of the subsequent sequential amino acid positions in C-terminal towards N-terminal orientation thereafter. Therefore, the $n^{th}$ amino acid position is occupied by one of the 20 EAA in C-terminal towards N-terminal orientation within a peptide sequence of n amino acids long. There are total distinct C-terminal oriented 20.sup.(n−m).times.20 n-amino-acid length long peptides sequences. The numbers of the distinctive C-terminal oriented peptide increases with increasing length. The said numbers could be calculated as long as the specific length (n) and (m) were given according to algorithm of 20.sup.(n−m). In one embodiment, when n=6, m=1, E=n−m, 20.sup.(6−1)=3,200,000. The total number of distinctive C-terminal oriented 6-peptide sequences is 64,000,000 (3,200,000.times.20).

In one preferred embodiment, a collection of all the above 64,000,000 distinctive C-terminal oriented 6-peptide sequences has formed a standardized universal 6-peptide library, which can be used as a standardized universal and all-purpose 6-peptide antigen or epitope library.

12. The Series Standardized Universal Peptide Libraries of Restriction Endonuclease Recognition Sequence Two-Amino Acids Orientations The restriction endonuclease is selected from the group of restriction endonucleases which have two-codon recognition sequences which excluded any and all stop codons within the two codons. Examples of suitable restriction endonucleases include but are by no means limited to Aat II, Acc65 I, Acl I, Afe I, Afl II, Age I, Apa I, ApaL I, Ase I, Avr II, BamHI, BfrBI, Bgl II, Bmel580 I, BmgB I, BseY I, Btr I, BsiW I, BspD I, BspE I, BsrB I, BsrG I, BssH II, BssS I, Bst B I, BstZ17 I, Cla I, Dra I, Eag I, EcoR I, EcoR V, Fsp I, Hind III, Hpa I, Kas I, Kpn I, Mfe I, Mlu I, Msc I, Nae I, Nar I, Nco I, Nde I, NgoM IV, Nhe I, Nru I, Nsi I, PaeR7 I, Pci I, Pml I, PspOM I, Pst I, Pvu I Pvu II, Sac I, Sac II, Sal I, Sca I, Sfo I, Sma I, SnaB I, Spe I, Sph I, Ssp I, Stu I, Tli I, Xba I, Xho I, Xma I, Acc I, BsaW I, BsiHKA I, Bsp1286 I, MspAl I, and Sty I. The excluded restriction endonucleases with two-codon recognition sequence are Bcl I, BspH I and Psi I. The corresponding restriction endonuclease recognition sequences of two-codon are shown in TABLE 5. In one embodiment, the preferred panel of peptides comprising two amino acids deduced from the above restriction endonuclease recognition sequences which include but are by no means limited to TABLE 5.

(a) The Series Standardized Universal Peptide Libraries of Restriction Endonuclease Recognition Sequence of Two-Amino-Acids of N-terminal Orientation For example, 5'-GACGTC is the recognition sequence of two-codon of restriction endonuclease Aat II. $NH_2$-DV is encoded by 5'-GACGTC. In some embodiments, a two-amino-acids peptide from a restriction endonuclease recognition sequence is placed at the N-terminal of a designed peptide. For example, $NH_2$-DV is placed at the consecutive first and second amino acids positions of N-terminal of the designed peptide which orients the entire peptide sequence from N-terminal towards C-terminal. The consecutive first and second amino acid positions of peptide is solely occupied by the designed two-amino-acids of the restriction endonuclease recognition sequence of two-codon, e.g. $NH_2$-DV in N-terminal towards C-terminal. The third amino acid position adjacent to the C-terminal of $NH_2$-DV (the first and second amino acid positions) is occupied by one of the 20 EAA in N-terminal towards C-terminal orientation. The fourth amino acid position in the succession of the peptide sequence is occupied by one of the 20 EAA as well as each of the subsequent sequential amino acid positions in N-terminal towards C-terminal orientation thereafter. Therefore, the $n^{th}$ amino acid position of peptide is occupied by one of 20.sup.(n−2) or(20.sup.Erers) amino acids in N-terminal towards C-terminal orientated manner within n-peptide length long sequences. Erers means Exponent of restriction endonuclease recognition sequence. Erers is exponent. $NH_2$-DV is the predetermined two-amino-acids length long oriented sequence. In one embodiment, when n=6, m=2, Erers=n−m, 20.sup.(n−2)=160,000.

In one preferred embodiment, a collection of all the above 160,000 distinctive $NH_2$-DV oriented 6-peptide sequences has formed a standardized universal 6-peptide library, which can be used as a standardized, universal and all-purpose 6-peptide antigen or epitope library.

(b) The Series Standardized Universal Peptide Libraries of Restriction Endonuclease Recognition Sequence of Two-Amino-Acids of C-terminal Orientation Similarly, 5'-GACGTC is the recognition sequence of two-codon of restriction endonuclease Aat II. DV-COOH is encoded by 5'-GACGTC. In one embodiment, a two-amino-acids peptide from a restriction endonuclease recognition sequence is placed at the C-terminal of a designed peptide. For example, DV-COOH is placed at the consecutive first and second amino acids positions of C-terminal of the designed peptide which orients the entire peptide sequence from C-terminal towards N-terminal. The consecutive first and second amino acid positions of peptide is solely occupied by the designed two-amino-acids of the restriction endonuclease recognition sequence of two-codon, e.g. DV-COOH in C-terminal towards N-terminal orientation. The third amino acid position adjacent to the N-terminal of DV-COOH (the first and second amino acid positions) is occupied by one of the 20 EAA in C-terminal towards N-terminal orientation. The fourth amino acid position in the succession of the peptide sequence is occupied by one of the 20 EAA as well as each of the subsequent sequential amino acid positions in C-terminal towards N-terminal orientation thereafter. Therefore, the nth amino acid position of peptide is occupied by one of 20.sup.(n−2) or(20.sup.Erers) amino acids in C-terminal towards N-terminal orientated manner within n-peptide length long sequences. Erers means Exponent of restriction endonuclease recognition sequence. Erers is exponent. DV-COOH is the pre-determined two-amino-acids length long oriented sequence. In another embodiment, when n=6, m=2, Erers=n−m, 20.sup.(n−2)=160,000.

In another preferred embodiment, a collection of all the above 160,000 distinctive DV-COOH oriented 6-peptide sequences has formed a standardized universal 6-peptide library, which can be used as a standardized, universal and all-purpose 6-peptide antigen or epitope library.

13. The Series Standardized Universal Antibody Libraries Produced by the Antigens or Epitopes of the Corresponding Series Standardized Universal Peptide Libraries of N-terminal Methionine Orientation (a) The Corresponding Series Standardized Universal Monoclonal Antibody Libraries (b) The Corresponding Series Standardized Universal Multiclonal Antibody Libraries (c) The Secondary Corresponding Series Standardized Universal Monoclonal Antibody Libraries (d) The Secondary Corresponding Series Standardized Universal Multiclonal Antibody Libraries The algorithms for the construction of the Series Standardized Universal Antibody Libraries produced by the Antigens or Epitopes of the Corresponding Series Standardized Universal Peptide Libraries of N-terminal Methionine orientation are as following: 20.sup.(n−1) under the conditions: n=5 or 5<n<infinity. n is an integer. One amino acid encoded by a Start Codon, such as Methionine encoded by 5'-ATG is at the first amino acid position of N-terminal of each antigen or epitope sequence. The productions of monoclonal and multiclonal antibodies are known in the art to those of ordinary skill.

14. The Series Standardized Universal Antibody Libraries Produced by the Antigens or Epitopes of the Corresponding Series Standardized Universal Peptide Libraries of C-terminal Orientation
  (a) The Corresponding Series Standardized Universal Monoclonal Antibody Libraries
  (b) The Corresponding Series Standardized Universal Multiclonal Antibody Libraries
  (c) The Secondary Corresponding Series Standardized Universal Monoclonal Antibody Libraries
  (d) The Secondary Corresponding Series Standardized Universal Multiclonal Antibody Libraries The algorithms for the construction of the Series Standardized Universal Antibody Libraries produced by the Antigens or Epitopes of the Corresponding Series Standardized Universal Peptide Libraries of C-terminal orientation are as following: $20.\sup.(n-1)$ under the conditions: n=5 or 5<n<infinity. n is an integer. One amino acid encoded by an amino acid coding codon is at the first amino acid position of C-terminal of each antigen or epitope sequence. The productions of monoclonal and multiclonal antibodies are known in the art to those of ordinary skill.

15. The Series Standardized Universal Antibody Libraries Produced by the Antigens or Epitopes of the Corresponding Series Standardized Universal Peptide Libraries of N-terminal Restriction Endonuclease Recognition Sequence of Two-Amino-Acids Orientation
  (a) The Corresponding Series Standardized Universal Monoclonal Antibody Libraries
  (b) The Corresponding Series Standardized Universal Multiclonal Antibody Libraries
  (c) The Secondary Corresponding Series Standardized Universal Monoclonal Antibody Libraries
  (d) The Secondary Corresponding Series Standardized Universal Multiclonal Antibody Libraries The algorithms for the construction of the Series Standardized Universal Antibody Libraries produced by the Antigens or Epitopes of the Corresponding Series Standardized Universal N-terminal Restriction Endonuclease Recognition Sequence of Two-Amino Acids Orientation Peptide Libraries of are as following: $20.\sup.(n-2).\text{times}.(REN)$ under the conditions: n=5, or 5<n<infinity, n is an integer, $20.\sup.(n-2).\text{times}.(REN)$, $20.\sup.(n-2).\text{times}.1$, when REN=1. REN: Restriction Endonuclease Number. Two amino acids encoded by Restriction Endonuclease Recognition Sequence of Two-codon are the consecutive first and second positions at N-terminal of each antigen or epitope sequences. The productions of monoclonal and multiclonal antibodies are known in the art to those of ordinary skill.

16. The Series Standardized Universal Antibody Libraries Produced by the Antigens or Epitopes of the Corresponding Series Standardized Universal Peptide Libraries of C-terminal Restriction Endonuclease Recognition Sequence of Two-Amino-Acids Orientation
  (a) The Corresponding Series Standardized Universal Monoclonal Antibody Libraries
  (b) The Corresponding Series Standardized Universal Multiclonal Antibody Libraries
  (c) The Secondary Corresponding Series Standardized Universal Monoclonal Antibody Libraries
  (d) The Secondary Corresponding Series Standardized Universal Multiclonal Antibody Libraries The algorithms for the construction of the Series Standardized Universal Antibody Libraries produced by the Antigens or Epitopes of the Corresponding Series Standardized Universal C-terminal Restriction Endonuclease Recognition Sequence of Two-Amino-Acids Orientation Peptide Libraries of are as following: $20.\sup.(n-2).\text{times}.(REN)$ under the conditions: n=5, or 5<n<infinity, n is an integer, $20.\sup.(n-2).\text{times}.(REN)$, $20.\sup.(n-2).\text{times}.1$, when REN=1. REN: Restriction Endonuclease Number. Two-amino-acids encoded by Restriction Endonuclease Recognition Sequence of Two-codon are the consecutive first and second positions at C-terminal of each antigen or epitope sequences. The productions of monoclonal and multiclonal antibodies are known in the art to those of ordinary skill.

II. GC Identical Oligonucleotide Panels

The GC content of those oligonucleotide libraries which have been constructed according to algorithm of $61.\sup.(n-m)$ wherein m=1 has a Poisson distribution.

In one embodiment, 3,721 distinctive 9 mers 5'-ATG oriented oligonucleotides of a library have been classified into seven GC Identical Panels according to GC content as following: (1) 64 distinctive oligonucleotides of 77.8% GC content, (2) 384 distinctive oligonucleotides of 66.7% GC content, (3) 928 distinctive oligonucleotides of 55.6% GC content, (4) 1,168 distinctive oligonucleotides of 44.4% GC content, (5) 820 distinctive oligonucleotides of 33.3% GC content, (6) 308 distinctive oligonucleotides of 22.2% GC content and (7) 49 distinctive oligonucleotides of 11.1% GC content. Each of the said panels includes all necessary and suitable positive and negative controls known in the art.

In another embodiment, 3,721 distinctive 9 mers 5'-TGA oriented oligonucleotides of a library have been classified into seven GC Identical Panels according to GC content as following: (1) 64 distinctive oligonucleotides with 77.8% GC content, (2) 384 distinctive oligonucleotides with 66.7% GC content, (3) 928 distinctive oligonucleotides with 55.6% GC content, (4) 1,168 distinctive oligonucleotides with 44.4% GC content, (5) 820 distinctive oligonucleotides with 33.3% GC content, (6) 308 distinctive oligonucleotides with 22.2% GC content and (7) 49 distinctive oligonucleotides with 11.1% GC content. Each of the said panels includes all necessary and suitable positive and negative controls known in the art.

In an alternative embodiment, 3,721 distinctive 9 mers 5'-TAG oriented oligonucleotides of a library have been classified into seven GC Identical Panels according to GC content as following: (1) 64 distinctive oligonucleotides with 77.8% GC content, (2) 384 distinctive oligonucleotides with 66.7% GC content, (3) 928 distinctive oligonucleotides with 55.6% GC content, (4) 1,168 distinctive oligonucleotides with 44.4% GC content, (5) 820 distinctive oligonucleotides with 33.3% GC content, (6) 308 distinctive oligonucleotides with 22.2% GC content and (7) 49 distinctive oligonucleotides with 11.1% GC content. Each of the said panels includes all necessary and suitable positive and negative controls known in the art.

In one embodiment, 4,096 distinctive 9 mers 5'-ATG oriented oligonucleotides of a library have been classified into seven GC Identical Panels according to GC content as following: (1) 64 distinctive oligonucleotides with 77.8% GC content, (2) 384 distinctive oligonucleotides with 66.7% GC content, (3) 960 distinctive oligonucleotides with 55.6% GC content, (4) 1,280 distinctive oligonucleotides with 44.4% GC content, (5) 960 distinctive oligonucleotides with 33.3% GC content, (6) 384 distinctive oligonucleotides with 22.2%

GC content and (7) 64 distinctive oligonucleotides with 11.1% GC content. Each of the said panels includes all necessary and suitable positive and negative controls known in the art.

In another embodiment, 4,096 distinctive 9 mers 5'-TGA oriented oligonucleotides of a library have been classified into seven GC Identical Panels according to GC content as following: (1) 64 distinctive oligonucleotides with 77.8% GC content, (2) 384 distinctive oligonucleotides with 66.7% GC content, (3) 960 distinctive oligonucleotides with 55.6% GC content, (4) 1,280 distinctive oligonucleotides with 44.4% GC content, (5) 960 distinctive oligonucleotides with 33.3% GC content, (6) 384 distinctive oligonucleotides with 22.2% GC content and (7) 64 distinctive oligonucleotides with 11.1% GC content. Each of the said panels includes all necessary and suitable positive and negative controls known in the art.

In another embodiment, 4,096 distinctive 9 mers 5'-TAG oriented oligonucleotides of a library have been classified into seven GC Identical Panels according to GC content as following: (1) 64 distinctive oligonucleotides with 77.8% GC content, (2) 384 distinctive oligonucleotides with 66.7% GC content, (3) 960 distinctive oligonucleotides with 55.6% GC content, (4) 1,280 distinctive oligonucleotides with 44.4% GC content, (5) 960 distinctive oligonucleotides with 33.3% GC content, (6) 384 distinctive oligonucleotides with 22.2% GC content and (7) 64 distinctive oligonucleotides with 11.1% GC content. Each of the said panels includes all necessary and suitable positive and negative controls known in the art.

In yet another embodiment, 4,096 distinctive 12 mers 5'-GGATCC (BamH I) oriented oligonucleotides of a library have been classified into seven GC Identical Panels according to GC content as following: (1) 64 distinctive oligonucleotides with 91.7% GC content, (2) 384 distinctive oligonucleotides with 75% GC content, (3) 960 distinctive oligonucleotides with 66.7% GC content, (4) 1,280 distinctive oligonucleotides with 58.3% GC content, (5) 960 distinctive oligonucleotides with 50% GC content, (6) 384 distinctive oligonucleotides with 41.7% GC content and (7) 64 distinctive oligonucleotides with 33.3% GC content. Each of the said panels includes all necessary and suitable positive and negative controls known in the art.

In some embodiments, oligonucleotides with 77.8% GC content or greater are grouped together while oligonucleotides with 11.1% GC content or less are grouped together respectively.

In yet other embodiments, the oligonucleotides within a library which have the identical length and identical orientation are grouped according to GC content, which may subsequently be regrouped into a sub-library or sub GC Identical Panels. Each of the said sub GC Identical Oligonucleotide Panels includes all necessary and suitable positive and negative controls known in the art.

In another embodiment, the oligonucleotides of a given GC Identical Panel or sub GC Identical Panel have been elongated by adding a codon consisting of three consecutive universal bases, wherein said universal bases are selected from the group comprising 5'-nitroindole-2'-deoxyriboside, 3-nitropyrrole, inosine, pypoxanthine and combinations thereof. The said codon is being covalently linked at the 5'-end of each of the said oligonucleotides.

In another embodiment, the oligonucleotides of a given GC Identical Panel or sub GC Identical Panel have been elongated by adding a codon consisting of three consecutive universal bases, wherein said universal bases are selected from the group comprising 5'-nitroindole-2'-deoxyriboside, 3-nitropyrrole, inosine, pypoxanthine and combinatorial thereof. The said codon is being covalently linked at 3'-end of each of the said oligonucleotides.

In yet another embodiment, each of the oligonucleotides of a given GC Identical Panel or sub GC Identical Panel has been incorporated with at least one LNA. Tm has been increased by about 2° C. degrees per each incorporated LNA, such as 2'-O, 4'-methylene-beta-D-robofuranosyl nucleotide monomer.

In yet another preferred embodiment, each of the 820 distinctive 9 mers 5'-ATG oriented oligonucleotides of a GC Identical Panel, wherein the said GC Identical Panel has 33.3% GC content, contains eight 2'-O, 4'-methylene-beta-D-robofuranosyl nucleotide monomer(s) within its 9 mers sequence. After the incorporation of LNA, Tm of each said oligonulceotide has been adjusted from 28° C. degrees to 42° C. degrees for both PCR and hybridization.

In one preferred embodiment, the oligonucleotides with at least one or more of LNA of a given GC Identical Panel or sub GC Identical Panel have been elongated by adding a codon consisting of three consecutive universal bases, wherein said universal bases are selected from the group comprising 5'-nitroindole-2'-deoxyriboside, 3-nitropyrrole, inosine, pypoxanthine and combinations thereof. The said codon is being covalently linked at 5'-end of each of the said oligonucleotides.

In another preferred embodiment, the oligonucleotides with at least two or more of LNA of a given GC Identical Panel or sub GC Identical Panel have been elongated by adding a codon consisting of three consecutive universal bases, wherein said universal bases are selected from the group comprising 5'-nitroindole-2'-deoxyriboside, 3-nitropyrrole, inosine, pypoxanthine and combinations thereof. The said codon is covalently linked at 3'-end of each of the said oligonucleotides.

Each of the said oligonucleotides is immobilized to a solid support in a set of each said oligonucleotide at a specific discrete position to form an array, the said set comprising at least two copies of the said oligonucleotide, the said array comprising at least two said sets. Each of the said oligonucleotides of identical GC content is immobilized on one piece of solid support composed of a suitable material, for example, glass, plastics, plastic plates, silicon, polymers, nylon filters, nitrocellulose filters, beads, streptavidin beads, magnetic beads, nanoparticles or other suitable supports known in the art. The Tm is being adjusted precisely according to the corresponding GC content or the numbers of incorporated LNA or both. In one preferred embodiment, each of the said oligonucleotides which have the identical length and GC content interact with their targeting sequences either on a surface of a solid phase such as, DNA Arrays, DNA Microarrays and Dot-Blot filters or in aqueous phase such as, PCR under identical and well-defined hybridization conditions by calculation of the Tm.

In one embodiment, a GC Identical Panel may comprise substantially all of the oligonucleotides of one of the above-described formulae.

In another embodiment, each oligonucleotide of a GC Identical Panel may consist essentially of an oligonucleotide according to the specific formula for the respective panel.

As will be appreciated by one of skill the art, a given single panel may consist of 2 or more sets of oligonucleotides or of peptides of one of the above-described formulae; 5 or more sets of oligonucleotides or of peptides of one of the above-described formulae; 10 or more sets of oligonucleotides or of peptides of one of the above-described formulae; 15 or more sets of oligonucleotides or of peptides of one of the above-described formulae; 20 or more sets of oligonucleotides or of peptides of one of the above-described formulae; 25 or more sets of oligonucleotides or of peptides of one of the above-described formulae; or 50 or more sets of oligonucleotides or of peptides of one of the above-described formulae; 100 or more sets of oligonucleotides or of peptides of one of the above-described formulae; or 200 or more sets of oligonucleotides or of peptides of one of the above-described formulae; 300 or more sets of oligonucleotides or of peptides of one of the above-described formulae; or 500 or more sets of oligonucleotides or of peptides of one of the above-described formulae; 1,000 or more sets of oligonucleotides or of peptides of one of the above-described formulae; or 2,000 or more sets of oligonucleotides or of peptides of one of the above-described formulae; 3,000 or more sets of oligonucleotides or of peptides of one of the above-described formulae; or 5,000 or more sets of oligonucleotides or of peptides of one of the above-described formulae; 10,000 or more sets of oligonucleotides or of peptides of one of the above-described formulae; or 20,000 or more sets of oligonucleotides or of peptides of one of the above-described formulae; 50,000 or more sets of oligonucleotides or of peptides of one of the above-described formulae; or 100,000 or more sets of oligonucleotides or of peptides of one of the above-described formulae; 200,000 or more sets of oligonucleotides or of peptides of one of the above-described formulae; or 500,000 or more sets of oligonucleotides or of peptides of one of the above-described formulae.

III. Synthesis of Oligonucleotide and Peptide

In one preferred embodiment, synthesis of oligonucleotides was carried out by phoshoramidite methods such as Caruthers et al., Nucleic Acids Res. Symp. Ser. 7: 215-223, 1980; Beaucage et al., Tetrahedron Lett. 22: 1859-1862, 1981; McBride et al., Tetrahedron Lett. 24: 245-248, 1983; and Beaucage et al., Tetrahedron Lett. 48: 2223-2311, 1992; all of which are incorporated herein by reference in their entirety for all purposes.

In one preferred embodiment, the synthesis of oligonucleotides was processed by the H-phoshonate methods such as Garegg et al., Chem. Scripta 25: 280-282, 1985; Garegg et al., Chem. Scripta 26: 59-62, 1986; Garegg et al., Tetrahedron Lett. 27: 4051-4054, 1986; Froehler et al., Nucleic Acids Res., 14: 5399-5407, 1986; Froehler et al., Tetrahedron Lett. 27: 4694472, 1986; Froehler et al., Tetrahedron Lett. 27: 5575-5578, 1986; all of which are incorporated herein by reference in their entirety for all purposes.

In another preferred embodiment, the synthesis of oligonucleotides was carried out by an automated nucleic acid synthesizer such as, ABI 381-A, ABI 391, ABI 392, ABI 3900 and Expedite 8909 Nucleic Acid Synthesizer of PE Applied Biosystems at a 0.2 µM scale using standard protocols in accordance with the manual of the manufacturer. Prior to the coupling step on a solid phase, the synthesized oligonucleotides then were purified, desalted and lyophilized at different grades of purity such as, PCR™-grade (ethanol precipitation to remove the salt), Probe-grade (purified by HPLC) and Gene-synthesis-grade (purified by polyacrylamide gel electrophoresis. The said purification methods and procedures are well known to those of skill in the art.

In one preferred embodiment, at specific defined discrete positions on a solid phase such as, a surface on silicon. In another preferred embodiment, the in-situ synthesis of oligonucleotides was carried out by photolithographic methods such as described by Fodor et al., Science 251: 767-773, 1991; Pease et al., Proc. Natl. Acad. Sci. U.S.A. 91: 5022-5026, 1994; Lockhart et al., Nat. Biotechol. 14: 1675,1996; Pirrung et al., U.S. Pat. No. 5,143,854, 1992; Fodor et al., U.S. Pat. No. 5,445,934, 1995; Fodor et al., U.S. Pat. No. 5,510, 270, 1996; Fodor et al., U.S. Pat. No. 5,800,992,1998; all of which are incorporated herein by reference in their entirety for all purposes.

In another preferred embodiment, at specific defined discrete position on the surface of glass plate, in-situ synthesis of oligonucleotides was processed in accordance with methods as described by Southern et al., Genomic13: 1008-1017, 1992; Maskos et al., Nucleic Acids Res. 20: 1679-1684, 1992; Southern et al., Nucleic Acids Res. 22: 1368-1373, 1994; all of which are incorporated herein by reference in their entirety for all purposes.

In another embodiment, in-situ synthesis of oligonucleotides and deposition on the perfluroinated hydrophobic surface of silicon dioxide was processed by Ink-jet printer heads as described by Blanchard et al., Biosensors & Bioelectronics 11: 687-690. This is incorporated herein by reference in its entirety for all purposes.

At the present time, the synthesis of oligonucleotides and peptides has become mature technology and standard laboratory operation procedures. It is the same for production of monoclonal antibodies. Moreover, many companies, such as Sigma-Genosys, Life Technologies and Washington Biotechnology Inc., provide routine service to produce the custom designed oligonucleotide, peptide and monoclonal antibodies tailored to different requirements and purposes. Those conditions allow one of skill in the art to prepare oligonucleotides, peptides and monoclonal antibodies with undue experimentation.

IV. Analogues and Derivatives of Oligonucleotide and Peptide

The oligonucleotides deduced according to the algorithm of $61.\sup.(n-m)$ and $64.\sup.(n-m)$ may contain restriction endonuclease recognition sequence(s) or promoter sequence(s) which include but are by no means limited to bacteriophage SP6, T3 and T7 sequence(s). The said oligonucleotides may have one or two or three or four or five or six universal base analogue(s) which include but are by no means limited to 5'-Nitroindole, 3-nitropyrrole, inosine and pypoxamthine. The said oligonucleotides may contain chemical modifications and substitutions on sugars, phosphates, phosphodiester bonds, bases, base analogues, universal bases and polyamide respectively or combinatorial. For example, the said chemical modifications and substitutions include but are by no means limited to 2'-O-alkylribose, 2'-O-Methylribonucleotide, Methylphosphonates, Morpholine, Phosphorothioate, Phosphordithioate, Sulfamate, H-phosphonate, phosphoroamidites, phosphotriesters, [(alpha)]-anomeric and the like. The said oligonucleotide analogues include but are by no means limited to Peptide Nucleic Acid (PNA) and Locked Nucleic Acid (LNA). The said oligonucleotides analogues include the modified nucleotide units which posses energy emission patterns of a light emitting chemical compound or a quenching compound such as, hypoxanthine, mercaptopurine, selenopurine, 2-aminopurine, 2,4-diselenouracil and 2,4-dithiouracil. Additionally, the said modifications and substitutions include modifications and substitutions known or under development or to be developed to the extent that such alterations facilitate or have no negative affect when the said oligonucleotides hybridize to complementary targeting sequences. The said oligonucleotides may contain minor deletions, insertions and additions of codons or bases to the extent that such alterations facilitate or do not negatively affect when the said oligonucleotides hybridize complementary targeting sequences. The said oligonucleotides may be DNA, cDNA, mRNA, Anti-sense DNA, Anti-sense mRNA and Peptide Nucleic Acids (PNA) in the format of either single strand or double strands. The said oligonucleotides may be labelled by a chemical composition(s) which produces specific detectable signal by radioactive ray, electromagnetic radiation, immunochemistry, biochemistry and photochemistry. Those labelling chemical composition include but are by no means limited to radioisotopes such as 3.sup.H, 14.sup.C, 32.sup.P, 33.sup.P, and 35.sup.S.; biotin; fluorescent molecules such as fluorescein isothiocyanate (FITC), Texas red, green fluorescent protein, rhodamines, tetramenthylrhodamine isothiocyanate (TRITC), 4,4-difluoro-4-bora-3a, 4a-diaza-s-indacene, lissamine,5'-carboxyfluorescein, 2',7'-dimethoxy-4',5'-dichloro-6 carboxy-fluorescein, phycoerythrin, Cy2, Cy3, Cy3.5, Cy5, Cy5.5, Cy7; enzymes such as alkaline phosphates, horse radish peroxidase; substrates; nucleotide chromophores; chemiluminescent moieties; bioluminescent moieties; phosphorescent compounds, magnetic particles. The analogues and derivatives also include natural peptide, polypeptide and protein which contained the chemical modifications or and substitutions on amino acid and or on its analogous structures which deviates from and within the said peptide, polypeptide and protein sequences. The said chemical modifications on amino acid and on its analogous include but are by no means limited to hydroxylation, methylation, acetylation, carboxylation and phosphorylation. It also includes the addition of lipids and carbohydrate polymers to the side chains of amino acid residues of the said peptides, polypeptides and proteins.

V. Standardized and Normalized cDNA Libraries

In one preferred embodiment, a cell line(s) to be tested and a corresponding control cell line(s) are synchronized in culture. Steady-state RNA is then isolated from the cell line(s) to be tested and the control cell line(s) and processed according to the protocols described by Chomczynski et al., Anal. Biochem. 162: 156-159, 1987; Ausuble et al., Current Protocols in Molecular Biology, 1987; all of which are incorporated herein by reference in their entirety for all purposes.

In one embodiment, the reverse transcriptase employed in the experiment was Moloney Murine Leukemia Virus (M-MuLV) reverse transcriptase (BioLabs Inc., Catalog, 2002-03). In one preferred embodiment, Oligo-(dT)$_{12}$ were used for priming the reverse transcription reaction. In one preferred embodiment, Oligo-(dT)$_{5}$ was used for priming in the reverse transcription reaction. In one preferred embodiment, Oligo-(dT)$_{18}$ was used for priming in the reverse transcription reaction. In one preferred embodiment, 5% of Oligo-(dT)$_{5}$ was mixed with 95% hexamer primers consisting of an approximately equal amount of each distinctive sense codon-based hexamer oligonucleotides represented by the algorithm of 61.sup.2, described above. The mixed primers were used for priming in the reverse transcription reaction. In one preferred embodiment, the said hexamer primers consist of equal amount of each said distinctive 3,721 sense codon-based hexamer oligonucleotides and were used for priming in the reverse transcription reaction. In another preferred embodiment, the said hexamers are represented by the formula 5'-$(C_S)_{n1}$-3', wherein n1=n2, and were used for priming in the reverse transcription reaction. In some embodiments, an oligonucleotide library, wherein oligonucleotides represented by the formula 5'-$(C_S)_{n1}$-3' was used for priming in the reverse transcription reaction. In other embodiments, an oligonucleotide library, wherein each of the oligonucleotides is represented by the formula 5'-$I_S(C_S)_{n1}$-3' were used for priming in the reverse transcription reaction. In another embodiment, 5% of Oligo-(dT)$_{12}$ was mixed with 95% oligonucleotides represented by the formula 5'-ls$(C_S)_{n1}$-3' according to the algorithm of 61.sup.(3−1), wherein the said n1 is 2; and the said mixed oligonucleotides were used for priming in the reverse transcription reaction. The reverse transcription protocols were performed as described by Reverse Transcription Protocols: A Guide to Methods and Applications, Academic Press, Inc., 1990; Sambrook et al., Molecular Cloning: A Laboratory Manual, Cold Spring Harbor Press, 1989; all of which is incorporated herein by reference in its entirety for all purposes.

The cDNA synthesized from each said reaction was analyzed by the inventive cDNA Quality Control Kit to ensure quality. The size of newly synthesized cDNA was analyzed on agarose gel after electrophoresis. The size selection range was set from 200 to 6,000 b.p. and above for subsequent processes. Another size selection range was set from 500 to 10,000 b.p. and above for subsequent processes. Each of the selected cDNA reaction solution was made into aliquots and stored at −20° C. The said aliquots of the said selected cDNA were used as DNA template in subsequent procedures and experiments.

The present invention provides 3,721 distinctive 9 mers 5'-ATG oriented oligonucleotides as 3,721 distinctive individual PCR upstream primers. With oligo-d(T)$_{12-15}$ as a common downstream primer, the trace amounts of each said selected cDNA molecule were further amplified by PCR in 3,721 respective PCR vials making the amount of each said selected cDNA molecule sufficient for subsequent procedures. The said subsequent procedures include but are by no means limited to insertion and ligation into a suitable vector. In one preferred embodiment, melting temperature (hereinafter Tm) of PCR primers has been adjusted by incorporation of LNA monomer(s) in their sequences. In other preferred embodiments, Tm of PCR primers has been adjusted to 40° C. by incorporation of LNA monomer(s) in their sequences. In another preferred embodiment, under reaction conditions of 60 mM salt and 2 uM primer and template DNA, Tm of PCR primers has been adjusted to 40° C. by incorporation of eight LNA monomer(s) for primers of 11.1% GC content; six LNA monomer(s) for primers of 22.2% GC content; four LNA monomer(s) for primers of 33.33% GC content; two LNA monomer(s) for primers of 44.44% GC content; one LNA monomer(s) for primers of 55.6% GC content; one LNA monomer(s) for primers of 66.7% GC content in the middle of the said primers; one LNA monomer(s) for primers of 77.8% GC content at the first nucleotide at 5'-end of said primers; and the said primers are 9 mers 5'-ATG oriented oligonucleotides represented by the formula 5'-$I_S(C_S)_{n1}$-3'. In yet another preferred embodiment, under reaction conditions of 60 mM salt and 2 uM primer and template DNA, Tm of PCR primers has been adjusted to 40° C. by incorporation of LNA monomer(s) to PCR upstream primers according to the GC content of each individual primer, the said primers are 9 mers 5'-ATG oriented oligonucleotides represented by the formula 5'-$I_S(C_S)_{n1}$-3' and oligo-d(T)$_{18}$ consisting of 18 consecutive of thymidine nucleotides is the common downstream primer. Each PCR has its own corresponding controls, such as a normal and/or control cDNA as PCR control templates. The entire set of the said 3,721 distinctive PCRs was performed in the GeneAmp PCR System 9600.

The said PCR amplified cDNA fragments form each PCR vial could be detected, selected, compared and isolated precisely with control samples in 1% Agarose gel stained by Ethidium Bromide. In one embodiment, the preferred selection standard of cDNA molecules for subsequent cloning procedure is set at a minimum size of 500 b.p. and above. In other embodiment, the preferred selection standard is set at the minimum size of 400 b.p. and above. In another embodiment, the preferred selection standard is set at the minimum size of 300 b.p. and above. In yet another embodiment, the preferred selection standard is set at the minimum size of 200 b.p. and above. The selected cDNA fragments are then excised from the gel and extracted. Each of the selected cDNA fragments could be either re-amplified by its original set of PCR primers for subsequent cloning or cloned directly by TA cloning technology known in the art. The vector which contained the insert could be a plasmid, cosmid, phagemid, phage DNA or any other DNA vectors capable of propagating autonomously with selection marker(s) such as tetracycline or ampicillin resistance in a host cell as known in the art. For example, Lambda gt11 or Lambda ZapII could be used for this purpose.

The vector amplified cDNA libraries could be further used as probe libraries in the construction of cDNA Arrays, cDNA Microarrays and Dot-blots. The benefits of using the said cDNA libraries as cDNA probe libraries are unprecedented. The said cDNA libraries could be duplicated and propagated routinely by one skilled in the art. The said cDNA libraries become a permanent and convenient resource for all suitable purposes. It enables all unknown sequences of a said cDNA library to form DNA Arrays directly. The said DNA Arrays could be used to interrogate the unknown samples. In contrast, all the current DNA Arrays technologies including DNA Microarrays require all cDNA probe sequences be pre-determined prior their deposition and immobilization on a solid surface to form the arrays. The said oligonucleotide sequences are all determined and known. Each of the said unknown cDNA sequences has been derived from a said corresponding known oligonucleotide via PCR. Once the sequence(s) of interest were identified through screening of the said unknown cDNA probes by hybridization, the sequence(s) of interest could be identified and cloned using the corresponding known oligonulceotide(s) as the upstream primer(s) with appropriate oligo-d$(T)_S$ as the downstream primer(s) in subsequent PCR aided cloning procedures which are known in the art.

In another embodiment, one of the said cDNAs from a specific sample was expressed to produce the corresponding peptide or protein using an expression vector in vitro using means apparent to one skilled in the art. The said peptides or proteins in turn were used as antigens alone and/or to produce the corresponding monoclonal or multiclonal antibodies by the means apparent to one skilled in the art. Those derived specific antigens or the corresponding antibodies were used respectively to form corresponding capture layers for protein microarrays or ELISA or other immunoassays by means which are known in the art. Once the peptide(s) or proteins of interest were identified through screening of the said unknown peptides or proteins as the ligands, the corresponding unknown cDNAs which encoded the peptide sequence(s) of the said ligands were identified at the same time. Once the said unknown cDNAs were identified, the known sequences of their corresponding oligonucleotides which were used as the upstream PCR primers for the production of the said unknown cDNAs were subsequently identified. The gene(s) of interest can be identified and cloned by using the corresponding known oligonucleotide(s) as the upstream primer(s) with appropriate oligo-d$(T)_S$ as the downstream primer(s) in subsequent PCR aided cloning procedures which are known in the art. Those embodiments demonstrated that the inventive standardized oligonucleotide libraries have the unique capacity to derive the corresponding cDNA probe and peptide ligand libraries for HTS platforms respectively. The current invention allows the sequencing information to be converted from DNA to protein and vice versa among different screening platforms. Additionally, the inventive method allowed the sequences to be determined only when it is necessary during the operation.

The strategy of using "unknown cDNA derived from the known oligonucleotide" to interrogate unknown sample is an efficient, fast and economical approach. The present invention attempts to standardize and integrate the three major HTS platforms at the levels of genome, transcriptome and proteome into one unified HTS system.

VI. Gene Expression Profiling, Fingerprinting and Cloning Aided by PCR

The method of Differential Display Reverse Transcription Polymerase Chain Reaction (DD-RT-PCR) uses a set of arbitrarily selected oligonucleotides as PCR primers to display differentially expressed cDNA (Liang et al., Science 257: 967-971, 1992) (Pardee et al., U.S. Pat. No. 5,262,311, 1993) (Welsh et al., Nucleic Acids Res. 18: 7213-7218, 1990) (Welsh et al., Nucleic Acids Res. 20: 4965-4970, 1992). A set of arbitrarily designed and selected PCR primers is unlikely to be unbiased. The primers were selected based on single nucleotide or base instead of on codons. The results found by others seem less than satisfying (Li et al., Nucleic Acids Res. 22: 1764-1765, 1994; Bertioli et al., Nucleic Acids Res. 23: 4520-4523, 1995; Shoham et al., Biotechniques 20: 182-183, 1996; Graf et al., Nucleic Acids Res. 25: 2239-2240, 1997 and MacLeod et al., U.S. Pat. No. 6,221,600, 1999). DD-RT-PCR as a method may only provide a partial analysis of cDNA fragments at best (Kinzler et al., U.S. Pat. No. 5,866,330, 1995). DD-RT-PCR adopted polyacrylamide gel as the display panel. However, cDNA fragments which can be efficiently identified and isolated from a 6% polyacrylamide gel after electrophoresis are usually less than 500 to 600 b.p in size in most of the cases. This sets a technical limitation for displaying and identifying the full length cDNA molecules in primary screening. Moreover, a considerable portion of those 500 to 600 b.p. sequences displayed may contain 3'-UTR sequences (Liang et al., Science 257: 969, 1992) (Pardee et al., U.S. Pat. No. 5,262,311, 1993). It is known in the art that targeting 3'-end regions of a gene often contributes to the noise-level in the subsequent cloning process. To circumvent those problems, the present invention presents a series of solutions wherein the said solutions are (1) to replace the shotgun strategy by systematic strategy. (2) to replace the tactics of targeting 3'-region by targeting 5'-region. (3) to replace nucleotide-based primer by codon-based primers. (4) to replace polyacrylamide gel by Agarose gel. (5) to elongate primer length by incorporation of universal base. (6) to increase and adjust Tm of primer by incorporation of LNA.

In one preferred embodiment, the present invention provides 3,721 distinctive 9 mers 5'-ATG oriented oligonucleotides as each individual PCR upstream primer and oligo-d $(T)_{12-15}$ as a common downstream primer for 3,721 distinctive PCRs. Each said PCR has its corresponding controls, such as a normal or control cDNA as PCR control template. Each of the said PCRs is in a separate vial. The final volume of each PCR is 20 ul. In one preferred embodiment, melting temperature of PCR primers has been adjusted by incorporation of LNA monomer(s) in their sequences. In another preferred embodiment, under reaction conditions of 60 mM salt and 2 uM primer and template DNA, Tm of 9 mers PCR primers has been adjusted to 40° C. by incorporation of eight LNA monomer(s) for primers of 11.1% GC content; six LNA monomer(s) for primers of 22.2% GC content; four LNA monomer(s) for primers of 33.33% GC content; two LNA monomer(s) for primers of 44.44% GC content; one LNA monomer(s) for primers of 55.6% GC content; one LNA monomer(s) for primers of 66.7% GC content in the middle of the said primers; one LNA monomer(s) for primers of 77.8% GC content at the first nucleotide at 5'-end of said primers; and the said primers are 9 mers 5'-ATG oriented oligonucleotides represented by the formula 5'-$I_S(C_S)_{n1}$-3'. In yet another preferred embodiment, under reaction conditions of 60 mM salt and 2 uM primer and template DNA, Tm of PCR primers has been adjusted to 40° C. by incorporation of LNA monomer(s) to PCR upstream primers according to the GC content of each individual primer, the said primers are 9 mers 5'-ATG oriented oligonucleotides represented by the formula 5'-$I_S(C_S)_{n1}$-3' and oligo-d(T)$_{18}$consisting of 18 consecutive thymidine nucleotides as the common downstream primer. Each PCR has its own corresponding controls, such as a normal and/or control cDNA as PCR control templates. The present invention emphasizes that each of the RNA or cDNA samples may have its corresponding normal or control samples which include positive and negative controls respectively at the same time in PCR experiments. Furthermore, at least one control for each testing sample is suggested. Each distinctive PCR should include all the necessary controls known in the art. Usually, a PCR testing product was loaded in parallel with the corresponding PCR control product(s) on two or more adjacent lanes on an Agarose gel prior to electrophoresis. As a result of this arrangement, the results of electrophoresis clearly demonstrate which of the PCR amplicons was specific for which samples. In one preferred embodiment, the entire set of the said 3,721 distinctive PCRs were performed on GeneAmp PCR System 9600 under suitable PCR conditions. Under UV light, each of the PCR products were detected, displayed and compared with each other on 1% Agarose gels stained by Ethidium Bromide. Photos were taken under the UV light for each said Agarose gels and recorded. The collections of those said photos provided a specific transcriptome file(s) or mRNA fingerprint(s) for a specific sample. The identity of a specific mRNA fingerprint(s) with a particular nucleic acid sample provides a PCR "genetic signature" of that sample. Subsequently, the said recorded PCR "genetic signature" provides a specific gene expression pattern(s) for further identification and analysis. Concerning the features of all-around spectrum and scale for mRNA screening and profiling, the current inventions offer an alternative solution.

Real-time PCR monitors the energy emission of excited fluorescence during PCR amplification whereas conventional PCR is focused on endpoint detection. One of the major advantages of Real-time PCR is the wider dynamic spectrum which is 10.sup.4 times more than conventional PCR. Real-time PCR has its own criteria for the selection of primers. The inventive codon-based standardized oligonucleotides suitable for this process. For example, 9 mers 5'-ATG oriented standardized oligonucleotide represented by the formula 5'-$I_S$ $(C_S)_{n1}$-3' has 3,721 distinctive 9 mers oligonucleotides. There is no G at the 5'-end. 86.9% of them are without runs of three or more Gs or $C_S$ or GCs at the 3'-end. 3,364 of the said 3,721 distinctive 9 mers oligonucleotides have GC content in the ideal range of 30-80%. That means 90.4% of the said 3,721 9 mers oligonucleotides are within the ideal GC content spectrum for Real-time PCR primers selection. 15 mers 5'-ATG oriented standardized oligonucleotide represented by the formula 5'-$I_S(C_S)_{n1}$-3' have the same proportional ratios as the said 9 mers regarding GC content and runs of three or more Gs, $C_S$ and GCs. Obviously, length elongated or Tm increased modified oligonucleotides from the said 9 mers oligonucleotides would be ideal for this process. The said derivative oligonucleotides include but are not by no means to be limited to the said 15 mers oligonucleotides or ones having longer length and/or higher Tm than the above 9 mers and 15 mers. The said primer length elongation methods include but are by no means limited to the incorporation of universal base. The said primer Tm increasing includes but is by no means limited to the incorporation of LNA.

Primer elongation is another important aspect of the present invention. In one preferred embodiment, one of the positive PCR amplicons at a time were chosen for further investigation after the primary PCR aided screening by using a pair of PCR primers such as, 5'-ATGGCAGCA and oligo-d(T)$_{15}$. Hence, 5'-ATGGCAGCA was identified and selected as the promising positive sequence or pre-determined sequence for the secondary screening. Each one of the 61 amino acid coding codons was covalently added on the 3'-end of each 5'-ATGGCAGCA respectively so that 61 distinct 12 mers oligonucleotides derived from 5'-ATGGCAGCA have been formed. 9 mers oligonucleotides have been elongated to 12 mers. Using each of 61 distinct 12 mers oligonucleotides as the upstream primer in conjunction with oligo-d(T)$_{18}$ as the common downstream PCR primer, 61 distinct PCRs with corresponding controls were performed. The products of the secondary screening were analyzed. One of the positive PCR amplicons at a time were chosen for further investigation after the said secondary screening by using a pair of PCR primers such as, 5'-ATGGCAGCATCG (SEQ ID No. 3) and oligo-d (T)$_{18}$; 5'-ATGGCAGCATCG (SEQ ID No. 3) was the promising positive sequence identified or pre-determined sequence for the third screening. Again, each one of the 61 amino acid coding codons was covalently added on the 3'-end of each 5'-ATGGCAGCATCG (SEQ ID No. 3) respectively to elongate the 12 mers to 15 mers. Using the 61 distinct 15 mers oligonucleotides as the upstream PCR primers in conjunction with oligo -d(T)$_{18}$ as the common downstream PCR primer, 61 distinct PCRs with corresponding controls were performed. The products of the third screening were analyzed. One of skill in the art could either use the deduced 15 mers oligonucleotide in conjunction with oligo-d(T)$_{18}$ to clone the gene of interest or further deduce out a new set of 61 distinct 18 mers oligonucleotides to increase the specificity of the primer for subsequent PCR screening by repeating the cycle once more. In other embodiments, PCR primer(s) were elongated by two additional codons at each time from the invented panel of 3,721 distinctive hexamer oligonucleotides represented by formula 5'-$(C_5)_{n1}$-3', wherein n1=2. In another embodiment, more than one of the positive PCR amplicons identified was chosen at a time for further investigation. The procedures will follow the procedures of precedent embodiments for each specified pairs of PCR primers of each specified pre-determined sequence. In one preferred embodiment, Tm of PCR 9 mers primers has been adjusted to 40° C. by incorporation of LNA monomer(s) in their sequences. In another preferred embodiment, under reaction conditions of 60 mM salt and 2 uM primer and template DNA, Tm of 9 mer PCR primers has been adjusted to 40° C. by incorporation of eight LNA monomer(s) for primers of 11.1% GC content; six LNA monomer(s) for primers of 22.2% GC content; four LNA monomer(s) for primers of 33.33% GC content; two LNA monomer(s) for primers of 44.44% GC content; one LNA monomer(s) for primers of 55.6% GC content; one LNA monomer(s) for primers of 66.7% GC content in the middle of the said primers; one LNA monomer(s) for primers of 77.8% GC content at the first nucleotide at 5'-end of said primers; and the said primers are 9 mers 5'-ATG oriented oligonucleotides represented by the formula 5'-$I_s(C_s)_{n1}$-3'. In yet another preferred embodiment, under reaction conditions of 60 mM salt and 2 uM primer and template DNA, Tm of PCR primers has been adjusted to 40° C. by incorporation of LNA monomer(s) to PCR upstream primers according to the GC content of each individual primer, the said primers are 9 mers 5'-ATG oriented oligonucleotides represented by the formula 5'-$I_s$ $(C_s)_{n1}$-3' and oligo -d$(T)_{18}$ consisting of 18 consecutive thymidine nucleotides as the common downstream primer.

In one preferred embodiment, three consecutive universal bases such as 5'-nitroindoles were added covalently and sequentially at the 3'-end of 5'-ATGGCAGCA which was one of the pre-determined sequences identified from a PCR aided screening. 5'-ATGGCAGCA has been elongated to a 12 mers oligonucleotide represented by 5'-ATGGCAGCA555 (SEQ ID No. 4), wherein 5, the numeral, represents 5'-nitroindole. Each one of 61 identical 5'-ATGGCAGCA555 (SEQ ID No. 4) oligonucleotides were then joined covalently with one distinct codon from the group of 61 codons such as 5'-GCA respectively to form 61 distinct 15 mers oligonucleotides such as, 5'-ATGGCAGCA555GCA (SEQ ID No. 5). Using the 61 distinct 15 mers oligonucleotides as the upstream primers in conjunction with oligo-d$(T)_{18}$ as the common downstream primer, 61 distinct PCRs with corresponding controls were processed. 61 distinctive sets of PCRs with 61 pairs of distinctive PCR primers have been performed. The 15 mers promising positive sequence(s) or 15 mers pre-determined sequence(s) was consequently identified. Since a "codon" consisting of three consecutive 5'-nitroindoles occupied the $4^{th}$ codon position within that 15 mers oligonucleotide in 5' towards 3' orientation; further determination of the $4^{th}$ codon position of that 15 mers oligonucleotide is needed. Using each one of the 61 codons to replace the "codon" consisting of three consecutive 5'-nitroindoles, another 61 distinctive 15 mers oligonucleotides without any 5'-nitroindole within the sequences were formed. Using the 61 newly formed distinctive 15 mer oligonucleotides as the upstream primers in conjunction with oligo-d$(T)_{18}$ as the common downstream primer, another set of 61 distinctive PCRs with corresponding controls were processed. Positive PCR amplicons were identified after the third PCR aided screening. Therefore, the positive 15 mers oligonucleotide sequence(s) was identified and determined. One of skill in the art could either use the deduced 15 mers oligonucleotide in conjunction with oligo-d$(T)_{18}$ to clone the gene of interest or further deduce out an 18 mers oligonucleotide to increase the specificity of the primer for subsequent PCR screening by repeating the cycle once more. In one preferred embodiment, Tm of PCR primers containing universal base(s) has been adjusted to 40° C. by incorporation of appropriate number of LNA monomer(s) in their sequences. In another preferred embodiment, under reaction conditions of 60 mM salt and 2 uM primer and template DNA, Tm of PCR primers containing universal base(s) has been adjusted to 40° C. by incorporation of appropriate number of LNA monomer(s) in their sequences. In yet another embodiment, Tm of PCR primers containing 5'-nitroindole(s) has been adjusted to 40° C. by incorporation of appropriate number of LNA monomer(s) in their sequences.

Some of the embodiments and examples mentioned above are generally known in the art and the artisan with the ordinary skill will recognize that the scope of the present invention is not limited to and by those said embodiments and examples. The present invention presents a technique of PCR primer sequence elongation and deduction. It deconvolves the ambiguous signals into unambiguous ones via a PCR platform. The described PCR primer elongating and deducing is a systematic approach.

The methods of Polymerase Chain Reaction (PCR) were invented by Mullis et al., U.S. Pat. Nos. 4,683,202; 4,683,195; 4,800,159; 4,965,188; Taq and AmpliTaq® DNA polymerases were covered by U.S. Pat. Nos. 4,889,818; 5,075,216; 5,079,352; the PCR protocols were performed as described by Innis et al. PCR Protocols: A Guide to Methods and Applications, Academic Press, Inc., 1990; Sambrook et al. Molecular Cloning: A Laboratory Manual, Cold Spring Harbor Press, 1989; all of which are incorporated herein by reference in their entirety for all purposes.

VII. Gene Expression Profiling, Fingerprint and Cloning by DNA Arrays and PCR

Regarding the construction of Oligonucleotide Arrays, there are two major formats. One is made by pre-synthesized oligonucleotides or oligonucleotide analogues; the other is made by in-situ synthesized oligonucleotides or oligonucleotide analogues.

1. Oligonucleotide Pre-Synthesis and Immobilization

In one preferred embodiment, the pre-synthesis of oligonucleotides was processed by the phoshoramidite methods such as Caruthers et al., Nucleic Acids Res. Symp. Ser. 7: 215-223, 1980; Beaucage et al., Tetrahedron Lett. 22: 1859-1862, 1981; McBride et al., Tetrahedron Lett. 24: 245-248, 1983; and Beaucage et al., Tetrahedron Lett. 48: 2223-2311, 1992; all of which are incorporated herein by reference in their entirety for all purposes. In one preferred embodiment, the pre-synthesis of oligonucleotides was processed by the H-phoshonate methods such as Garegg et al., Chem. Scripta 25: 280-282, 1985; Garegg et al., Chem. Scripta 26: 59-62, 1986; Garegg et al., Tetrahedron Lett. 27: 4051-4054, 1986; Froehler et al., Nucleic Acids Res., 14: 5399-5407, 1986; Froehler et al., Tetrahedron Lett. 27: 469-4472, 1986; Froehler et al., Tetrahedron Lett. 27: 5575-5578,1986; all of which are incorporated herein by reference in their entirety for all purposes.

In another preferred embodiment, the pre-synthesis of oligonucleotides was processed by an automated nucleic acid synthesizer such as, ABI 381-A, ABI 391, ABI 392, ABI 3900 and Expedite 8909 Nucleic Acid Synthesizer of PE Applied Biosystems at a 0.2 μm scale using standard protocols in accordance with the manual of the manufacturer.

Prior to the coupling step on the solid phase, the pre-synthesized oligonucleotides were purified, desalted and lyophilized at different grades of purity in accordance with different purposes such as PCR™-grade (ethanol precipitation to remove the salt), Probe-grade (purified by HPLC) or and Gene-synthesis-grade (purified by polyacrylamide gel electrophoresis). Such purification is well known to those of skill in the art.

In one embodiment, the pre-synthesized oligonucleotide was without universal bases such as 5'-nitroindole at its 5'-end. In another embodiment, the pre-synthesized oligonucleotide had one universal base such as 5'-nitroindole at its 5'-end. In another embodiment, the pre-synthesized oligonucleotide had two consecutive universal bases such as 5'-nitroindoles at its 5'-end. In another embodiment, the pre-synthesized oligonucleotide had three consecutive universal bases such as 5'-nitroindoles at its 5'-end. In another embodiment, the pre-synthesized oligonucleotide had four consecutive universal bases such as 5'-nitroindoles at its 5'-end. In another embodiment, the pre-synthesized oligonucleotide had five consecutive universal bases such as 5'-nitroindoles at its 5'-end. In another embodiment, the pre-synthesized oligonucleotide had six consecutive universal bases such as 5'-nitroindoles at its 5'-end.

In one preferred embodiment, the melting temperature of pre-synthesized oligonucleotide has been adjusted by incorporation of appropriate number of LNA monomer(s) in their sequences. In other preferred embodiment, Tm of pre-synthesized oligonucleotide has been adjusted to 40° C. by incorporation of an appropriate number of LNA monomer(s) in their sequences. In other preferred embodiments, Tm of pre-synthesized oligonucleotide has been adjusted between 40° C. to 50° C. under suitable hybridization conditions for oligonucleotide probe by incorporation of an appropriate number of LNA monomer(s) in their sequences. In one preferred embodiment, the incorporation of LNA and adjustment of pre-synthesized oligonucleotides have been performed according to the methods described by Beaucage et al., Tetrahedron Lett., 48(12) 2223-2311, 1992; Beaucage et al., Tetrahedron Lett., 49(28) 6123-6194, 1993; Imsnish et al., U.S. Pat. No. 6,268,490, 2001; Tolstrup et al., Nucleic Acids Res., 31: 3758-3762, 2003; all of which are incorporated herein by reference in their entirety for all purposes.

Generally, immobilizing the pre-synthesized oligonucleotides requires pre-treatment of the surfaces of glass and polystyrene with poly L-lysine in order to be ready for the immobilization. The immobilization was generally processed in a humid chamber at 37° C. for 12 hours or overnight. The pre-synthesized oligonucleotides for immobilization require pre-treatment to chemically modify either amino groups or sulfhydryl groups of the pre-synthesized oligonucleotide before the attachment to the solid phase. In one preferred embodiment, the pre-synthesized oligonucleotides were covalently tethered to the surface of the solid support such as pre-synthesized oligonucleotides with either a 5'-end or 3'-end amine modification covalently tethered to epoxysilane monolayer of the glass surface by forming amine linkage. The glass slides were then washed in distilled water and stored at 4° C. to be ready for hybridization as described by Beattie et al., Molecular Biotech. 4: 213-225, 1995; which is incorporated herein by reference in its entirety for all purposes.

In another preferred embodiment, the pre-synthesized oligonucleotides with 5'-phosphate modification were reacted with imidazole to form 5'-phosphormidazolide which was in turn coupled covalently with the surface through a phosphormidate bond as described by Chu et al., Nucleic Acids Res. 11: 6513-6529, 1983; which is incorporated herein by reference in its entirety for all purposes. In one preferred embodiment, the pre-synthesized oligonucleotide possesses a 5' amino group which was obtained by using N-trifluroacetyl-6-aminohexyl-2-cyanoethyl N',N'-diisopropyl-phosphoramidite (PE Applied Biosystems Inc.). The clean microscope glass slides were treated with 1% 3-aminopropyl trimethoxysilane with 95% acetone/distilled $H_2O$, subsequently washed with acetone and dried. The pre-treated glass slides were further treated with 0.2% 1.4-phenylene diisothiocyanate (PDC) in 10% pyridine/dimethyl formamide and washed by methanol and acetone as described by Guo et al., Nucleic Acids Res. 22: 5456-5465, 1994; which is incorporated herein by reference in its entirety for all purposes. In one preferred embodiment, biotinylated pre-synthesized oligonucleotides are immobilized to a streptavidin or avidin covalently coated surface by non-covalent attachment as described by Holmstron et al., Anal. Biochem., 209: 278-283, 1993; which is incorporated herein by reference in its entirety for all purposes.

2. Oligonucleotide In-Situ Synthesis and Immobilization

In one preferred embodiment, a solid support such as the surface of silicon was coated with photo-removable groups, and in-situ synthesis of oligonucleotides was processed by photolithographic methods. First, a specific defined discrete position was exposed to light for activation. Then, an activated nucleotide monomer was flooded to the surface for specific chemical coupling at that defined position. The array was made by successive cycles of deprotecting defined positions of the array by photolithography such as Fodor et al., Science 251: 767-773, 1991; Pease et al., Proc. Natl. Acad. Sci. U.S.A. 91: 5022-5026, 1994; Lockhart et al., Nat. Biotechnol. 14: 1675, 1996; Pirrung et al., U.S. Pat. No. 5,143,854, 1992; Fodor et al., U.S. Pat. No. 5,445,934, 1995; Fodor et al., U.S. Pat. No. 5,510,270, 1996; Fodor et al., U.S. Pat. No. 5,800,992, 1998; all of which are incorporated herein by reference in their entirety for all purposes.

In another preferred embodiment, a flexible linker with a hydroxyl group was coupled to the surface of glass plate via glycidoxypropyl silane and in-situ synthesis of oligonucleotides was initiated from the bound hydroxyl group. All the procedures were processed in accordance with methods as described by Southern et al., Genomic 13: 1008-1017, 1992; Maskos et al., Nucleic Acids Res. 20: 1679-1684, 1992; Southern et al., Nucleic Acids Res. 22: 1368-1373, 1994; all of which are incorporated herein by reference in their entirety for all purposes. In another embodiment, in-situ synthesis of oligonucleotides and deposition on the perfluorinated hydrophobic surface of silicon dioxide was processed by a robotic liquid dispenser such as ink-jet printer heads controlled by a piezoelectric droplet generator as described by Blanchard et al., Biosensors & Bioelectronics 11: 687-690; Wallace et al., U.S. Pat. No. 4,812,856; Hayes et al., U.S. Pat. No. 5,053,100; all of which are incorporated herein by reference in their entirety for all purposes.

In one embodiment, the in-situ synthesized oligonucleotide was without a universal base such as 5'-nitroindole at its 5'-end. In another embodiment, the in-situ synthesized oligonucleotide had one universal base such as 5'-nitroindole at its 5'-end. In another embodiment, the in-situ synthesized oligonucleotide had two consecutive universal bases such as 5'-nitroindoles at its 5'-end. In another embodiment, the in-situ synthesized oligonucleotide had three consecutive universal bases such as 5'-nitroindoles at its 5'-end. In another embodiment, the in-situ synthesized oligonucleotide had four consecutive universal bases such as 5'-nitroindoles at its 5'-end. In another embodiment, the in-situ synthesized oligonucleotide had five consecutive universal bases such as 5'-nitroindoles at its 5'-end. In another embodiment, the in-situ synthesized oligonucleotide was with six consecutive universal bases such as 5'-nitroindoles at its 5'-end.

3. 5'-terminal Sense Sequence Deducing Oligonucleotide Arrays

In one preferred embodiment, 9 mers 5'-ATG oriented standardized oligonucleotide library containing 3,721 distinct oligonucleotides have been used as probe library for the arrays. The said 9 mers library consists of seven GC Identical Panels to allow the suitable hybridization conditions for each. The said Panels are (1) Panel of 64 distinctive 9 mers oligonucleotide sets of 77.8% GC content, (2) Panel of 384 distinctive 9 mers oligonucleotide sets of 66.7% GC content, (3) Panel of 928 distinctive 9 mers oligonucleotide sets of 55.6% GC content, (4) Panel of 1,168 distinctive 9 mers oligonucleotide sets of 44.4% GC content, (5) Panel of 820 distinctive 9 mers oligonucleotide sets of 33.3% GC content, (6) Panel of 308 distinctive 9 mers oligonucleotide sets of 22.2% GC content and (7) Panel of 49 distinctive 9 mers oligonucleotide sets of 11.1% GC content. Each of the said seven entire Panels have been immobilized and distributed on seven or seven series distinctive suitable solid supports known in the art respectively. The said seven or seven series distinctive suitable solid supports have formed seven distinctive sub-arrays. In a preferred embodiment, each of the said panels includes all necessary and suitable positive and negative controls.

The results of screening the entire said seven distinctive sub-arrays with a given nucleic acids sample produced a corresponding transcriptome file(s) or mRNA fingerprints. The identity of a specific mRNA fingerprint(s) with a particular nucleic acid sample provides "genetic signature" of that sample. Subsequently, the recorded "genetic signature" provides a specific gene expression pattern(s) for further identification and analysis. Once the promising positive position(s) were identified after primary screening, the corresponding individual 9 mers oligonucleotide probe(s) were identified. The said identified 9 mers oligonucleotide probes can be elongated and used for the secondary screening. The said screening cycle can be repeated until the ambiguous signals have been deconvolved systematically into unambiguous ones via this arrays platform. The methods of probe elongation have been described by this application in section VI. Gene Expression Profiling, Fingerprinting and Cloning Aided by PCR.

In other embodiment, before immobilization the said seven entire Panels on the surfaces of seven or seven series distinctive suitable solid supports to form the said seven distinctive sub-arrays; each of the above 3,721 distinct 9 mers oligonucleotides have been covalently coupled to a linker consisting of three consecutive universal bases such as 5'-nitroindoles at its 5'-end to form 3,721 distinctive corresponding 12 mers oligonucleotides.

In another preferred embodiment, 12 mers 5'-ATG oriented standardized oligonucleotide library containing 226,981 distinct oligonucleotides have been used as probe library for the arrays. The said 12 mers library consists of ten GC Identical Panels to allow for the suitable hybridization conditions for each. The said Panels are (1) Panel of 512 distinctive 12 mers oligonucleotide sets of 83.3% GC content, (2) Panel of 4,608 distinctive 12 mers oligonucleotide sets of 75% GC content, (3) Panel of 18,048 distinctive 12 mers oligonucleotide sets of 66.7% GC content, (4) Panel of 40,512 distinctive 12 mers oligonucleotide sets of 58.3% GC content, (5) Panel of 57,696 distinctive 12 mers oligonucleotide sets of 50% GC content, (6) Panel of 54,336 distinctive 12 mers oligonucleotide sets of 41.7% GC content, (7) Panel of 34,000 distinctive 12 mers oligonucleotide sets of 33.3% GC content, (8) Panel of 13,692 distinctive 12 mers oligonucleotide sets of 25% GC content, (9) Panel of 3,234 distinctive 12 mers oligonucleotide sets of 16.7% GC content and (10) Panel of 343 distinctive 12 mers oligonucleotide sets of 8.3% GC content. Each of the said ten entire Panels have been immobilized and distributed on the surfaces of ten or ten series distinctive suitable solid supports known in the art respectively. The said ten or ten series distinctive suitable solid supports have formed ten distinctive sub-arrays. Each of the said panels includes all necessary and suitable positive and negative controls known in the art.

The results of screening the entire said ten distinctive sub-arrays with a given nucleic acids sample produced a corresponding transcriptome file(s) or mRNA fingerprints. The identity of a specific mRNA fingerprint(s) with a particular nucleic acid sample provides an "genetic signature" of that sample. Subsequently, the recorded "genetic signature" provides a specific gene expression pattern(s) for further identification and analysis. Once the promising positive position(s) were identified after primary screening, the corresponding individual 12 mers oligonucleotide probe(s) were identified. The said identified 12 mers oligonucleotide probes could be elongated and used for secondary screening. The said screening cycle could be repeated until the ambiguous signals have been deconvolved systematically into unambiguous ones via this arrays platform. The methods of probe elongation have been described by this application in section VI. Gene Expression Profiling, Fingerprinting and Cloning Aided by PCR.

In other embodiments, before immobilization the said ten entire Panels on the surfaces of ten or ten series distinctive suitable solid supports to form the said ten distinctive sub-arrays; each of the above 226,981 distinct 12 mers oligonucleotides have been covalently coupled to a linker consisting of three consecutive universal bases such as 5'-nitroindoles at its 5'-end to form 226,981 distinctive corresponding 15 mers oligonucleotides.

In yet another preferred embodiment, 15 mers 5'-ATG oriented standardized oligonucleotide library containing 13,845,841 distinct oligonucleotides have been used as probe library for the arrays. The said 15 mers library consists of thirteen GC Identical Panels to allow the suitable hybridization conditions for each. The said Panels are (1) Panel of 4,096 distinctive 15 mers oligonucleotide sets of 86.7% GC content, (2) Panel of 49,152 distinctive 15 mers oligonucleotide sets of 80% GC content, (3) Panel of 266,240 15 mers distinctive oligonucleotide sets of 73.3% GC content, (4) Panel of 862,208 distinctive 15 mers oligonucleotide sets of 66.7% GC content, (5) Panel of 1,863,168 distinctive 15 mers oligonucleotide sets of 60% GC content, (6) Panel of 2,836,992 distinctive 15 mers oligonucleotide sets of 53.3% GC content, (7) Panel of 3,128,960 distinctive 15 mers oligonucleotide sets of 46.7% GC content, (8) Panel of 2,524,800 distinctive 15 mers oligonucleotide sets of 40% GC content, (9) Panel of 1,482,832 distinctive 15 mers oligonucleotide sets of 33.3% GC content, (10) Panel of 619,584 distinctive 15 mers oligonucleotide sets of 26.7% GC content, (11) Panel of 175,224 distinctive 15 mers oligonucleotide sets of 20% GC content, (12) Panel of 30,184 distinctive 15 mers oligonucleotide sets of 13.3% GC content and (13) Panel of 2,401 distinctive 15 mers oligonucleotide sets of 6.7% GC content. Each of the said thirteen entire Panels have been immobilized and distributed on the surfaces of thirteen or thirteen series distinctive suitable solid supports known in the art respectively. The said thirteen or thirteen series distinctive suitable solid supports have formed thirteen distinctive sub-arrays. Each of the said panels includes all necessary and suitable positive and negative controls known in the art.

The results of screening the entire said thirteen distinctive sub-arrays with a given nucleic acids sample produced a corresponding transcriptome file(s) or mRNA fingerprint. The identity of a specific mRNA fingerprint(s) with a particular nucleic acid sample provides a "genetic signature" of that sample. Subsequently, the recorded "genetic signature" provides a specific gene expression pattern(s) for further identification and analysis. Once the promising positive position(s) were identified after the entire primary screening, the corresponding individual 15 mers oligonucleotide probe(s) were identified. The said identified 15 mers oligonucleotide probes could be elongated and used for the secondary screening. The said screening cycle could be repeated until the ambiguous signals have been deconvolved systematically into unambiguous ones via this arrays platform. The methods of probe elongation have been described by this application in section VI. Gene Expression Profiling, Fingerprinting and Cloning Aided by PCR.

In other embodiments, before immobilization the said thirteen entire Panels on the surfaces of thirteen or thirteen series distinctive suitable solid supports to form the said thirteen distinctive sub-arrays; each of the above 13,845,841 distinct 15 mers oligonucleotides have been covalently coupled to a linker consisting of three consecutive universal bases such as 5'-nitroindoles at its 5'-end to form 13,845,841 distinctive corresponding 18 mers oligonucleotides.

In yet another preferred embodiment, 18 mers 5'-ATG oriented standardized oligonucleotide library containing 844,596,301 distinct oligonucleotides have been used as probe library for the arrays. The said 18 mers library consists of sixteen GC Identical Panels to allow the suitable hybridization conditions for each. The said Panels are (1) Panel of 32,768 distinctive 18 mers oligonucleotide sets of 88.9% GC content, (2) Panel of 491,520 distinctive 18 mers oligonucleotide sets of 83.3% GC content, (3) Panel of 3,399,680 18 mers distinctive oligonucleotide sets of 77.8% GC content, (4) Panel of 14,397,440 distinctive 18 mers oligonucleotide sets of 72.2% GC content, (5) Panel of 41,799,680 distinctive 18 mers oligonucleotide sets of 66.7% GC content, (6) Panel of 88,244,224 distinctive 18 mers oligonucleotide sets of 61.1% GC content, (7) Panel of 140,144,640 distinctive 18 mers oligonucleotide sets of 55.6% GC content, (8) Panel of 170,749,440 distinctive 18 mers oligonucleotide sets of 50% GC content, (9) Panel of 161,153,920 distinctive 18 mers oligonucleotide sets of 44.4% GC content, (10) Panel of 117,992,960 distinctive 18 mers oligonucleotide sets of 38.9% GC content, (11) Panel of 66,567,712 distinctive 18 mers oligonucleotide sets of 33.3% GC content, (12) Panel of 28,457,520 distinctive 18 mers oligonucleotide sets of 27.8% GC content, (13) Panel of 8,935,640 distinctive 18 mers oligonucleotide sets of 22.2% GC content, (14) Panel of 1,948, 240 distinctive 18 mers oligonucleotide sets of 16.7% GC content, (15) Panel of 264,110 distinctive 18 mers oligonucleotide sets of 11.1% GC content and (16) Panel of 16,807 distinctive 18 mers oligonucleotide sets of 5.6% GC content. Each of the said sixteen entire Panels have been immobilized and distributed on the surfaces of sixteen or sixteen series distinctive suitable solid supports known in the art respectively. The said thirteen or thirteen series distinctive suitable solid supports have formed sixteen distinctive sub-arrays. Each of the said panels includes all necessary and suitable positive and negative controls known in the art.

The results of screening the entire said sixteen distinctive sub-arrays with a given nucleic acids sample produced a corresponding transcriptome file(s) or mRNA fingerprint. The identity of a specific mRNA fingerprint(s) with a particular nucleic acid sample provides a "genetic signature" of that sample. Subsequently, those said recorded "genetic signature" provides a specific gene expression pattern(s) for further identification and analysis. Once the promising positive position(s) were identified after the entire primary screening, the corresponding individual 18 mers oligonucleotide probe(s) were identified. The said identified 18 mers oligonucleotide probes could be elongated and used for the secondary screening. The said screening cycle could be repeated until the ambiguous signals have been deconvolved systematically into unambiguous ones via this arrays platform. The methods of probe elongation have been described by this application in section VI. Gene Expression Profiling, Fingerprinting and Cloning Aided by PCR.

In other embodiments, before immobilization the said sixteen entire Panels on the surfaces of sixteen or sixteen series distinctive suitable solid supports to form the said sixteen distinctive sub-arrays; each of the above 844,596,301 distinct 18 mers oligonucleotides have been covalently coupled to a linker consisting of three consecutive universal bases such as 5'-nitroindoles at its 5'-end to form 844,596,301 distinctive corresponding 21 mers oligonucleotides. In one-preferred embodiment, the Tm of oligonucleotides has been adjusted by incorporation of appropriate number of LNA monomer(s) in their sequences. In other preferred embodiments, the Tm of oligonucleotides has been adjusted to 40° C. by incorporation of an appropriate number of LNA monomer(s) in their sequences. In other preferred embodiments, the Tm of oligonucleotides has been adjusted between 40° C. to 50° C. under suitable hybridization conditions for oligonucleotide probe by incorporation of an appropriate number of LNA monomer(s) in their sequences.

After hybridization with RNA or cDNA or DNA sample(s), the positive position(s) were identified. Therefore the positive candidate sequence(s) of oligonucleotide(s) with the length of 3 codons (9 mers), 4 codons (12mers), 5 codons (15 mers) and 6 codons (18 mers) were identified and determined respectively according to the above methods. Using those said identified oligonucleotides as the upstream primers together with oligo-d(T)$_{12}$ or oligo-d(T)$_{15}$ or oligo-d(T)$_{18}$ respectively as the downstream primer, the sequence(s) of the genes of interest could be identified, amplified and eventually cloned by means known in the art. The PCR and cloning procedures were carried out as described by Innis et al. PCR Protocols: A Guide to Methods and Applications, Academic Press, Inc., 1990; and Sambrook et al. Molecular Cloning: A Laboratory Manual, Cold Spring Harbor Press, 1989; all of which are incorporated herein by reference in their entirety for all purposes.

4. 3'-Terminal Sense Sequence Deducing Oligonucleotide Arrays

As the counterpart of 5'-terminal sense ORF sequence deducing strategy, 9 mers 3'-stop codon oriented sense ORF oligonucleotide library provide a unique probing system to identify, deduce and determine the sequence of the first three consecutive codon sequences from 5'-TGA or 5'-TAG or 5'-TAA and upstream of at the 3'-end of the target sequence. As discussed above, the said 3'-stop codon oriented oligonucleotide probe libraries were also classified into several GC Identical Panels. In one embodiment, 9 mers 5'-TGA oriented sense ORF oligonucleotide library containing 3,721 distinctive oligonucleotides and was classified into seven GC Identical Panels. Each of the said seven Panels have been immobilized and distributed on seven or seven series distinctive suitable solid supports known in the art respectively. The said seven or seven series distinctive suitable solid supports have formed seven distinctive sub-arrays. Each of the said panels includes all necessary and suitable positive and negative controls.

In one preferred embodiment, Tm of oligonucleotide has been adjusted by incorporation of appropriate number of LNA monomer(s) in their sequences. In other preferred embodiments, the Tm of the oligonucleotide has been adjusted to 40° C. by incorporation of appropriate number of LNA monomer(s) in their sequences. In other preferred embodiments, the Tm of the oligonucleotide has been adjusted in the range between 40° C. to 50° C. under suitable hybridization conditions for oligonucleotide probe by incorporation of appropriate number of LNA monomer(s) in their sequences.

After hybridization with RNA or cDNA or DNA sample(s), the positive position(s) was identified. The positive candidate sequence(s) of oligonucleotide(s) such as, 5'-GCACTGTGA-3' were identified and determined. Using those oligonucleotides as the common downstream primer(s) together with any relevant pre-determined or previously available sequence of similar length such as promoter, consensus sequence, or motif sequence respectively as the upstream primer, the sequence(s) of the gene(s) of interest could be identified, amplified and eventually cloned in the subsequent PCR aided cloning procedures. Those methods are well known to one of ordinary skill in the art.

The results of the screening the entire said seven distinctive sub-arrays with a given nucleic acids sample produced a corresponding transcriptome file(s) or mRNA fingerprints. The identity of a specific mRNA fingerprint(s) with a particular nucleic acid sample provides a "genetic signature" of that sample. Subsequently, the recorded "genetic signature" provides a specific gene expression pattern(s) for further identification and analysis as well.

5. 5'-Two-Codon of Restriction Endonuclease Recognition Sense Sequence Oriented Oligonucleotide Arrays for Quantitative Analysis of Gene Expression (QAGE)

The amplified Restriction Fragment Length Polymorphism based mRNA fingerprinting had a higher percentage of reproducibility than DD-RT-PCR (Habu et al., Biochemical and Biophysical Research Communications 234: 519, 1997). To measure global gene expression quantitatively, the method of Serial Analysis of Gene Expression (SAGE) provided a well-recognized tool as an alternative of DNA Microarrays (Velculescu et al., Science 270: 484-487, 1995) (Kinzler et al., U.S. Pat. No. 5,866,330, 1995) (Zhang et al., Science 276:1270-1271, 1997) (MacLeod et al., U.S. Pat. No. 6, 221, 600, 1999). SAGE consists of a series of procedures including immobilizing cDNA on streptavidin beads prior to restriction endonuclease digestion. The tags are PCR amplified and ligated into multiple tags within a single clone. The individual clones consisting of the said tags were selected and subsequently sequenced. The numbers of the said tags were counted for quantitative analysis of gene expression. Further development of SAGE has been explored in recent years (Lal et al., Cancer Research 59: 5403-5407, 1999). The tag sequences as well as 4 b.p. restriction endonuclease recognition sites were all selected based on single nucleotide or base instead of codon (Kinzler et al., U.S. Pat. No. 5,866,330, 1999). In practice, for a favourable enzymatic reaction, such as ligation, several influential factors, such as substrates, AG and the conformation of active sites, may need to be coordinated and optimized according to the enzyme dynamic mechanisms. Those enzymatic procedures including PCR may produce certain selection pressures which may in turn impact the fidelity of subsequent gene analysis. Generally speaking, more manipulation of cDNA with enzyme reactions may create more opportunities of introducing artefacts and errors if one of those factors is not optimized.

The present invention aims at minimizing enzyme reactions involved, eliminating sequencing procedures, rationalizing tag sequence and standardizing tag libraries for analysis. The present invention has created codon-based QAGE tag sequence libraries. The introduction of DNA array platforms to the methods of Quantitative Analysis of Gene Expression (QAGE) offers an effective vehicle for gene expression analysis. QAGE employs restriction endonucleases having two-codon recognition site instead of restriction endonucleases of 4 b.p. recognition sites used in SAGE. For the convenience of operation, the QAGE tag sequence libraries have been generated according to the algorithm of 64.sup.(n−2). The oligonucleotides of each tag libraries have been further classified according to GC content into GC Identical Panels which have been further adjusted to a Tm value by the incorporation of appropriate number of LNA. In one preferred embodiment, Tm of oligonucleotide has been adjusted by incorporation of an appropriate number of LNA monomer(s) in their sequences. In other preferred embodiments, Tm of oligonucleotide has been adjusted to 40° C. by incorporation of an appropriate number of LNA monomer(s) in their sequences. In other preferred embodiments, Tm of oligonucleotide has been adjusted in the range between 40° C. to 50° C. under suitable hybridization conditions for oligonucleotide probe by incorporation of an appropriate number of LNA monomer(s) in their sequences.

In one preferred embodiment, the present invention presents a 15 mers 5'-GGATCC (BamH I) oriented QAGE sense standardized oligonucleotide library containing 262,144 distinct 15 mers oligonucleotide probes. The said 15 mers QAGE oligonucleotide library has been used as probe library for the QAGE DNA arrays. The said 15 mers QAGE library consists of ten GC Identical QAGE Panels to allow suitable hybridization conditions for each. The said Panels are (1) Panel of 512 distinctive 15 mers oligonucleotide sets of 86.7% GC content, (2) Panel of 4,608 distinctive 15 mers oligonucleotide sets of 80% GC content, (3) Panel of 18,432 distinctive 15 mers oligonucleotide sets of 73.3% GC content, (4) Panel of 43,008 distinctive 15 mers oligonucleotide sets of 66.7% GC content, (5) Panel of 64,512 distinctive 15 mers oligonucleotide sets of 60% GC content, (6) Panel of 64,512 distinctive 15 mers oligonucleotide sets of 53.3% GC content, (7) Panel of 43,008 distinctive 15 mers oligonucleotide sets of 46.7% GC content, (8) Panel of 18,432 distinctive 15 mers oligonucleotide sets of 40% GC content, (9) Panel of 4,608 distinctive 15 mers oligonucleotide sets of 33.3% GC content and (10) Panel of 512 distinctive 15 mers oligonucleotide sets of 26.7% GC content. Each of the said panels includes all necessary and suitable positive and negative controls known in the art.

In one preferred embodiment, 5 ug poly (A) RNA was selected for each test and control from total RNA of cells of choice. cDNA were synthesized with biotinylated oligo-d(T)$_s$. Synthesized cDNAs of test and control were incorporated with two different fluorescent dyes during reverse transcription reaction and then attached to magnetic beads via biotin respectively. RNA isolated from the test sample(s) was incorporated with the red-fluorescent dye Cy5 during the reverse transcription reaction while RNA isolated from the reference sample(s) was incorporated with the green-fluorescent dye Cy3 (BioDirectory, Amersham Pharmacia Biotech, 2001). Before hybridization, the cDNA sample with Cy5 labelling was mixed with its reference cDNA sample with Cy3 labelling at equal amounts. Using two-color fluorescent probes in hybridization with DNA Arrays was processed as described by Schena et al., Proc. Natl. Acad. Sci. U.S.A. 93: 10614-10619, 1996 and Shalon et al., Genome Res. 6: 639-645, 1996; all of which are incorporated herein by reference in their entirety for all purposes.

The said cDNAs of test and control were collected by means of centrifugation in accordance with the protocols known in the art. Both cDNA samples were collected again by repeating the previous procedures after the digestions with BamHI. Fill-in reactions were performed with Klenow Fragment for blunt-ends generation on dsDNA fragments with 5'-overhangs. Both cDNA of test and control were released from the magnetic beads by changing the ironic strength and temperature in the solutions respectively. The two said sample cDNAs were used in subsequent hybridization at the equal amount. The said cDNAs hybridized with QAGE Oligo GC Identical BamH I Panels. All the performance was processed as described by Sambrook et al., Molecular Cloning: A Laboratory Manual, Cold Harbor Laboratory, Cold Spring Harbor, 1989; Velculescu et al., Science 270: 484487, 1995; all of which are incorporated herein by reference in their entirety for all purposes.

In another preferred embodiment, the results of the hybridization with the said seven distinctive GC Identical Panels of 12 mers QAGE BamH I arrays reviewed a corresponding transcriptome file(s) or mRNA fingerprints. The identity of a specific mRNA fingerprint(s) with a particular nucleic acid sample provides a "genetic signature" of that sample. The methods provide a vehicle of quantitative measurement of gene expression.

To detect gene expression, 12 mers 5'-two-codon-restriction-endonuclease recognition-site orientated oligonucleotide probes provide a unique probing system to identify, deduce and determine the sequence of the first four consecutive codons downstream from a 5'-two-codon-restriction-endonuclease-recognition site of the target sequence through hybridization. All procedures and strategies for 5'-terminal Sense Sequence Deducing Oligonucleotide Arrays and PCR Aided Cloning are applicable herein.

Using those said identified oligonucleotides as the upstream primers together with oligo-d(T)$_{18}$ as the downstream primer, the genes of interest could be identified, amplified and eventually cloned in the subsequent PCR aid cloning procedures as described above.

6. The Sense Sequence Deducing Oligonucleotide Arrays

Nucleic acids could be sequenced by hybridizing them to oligonucleotide arrays (Chetverin et al., Bio/Technol. 12: 1093-1099, 1994) (Baringa Science 253:1489, 1991). In one preferred embodiment, 9 mers ORF sense standardized oligonucleotide represented by the formula 5'-$(C_S)_{n1}$-3' wherein n=3 containing 226,981 distinct 9 mers oligonucleotides. In one preferred embodiment, the said entire 9 mers oligonucleotide library has been used as the entire probe library for the arrays. The said 9 mers library consists of ten GC Identical Panels to allow the suitable hybridization conditions for each. The said Panels are (1) Panel of 512 distinctive 9 mers oligonucleotide sets of 100% GC content, (2) Panel of 4,608 distinctive 9 mers oligonucleotide sets of 88.9% GC content, (3) Panel of 18,048 distinctive 9 mers oligonucleotide sets of 77.8% GC content, (4) Panel of 40,512 distinctive 9 mers oligonucleotide sets of 66.7% GC content, (5) Panel of 57,696 distinctive 9 mers oligonucleotide sets of 55.6% GC content, (6) Panel of 54,336 distinctive 9 mers oligonucleotide sets of 44.4% GC content, (7) Panel of 34,000 distinctive 9 mers oligonucleotide sets of 33.3% GC content, (8) Panel of 13,692 distinctive 9 mers oligonucleotide sets of 22.2% GC content, (9) Panel of 3,234 distinctive 9 mers oligonucleotide sets of 11.1% GC content and (10) Panel of 343 distinctive 9 mers oligonucleotide sets of 0% GC content. Each of the said ten entire Panels have been immobilized and distributed on the surfaces of ten or ten series distinctive suitable solid supports known in the art respectively. The said ten or ten series distinctive suitable solid supports have formed ten distinctive sub-arrays. Each of the said panels includes all necessary and suitable positive and negative controls known in the art.

In one preferred embodiment, Tm of oligonucleotide has been adjusted by incorporation of appropriate number of LNA monomer(s) in their sequences. In other preferred embodiment, Tm of oligonucleotide has been adjusted to 40° C. by incorporation of appropriate number of LNA monomer(s) in their sequences. In other preferred embodiment, Tm of oligonucleotide has been adjusted in the range between 40° C. to 50° C. under the suitable hybridization conditions for oligonucleotide probe by incorporation of appropriate number of LNA monomer(s) in their sequences.

The sequence(s) could be determined by hybridization with a single suitable labelled target to the each of the said ten distinctive 9 mers oligonucleotide sub-arrays under individual optimized hybridization conditions per sub-array as described by Khrapko et al., DNA Sequencing and Mapping, 1:375-388, 1991; which is incorporated herein by reference in its entirety for all purposes. The oligonucleotide arrays formation, hybridization conditions, signal detection and sequence analysis were as described by Southern et al., Genomics 13: 1008-1017, 1992 and Macevicz U.S. Pat. No. 5,002,867, 1991; all of which are incorporated herein by reference in their entirety for all purposes.

7. The Oligonucleotide Derived cDNA Arrays

In general, using cDNA Arrays usually produces less cross-hybridization than Oligonucleotide Arrays. Moreover, once a cDNA library is obtained, it can be used as a permanent resource for duplication. For the convenience of operation, the present invention has established the corresponding relationship between the two. A specific cDNA library could be derived and produced from the original corresponding oligonucleotide library as described in the section V. Standardized and Normalized cDNA Libraries of this application.

In one preferred embodiment, the coupling of the said cDNA molecules to the solid phase was processed by printing on the pre-treated glass plates as described by Schena et al., Science 270: 467-470, 1995; Schena et al., Proc. Natl. Acad. Sci. U.S.A. 93: 10614-10619, 1996; DeRisi et al., Nat. Genet.: 14: 457-460, 1996; all of which are incorporated herein by reference in their entirety for all purposes. Each of the said the pre-treated glass plates may include all necessary and suitable positive and negative controls.

In one embodiment, RNA had been isolated independently from individual sources such as cell lines, tissues, organs etc. or from the same individual source but in a different time series after a specific treatment was given. RNA isolation and reverse transcription was carried out as described herein. RNA isolated from the test sample(s) was incorporated with the red-fluorescent dye Cy5 during the reverse transcription reaction while RNA isolated from the reference sample(s) was incorporated with the green-fluorescent dye Cy3 (Bio-Directory, Amersham Pharmacia Biotech, 2001). Before hybridization, the cDNA sample with Cy5 labelling was mixed with its corresponding cDNA sample with Cy3 labelling at equal amounts. Using two-color fluorescent probes in hybridization with DNA Arrays was processed as described by Schena et al., Proc. Natl. Acad. Sci. U.S.A. 93: 10614-10619, 1996 and Shalon et al., Genome Res. 6: 639-645, 1996; all of which are incorporated herein by reference in their entirety for all purposes.

The results of the screening the entire said cDNA Arrays with a given nucleic acids sample produced a corresponding transcriptome file(s) or mRNA fingerprints. The identity of a specific mRNA fingerprint(s) with a particular nucleic acid sample provides a "genetic signature" of that sample. Subsequently, those said recorded "genetic signature" provides a specific gene expression pattern(s) for further identification and analyzing as well.

The positive position(s) identified in the hybridization were the positive candidate cDNA molecule(s). Since each cDNA molecule was derived and produced from its corresponding oligonucleotide in PCR aided normalized cDNA library construction, the sequence(s) of the corresponding oligonucleotide(s) were known. Therefore, the corresponding oligonulceotides were identified as well. Using those said identified oligonucleotides as the upstream primers together with oligo-d(T)$_{18}$ as the downstream primer, the genes of interest could be identified, amplified and eventually cloned in the subsequent PCR aid cloning procedures as described above.

8. Dot-Blot DNA Arrays

Dot-blotting is another format of DNA arrays. Although the probe density is relative low compare with the high density DNA Microarrays, it is much more convenient for manual management in laboratory operation. Its radioisotope labelling is at least 10 times more sensitive than fluorescence labelling. Dot-blots of nylon and nitrocellulose filters may be reused after the hybridization signals were stripped. It is a well-established standard laboratory method with straightforward procedures. The performance does not require expensive equipment such as a laser scanner. Lennon et al. have revealed how Dot-Blotting Hybridization could be employed to exploit the data of genome programs on a large-scale manner (Lennon et al., Trends Genet.7: 314-317, 1991). To develop a new generation of Dot-Blotting with codon-based oligonucleotide probe libraries is one of the objectives of the present invention. In one preferred embodiment, oligonucleotides are classified according to GC content into GC Identical Panels which have been further adjusted to a Tm value by the incorporation of appropriate number of LNA. In one preferred embodiment, Tm of oligonucleotide has been adjusted by incorporation of appropriate number of LNA monomer(s) in their sequences. In other preferred embodiment, Tm of oligonucleotide has been adjusted to 40° C. by incorporation of appropriate number of LNA monomer(s) in their sequences. In other preferred embodiment, Tm of oligonucleotide has been adjusted in the range between 40° C. to 50° C. under the suitable hybridization conditions for oligonucleotide probe by incorporation of appropriate number of LNA monomer(s) in their sequences.

Each of the said panels includes all necessary and suitable positive and negative controls known in the art. In the other preferred embodiment, the oligonucleotide derived cDNA Dot-blots could be produced according to the same protocols as discussed above. The said cDNA Dot-blots includes all necessary and suitable controls containing positive and negative controls known in the art.

Overall, the methods of preparing, fabricating, operating and applying both oligonucleotide arrays and cDNA arrays ranging from oligonucleotides themselves to their corresponding derived cDNAs molecules; the methods of immobilization, sample labelling, hybridization, hybridization signal scan and signals' detection include, but are by no means to be limited to U.S. Pat. Nos. 5,242,974; 5,384,261; 5,405,783; 5,412,087; 5,424,186; 5,429,807; 5,436,327; 5,445,934; 5,472,672; 5,510,270; 5,527,681; 5,529,756; 5,545,531; 5,554,501; 5,556,752; 5,561,071; 5,599,895; 5,624,711; 5,639,603; 5,658,734; 5,700,637; 5,800,992; 5,807,522; 6,057,100; 6,197,506; 6,309,823; 6,337,188; 6,344,316; 6,352,828; 6,403,957; 6,406,921; U.S. Pat. Application Nos. 20010005588; 20020006622; 20020015949; 20020051981; 20020064482; 20020072060; all of which are incorporated herein by reference in their entirety for all purposes.

VIII. Gene Expression Profiling, Fingerprint and Cloning by ELISA and PCR

In comparison with protein microarrays, ELISA screening is manually manageable. It is a well-established standard laboratory method. It has simple and straightforward procedures with high reliability. To perform ELISA screening does not require expensive equipment such as a laser scanner. Pre-coated ELISA plates could be produced massively by robot technology. ELISA platform is actually a miniaturized protein microarray with low cost.

Enzyme Linked Immunoassay (ELISA) is one of the standard amplification methods to detect and display the presence of Antigen-antibody complex. Particularly, it has been used widely to measure antibody titers of clinical samples collected from serum, urine and culture supernatant at ng/ml to pg/ml sensitivity. Regarding simplicity, safety and specificity, ELISA is superior to the standard serological protocols and most of the immunoassays in both clinical and research applications. Generally, the typical epitope could consist of a hexa-peptide or more and be recognized by the corresponding monoclonal antibody such as, Anti-His(C-term) Antibody. (Invitrogen, Catalogue 2001) Even the antibody which binds the specific penta-peptide with nanomolar affinity has been demonstrated and introduced in Microarrays technology (Meo et al., Proc. Natl. Acad. Sci. U.S.A. 80: 4084, 1983) (Fodor et al., Science 251: 767-773, 1991). ELISA protocoles as described by Perlmann et al., Enzyme-linked Immuosorbent Assay, Academic Press, Inc., 1994; Harlow et al., Antibodies: A Laboratory Mannual, Cold Spring Harbor Laboratory Press, 1988; all of which are incorporated herein by reference in their entirety for all purposes.

A series of two-amino-acids restriction-enzyme-recognition-site oriented standardized peptide libraries provide a unique miniaturized immobilized capture epitope platforms which is pre-coated on the surface of ELISA plates such as high binding polystyrene plates. Those could be used to identify, deduce and determine the sequence of the epitopes from positively displayed antigen-antibody complex. The sequences of the identified epitopes could be further deduced into a set of corresponding sequences of oligonucleotides. Using the anti-sense oligonucleotides of those deduced sequences as the downstream primers and the sense ORF oligonucleotide of 5'-ATG orientation such as 9 mers sense ORF oligonucleotide library of 5'-ATG orientation comprising 3,721 distinct oligonucleotides as the upstream primers, the candidate sequences of genes of interest with 5'-orientation could be detected and identified in PCR. Using those deduced oligonucleotides as the upstream primers and oligo-$d(T)_{18}$ as the downstream primer, the candidate sequences of gene of interest with 3'-orientation could be detected and identified by PCR. Those sequences could be further displayed on Agarose gel and isolated for subsequent cloning and processing respectively. Sequencing analysis would determine all the candidate sequences of the 5'-portion and 3'-portion of the gene of interest respectively. Therefore, a set of the entire candidate DNA sequences from 5'-ATG to 3'-polyA could be determined. Using the variety of expression vectors carrying those DNA sequences, such as AdEasy-1 vector, pESP-1 vector and pDual vector, (Stratagene, Catalog 2001/2002) the corresponding expressed antigenic proteins could be obtained. Those antigenic proteins could be used as the capture antigens and coated and immobilized on a new set of ELISA plates. The specific antigen(s) would be determined following another round of ELISA test.

1. ELISA Primary Screening for the Peptide Sequence(s) of Epitope(s)

In one preferred embodiment, the penta-peptide library of EcoR I recognition sequence with N-terminal orientation which consists of 8,000 distinctive penta-peptides were chosen as the capture epitopes. In one preferred embodiment, the hexa-peptide library of EcoR I recognition sequence with N-terminal orientation which consists of 160, 000 distinctive hexa-peptides were chosen as the capture epitopes. Each distinctive hexa-peptide was dissolved in 1× Phosphate Buffered Saline (PBS) pH 7.4. The concentration of hexa-peptides could be in the range of 20 ug/ml to 200 ug/ml. A pilot experiment has been done to determine the concentration of the capture epitopes of interest. 40 ul of each solution was added on a corresponding well of the plastic plates such as, Falcon® 3915 Pro-Bind™ microtitre plate or NUNC Maxisorp 96-well ELISA plate or 384-wells plate. The incubation time is from 60 to 120 minutes at 37° C. or 4 hours at room temperature. The plates were covered by Parafilm to prevent evaporation and possible contamination. The plates were incubated at 4° C. for another 12 hours. Before use, each epitope solution in the well was absorbed by a vacuum pump. The wells were washed three times with 1× PBS 0.05% Tween–20. The plates were drained away by inverting the plate 180° on a 3 MM paper pad after each washing for 10 to 30 second. The plate was not allowed to dry completely. 50 μl of blocking solution (1% BSA/1× PBS/0.005% thimerasol) was added in each well to block non-specific binding on the sensitized plates. The blocking step was incubated at 37° C. for 120 minutes followed by subsequent incubation at 4° C. for 12 hours. The plates were covered by Parafilm. The blocking solution in the well was absorbed by a vacuum pump. The wells were washed three times by 1×PBS 0.05% Tween–20. The plates were drained away by inverting the plates 180° on 3 MM paper pad for 10 to 30 seconds. After each washing, the plates were not allowed to dry completely. The patient serum was serially diluted with 1× PBS in accordance with the algorithm of n.sup2 from 1:2 to 1:16,384. Using a known positive antigen to work out the optimal dilution in accordance with standard ELISA protocols as described by Perlmann et al., Enzyme-linked Immuosorbent Assay, Academic Press, Inc., 1994; and Harlow et al., Antibodies: A Laboratory Mannual, Cold Spring Harbor Laboratory Press, 1988; all of which are incorporated herein by reference in their entirety for all purposes. The ideal diluted serum of 40 ul was added in each well of a Falcon® 3915 Pro-Bind™ microtitre plate and 100 ul in each well of a NUNC Maxisorp 96-well ELISA plate. Each plate had wells that contained 1×PBS as negative controls and a known antigen to that serum as the positive control. Wrapped with Parafilm, the plates were incubated at 37° C. for 120 minutes followed by incubation at 4° C. for 12 hours. The incubation solutions from the plates were discarded the wells were washed using 1× PBS 0.05% Tween–20 three times. The conjugate secondary antibody solution of 40 ul was added to each well of the Falcon®) 3915 Pro-Bind™ microtitre plate and 100 ul to each well of the NUNC Maxisorp plate. If the anti-sera were raised in rabbits, goat anti-rabbit alkaline phosphatase antibody was the corresponding conjugate secondary antibody. The incubation time was usually 60 to 90 minutes at 37° C. The conjugate antibody solution was discarded from all the wells and the plate was washed three times with 1×PBS 0.05% Tween–20 at room temperature. 40 ul or 100 ul of substrate solution was added to each well of the Falcon® 3915 Pro-Bind™ microtitre plates and the NUNC Maxisorp plates respectively. If the conjugate enzyme were alkaline phosphatase, p-nitrophenyl phosphate disodium would be chosen as the substrate. It was dissolved in the substrate buffer. (20 mg $NaN_3$, 291 mg $NaHCO_3$, 159 mg $Na_2CO_3$, 10 mg $MgCl_2$ in 100 ml $dH_2O$) Usually, the incubation was at room temperature for 10 to 30 minutes. Sometimes, incubation at 37° C. was required. 10 ul to 50 ul of the stop solution (0.1M EDTA pH 7.4) was added to each well at the end of the incubation to stop the enzyme reaction. The absorbance values were read on a spectrophotometer (microplate reader) at OD 405/450/490. The positive wells were determined. In this manner, the corresponding sequence(s) of the antigenic epitope(s) were determined. In another embodiment, biotinylated serum was diluted to the appropriate titer and was added to each well of the ELISA plates which were precoated with the distinct capture epitope. After the plate was washed three times and the unbound antibodies were removed, Streptavidin-peroxidase was then added to each well as described in the art. The plates were washed three times again to remove all the unbound Streptavidin-peroxidase from each well. The substrate solution containing peroxide and TMB was added to each well. The Streptavidin-peroxidase of antigen-antibody complex catalyzed the enzyme reaction with the substrate to produce colour which was proportional to the amount of antigen in the test sample and could be measured under an ELISA reader.

2. PCR Screening for the Corresponding cDNA Sequence(s) of Epitope(s)

In one embodiment, if EFCMHW (SEQ ID No. 6) was determined as the antigenic epotope by ELISA, the set of 16 candidate corresponding 6 codon (18 mers) oligonucleotides were deduced as follows:

(1) 5'-GAA TTC TGC ATG CAC TGG (SEQ ID No. 7)
(2) 5'-GAA TTT TGC ATG CAC TGG (SEQ ID No. 8)
(3) 5'-GAA TTC TGT ATG CAC TGG (SEQ ID No. 9)
(4) 5'-GAA TTC TGT ATG CAT TGG (SEQ ID No. 10)
(5) 5'-GAG TTC TGC ATG CAC TGG (SEQ ID No. 11)
(6) 5'-GAG TTT TGC ATG CAC TGG (SEQ ID No. 12)
(7) 5'-GAG TTC TGT ATG CAC TGG (SEQ ID No. 13)
(8) 5'-GAG TTC TGT ATG CAT TGG (SEQ ID No. 14)
(9) 5'-GAA TTC TGC ATG CAT TGG (SEQ ID No. 15)
(10) 5'-GAA TTT TGC ATG CAT TGG (SEQ ID No. 16)
(11) 5'-GAA TTC TGT ATG CAT TGG (SEQ ID No. 17)
(12) 5'-GAA TTC TGT ATG CAC TGG (SEQ ID No. 18)
(13) 5'-GAG TTC TGC ATG CAT TGG (SEQ ID No. 19)
(14) 5'-GAG TTT TGC ATG CAT TGG (SEQ ID No. 20)
(15) 5'-GAG TTC TGT ATG CAT TGG (SEQ ID No. 21)
(16) 5'-GAG TTC TGT ATG CAC TGG (SEQ ID No. 22)

The above 16 distinctive six codons (18 mers) oligonucleotide sequences could be consolidated into the sequence of 5'-GAS TTS TGS ATG CAS TGG (SEQ ID No. 23) (S represents substitutions of the universal base analogues such as, 5-nitoindole, 3-nitopyrrole, inosine and hypoxanthine etc.). The substitutions of the universal base are not appropriate at any 3'-end of any oligonucleotide sequences. In one preferred embodiment, 5-nitoindole was chosen to be the universal base in the consolidated six codon (18 mers) oligonucleotide sequence.

In one preferred embodiment, for the purposes of the detections and amplifications of the specific corresponding sequence(s) of interest, the above 16 distinctive six codons (18 mers) oligonucleotide sequences were chosen as upstream PCR primers. Oligo-$d(T)_{18}$ was chosen as the downstream PCR primer in PCR applification. In one preferred embodiment, using the above consolidated six codon (18 mers) oligonucleotide sequence as the upstream PCR primer and oligo-$d(T)_{18}$ as the downstream PCR primer, detected and amplified the specific corresponding sequence(s) of the 3'-portion (from 5'-GAS TTS TGS ATG CAS TGG (SEQ ID No. 23) to polyA) of interest of the gene(s) by PCR. In one embodiment, using the above consolidated six codon (18 mers) oligonucleotide sequences as the downstream PCR primer and each of the oligonucleotides of 5'-ATG oriented oligonucleotide library of a suitable length, such as three codons (9 mer) or four codons (12 mers) or five codons (15 mers) as the upstream PCR primers to detected and amplified the specific corresponding sequence(s) of 5'-portion (from 5'-ATG to 5'-GAS TTS TGS ATG CAS TGG (SEQ ID No. 23)) of the gene(s) of interest by PCR. In one preferred embodiment, the incorporated indirect detectable label was biotinylated-dNTP. The biotinylated sequence could be detected and visualized by Streptavidin which conjugates to a fluorescein isothiocyanate or an enzymatically activatable molecule. In another preferred embodiment, the incorporated indirect detectable label was digoxigenin-dNTP. The sequence incorporated with digoxigenin -dNTP could be detected and visualized by an anti-digoxigenin antibody which conjugated to a fluorescent molecule or an enzymatically activatable molecule (PCR ELISA, Roche Diagnostics GmbH, Cat. No. 1636 120, 2001). In another embodiment, the isolated RNA was reverse transcribed into cDNA which in turn served as the targeting template in PCR. In one embodiment, the initial denaturation was at 94° C. for 1 minute for one cycle. Since the multiple oligonucleotide primers have variable melting temperatures, the optimal annealing temperature varied from 37° C. to 65° C. The elongation was at 72° C. for 2 minutes. The number of cycles was from 25 to 30. The last elongation was at 72° C. for 5 minutes followed by immediately keeping the temperature at 4° C. In one embodiment, in order to work out the optimal annealing temperature of each specific PCR, touchdown PCR protocols were employed (Don et al., Nucleic Acids Res. 19: 4008, 1991). In one embodiment, the PCR solution was prepared to have the final concentration of 100 uM of dATP, dGTP, dTTP and dCTP respectively. The PCR solution contains the final concentration of 1.5 mM $MgCl_2$, 25mM KCI, 50-100 nM of each primer, 1-10 nM of template DNA, 2-10 units of Taq DNA polymerase and 20 mM Tris-HCI. All the positive clones from 3'-portions or 5'-portions of the gene(s) of interest were identified respectively by using the PCR ELISA (DIG-Labeling) Kit (PCR ELISA, Roche Diagnostics GmbH, Cat. No. 1636 120, 2001). The DNA sequence(s) of a set of candidates of full length clones (from 5'-ATG to polyA) of the gene(s) of interest were deduced by all the possible combinations of the positive 5'-portions and 3'-portions of the detected sequences. (PCR ELISA, Roche Diagnostics GmbH, Cat. No. 1636 120, 2001). The DNA sequence(s) of a set of candidates of full length clones (from 5'-ATG to polyA) of the gene(s) of interest were deduced by all the possible combinations of the positive 5'-portions and 3'-portions of the detected sequences.

3. ELISA Final Screening to Determine the Peptide Sequence(s) of Epitope(s)

Using a variety of expression vectors carrying those DNA sequences, such as AdEasy-1 vector, pESP-1 vector and pDual vector, (Stratagene, Catalog 2001/2002) the corresponding expression antigenic proteins could be obtained. Those antigenic proteins could be used as the capture antigens which would be coated and immobilized on a new set of ELISA plates. The peptide sequence(s) of specific antigen(s) could be determined by the final ELISA test.

IX. Proteomics with Peptide Arrays

Protein arrays including peptide and polypeptide arrays are solid-phase ligand binding platforms with immobilized and precisely positioned peptide or polypeptide or protein on a solid surface like silicon, glass slide, polymers, plastics, plastic plates, membrane, microtiter wells, mass spectrometer plates, microbeads, nanoparticles and other particles. Protein arrays are capable of revealing functionalities as well as the interactions of protein to ligand, protein to protein, antigen to antibody and protein to enzyme. The present invention provides series universal standardized peptide libraries of N-terminal orientation, series universal standardized peptide libraries of C-terminal orientation and series universal standardized peptide libraries of restriction endonuclease recognition sequences of two-amino acids orientations based on the inventive algorithms of $20^{(n-1)}$, $20^n$ and $20^{(n-2)}$ respectively for the construction. To identify the responsible antigens and deduce sequences from peptide to DNA, the working principles of the ELISA-PCR-ELISA described in this invention are also applicable herein. The methods of preparing, fabricating and signal detecting of protein arrays were processed as described by Fodor et al., Nature, 364: 555-556,1993: Zhu et al., Nat. Genet. 26: 283-289, 2000; Lueking et al., Anal. Biochem. 270: 103-111, 1999; all of which are incorporated herein by reference in their entirety for all purposes.

X. Standardized Signature Sequence

For example, those inventive libraries of short oligonucleotides such as 9 mers, 12 mers, 15 mers, and 18 mers of 5'-ATG orientated ORF libraries provide sufficient resources for selecting and determining the signature sequences for each expressed gene of genome such as humans. Once the signature sequence for each expressed gene of the entire genome of a given biological species such as humans were identified, determined and registered, the complete sequence analysis may not be required. Once the signature sequences of genetic related diseases were identified, determined and registered, the clinical genetic diagnosis tests could be more accurate and rapid. Those signature sequences could also be used as the genetic markers and drug targeting markers in prognosis tests, drug design and development. They can be used in forensic studies as well. Codon consists of triplet nucleotides namely A, T, G, C, and U. Each of A, T, G, C and U possesses a characteristic maximum energy absorption spectrum at 259 nm, 267 nm, 252 nm, 271 nm and 258 nm respectively. Therefore, each signature sequence possesses a detectable unique energy emission pattern. The existing extrinsic label substances, such as light emitting compounds, quenching compounds and radioactive compounds could be coupled with the signature sequence by means known in the art. The couplings of extrinsic labels to the signature sequence(s) of both nucleic acids and peptide could enable a more sophisticated signature signal for distinction and characterization. Those signature signal(s) could be the chemical or physical signals in different forms such as energy emitting, absorbing, transferring and quenching. The signature sequence and the corresponding signature signal could be detectable and measurable either chemically, or magnetically, or electromagnetically, or electronically or optically or combinatorial (Chan, U.S. Pat. No. 6,210,896, 2001).

XI. Standardized Universal Sequencing Databases

In accordance with the present inventive series universal standardized oligonucleotide and peptide libraries of any given length, the corresponding standardized universal sequence databases are set forth below.

1. 5'-Terminal Sequence Tag Series Databases

In one embodiment, all the possible ORF codon-based sense sequences of 9 mers long having 5'-terminal start codon orientation consist of 9-mer 5'-terminal sequence tag database. In other embodiments, the length of each distinctive sequence is 12 mers. In other embodiments, the length of each distinctive sequence is 15 mers. In other embodiments, the length of each distinctive sequence is 18 mers. In other embodiments, the length of each distinctive sequence is 21 mers. In other embodiments, the length of each distinctive sequence is 24 mers.

In another one embodiment, all the possible 5'-UTR sense codon-based sequences of 9 mers long having 3'-terminal start codon orientation consist of 9-mer 5'-UTR terminal sequence tag database. In other embodiment, the length of each distinctive sequence is 12 mers. In other embodiments, the length of each distinctive sequence is 15 mers. In other embodiments, the length of each distinctive sequence is 18 mers. In other embodiments, the length of each distinctive sequence is 21 mers. In other embodiments, the length of each distinctive sequence is 24 mers.

2. 3'-Terminal Sequence Tag Series Databases

In one embodiment, all the possible ORF codon-based sense sequences of 9 mers long having 3'-terminal stop codon orientation consist of 9-mer 3'-terminal sequence tag electronic version of the database. In other embodiments, the length of each distinctive sequence is 12 mers. In other embodiments, the length of each distinctive sequence is 15 mers. In other embodiments, the length of each distinctive sequence is 18 mers. In other embodiments, the length of each distinctive sequence is 21 mers. In other embodiments, the length of each distinctive sequence is 24 mers.

In another one embodiment, all the possible 3'-UTR sense codon-based sequences of 9 mers long having 5'-terminal stop codon orientation consist of 9-mer 3'-UTR terminal sequence tag electronic version of the database. In other embodiments, the length of each distinctive sequence is 12 mers. In other embodiments, the length of each distinctive sequence is 15 mers. In other embodiments, the length of each distinctive sequence is 18 mers. In other embodiments, the length of each distinctive sequence is 21 mers. In other embodiments, the length of each distinctive sequence is 24 mers.

3. QAGE Databases

The Sense Sequence of Restriction Endonuclease Recognition Sequence of Two-codon Orientations Series Databases is derived from the corresponding QAGE Oligonulceotide Libraries. In one embodiment, BamH I oriented 12-mer codon-based non-coding region oligonulceotide library which consists of 4,096 distinctive 12-mer oligonulceotides were entirely turned into BamH I QAGE 12-mer electronic version of the database. Each oligonulceotide sequence has at least one annotation and all that information could be retrieved and displayed on a computer screen to one skilled in the art. QAGE Databases is the important and necessary tool and resources for DNA Arrays based QAGE technology platforms.

4. Other Databases

Other electronic versions of the databases derived from the inventive codon-based oligonucleotide libraries are 5'-terminal Anti-sense Sequence Series Databases. 3'-terminal Anti-sense Sequence Series Databases, The Anti-sense Sequence of Restriction Endonuclease Recognition Sequence of Two-codons Orientations Series Databases, N-terminal Amino Acid Sequence Series Databases, C-terminal Amino Acid Sequence Series Databases, The Amino Acid Sequence of Restriction Endonuclease Recognition Sequence of Two Amino Acids Orientations Series Databases.

In one embodiment, the above series terminal sequence databases, QAGE databases and their analogues with any given length could be written, rewritten, modified, formatted and recorded in current available computer software, such as Microsoft Word, Microsoft Excel and Microsoft Access etc. to form computer readable image media. In another embodiment, those databases were represented in other computer readable formats, such as ASCII file and other data processor formats, such as Sybase, DB2 and Oracle etc. In order to ensure any computer including ones not connected to the Internet has access to those databases, in one embodiment, those electronic versions of the databases were designed to be capable to store in various forms and resources and maintain the sequence images computer readable. In yet another embodiment, those databases could be stored either magnetically or electrically or optically or combinations thereof. In an alternative embodiment, except for those databases stored in a central computer, the storage media was 3½ floppy discs, tapes, computer hard drives, RAM and CD-ROM etc. The utilities of those databases are various. If a sequence of either nucleic acid or amino acid were determined whether known or unknown, a query could be made to those databases from a computer with Graphical User Interfaces (GUIs) such as, the Macintosh and Microsoft Windows such as Window 95, 98, 2000 and Window XP. In another embodiment, those electronic versions of the databases were developed into electronic versions of the encyclopaedia. Each of the said sequences in the database has at the least two annotations wherein the said annotations are computer readable. The said annotations for each said sequence on various topics and subjects are arranged in alphabetical order. Each of the said sequence could be used as a "query sequence" in the search against the said encyclopaedia. Each of the said sequence could be represented or displayed in a word processing file wherein the said file is Microsoft Word or ASCII file stored in a database application or other suitable database known in the art.

In another embodiment, the search and identify the specific 5'-terminal, 3'-terminal, RERS-terminal, N-terminal and C-terminal sequences of any given length by the comparison and sequence matching were performed by on-line search engine. Search results were listed as a summary of links to the details about a specific sequence record.

It is known in the art that a specific pair of 5'-terminal and 3'-terminal sequence that usually possesses 3 codons (9 mers) or beyond it in the length of a particular gene could be used as upstream and downstream primers in PCR. With a specific optimized PCR protocol for a particular gene sequence, the full length of that particular ORF sequence from or before the start codon to the stop codon could be identified and cloned experimentally. The full length of that particular ORF sequence from or before the stop codon to the start codon could also be identified and cloned experimentally. Those databases could also be used to identify and determine the signature sequence of a gene of interest. Those electronic versions of the databases could be used as routine tools for HTS, PCR and cloning operations by the research and clinical laboratories.

XII. Quality Control

HTS is massive parallel technology platform for gene profiling. It is necessary to establish relevant monitor and quality control systems to coordinate the operation. The present invention aims at addressing the above issues by inventing a series of working kits.

1. RNA Quality Control Kit

The present invention provides a working kit for RNA quality control. It is known that mRNA degradation is often due to the residual RNases in the RNA extraction. In one preferred embodiment, 2-5 ug of test RNA sample was dissolved in DEPC-treated $H_2O$. The same amount of the control RNA sample was dissolved in 0.1% SDS solution. Both are incubated at 37° C. for 30 minutes at the same time. 2-5 ug of test RNA samples and the equal amount of the control were loaded evenly and paralleled on two adjacent paralleled lanes of 1% Agarose gel containing Ethidium Bromide. Electrophoresis was performed as a matter of routine for one skilled in the art. The photos were taken under UV light. In comparison with the ratio and intensity of the bands of 28s and 18s of rRNA in the gel, the information regarding whether the residual RNases exist could be deduced. The present invention provides a working kit of RNA Quality Control System containing 0.1% SDS solution and protocols for the immediate usage.

2. cDNA Quality Control Kits mRNA reverse transcription is one of the crucial steps with a deep impact on the subsequent procedures such as cDNA syntheses, hybridization, PCR and cloning. The present invention has chosen house-keeping genes as indicators for cDNA quality control monitoring. In one embodiment, mouse beta-actin gene (GenBank Accession: X03672) were chosen as an indicator for the cDNA Quality Control by means of PCR detection. The targeting regions and PCR primers are as following:

```
5'-end region of 231 b.p./PCR product size: 231 b.p
Forward primer (F1):
5'-ATGGTGGGAATGGGTCAGAAGGAC-3'      (SEQ ID No. 24)
Backward primer (B1):
5'-GGTCATCTTTTCACGGTTGGC-3'         (SEQ ID No. 25)

3'-end region of 453 b.p./PCR product size:
453 b.p.
Forward primer (F2):
5'-TGAGAGGGAAATCGTGCGTG-3'          (SEQ ID No. 26)
Backward primer (B2):
5'-ATCTGCTGGAAGGTGGACAGTGAG-3'      (SEQ ID No. 27)

The sequence of 935 b.p./PCR product size: 935 b.p.
Forward primer (F1):
5'-ATGGTGGGAATGGGTCAGAAGGAC-3'      (SEQ ID No. 24)
Backward primer (B2):
5'-ATCTGCTGGAAGGTGGACAGTGAG-3'      (SEQ ID No. 27)
```

PCR Profile: Initial Denaturation: 94° C., 45 Sec. Denaturation: 94° C. for 30 Sec. Annealing: 50° for 30 Sec. Extension: 72° C. for 90 Sec. for 30 Cycles. In other embodiment, PCR Profile: Initial Denaturation: 94° C., 45 Sec. Denaturation: 94° C. for 30 Sec. Annealing: 54° for 30 Sec. Extension: 72° C. for 90 Sec. for 25 Cycles. In one other embodiment, PCR Profile: Initial Denaturation: 94° C., 45 Sec. Denaturation: 94° C. for 30 Sec. Annealing: 58° for 30 Sec. Extension: 72° C. for 90 Sec. for 25 Cycles.

In one preferred embodiment, PCR Protocol: the final volume of each PCR reaction is 20 ul. It contains 1 to 25 ng of cDNA, 1.5 mM $MgCl_2$, 50 mM KCl, 20 mM Tris-HCl (pH 7.4), 0.1 mM EDTA, 0.1 mM DTT, 150 uM each of dNTPs (dATP, dCTP, dGTP and dTTP), 0.05% Tween 20, 10 to 25 pM of each primer and 1 to 2 units of Taq DNA polymerase in a PCR reaction tube.

In another embodiment, the sequences Homo sapiens glyceraldehyde-3-phosphate dehydrogenase (GAPD) was chosen as the indicators for the cDNA quality control purpose. GAPD sequence could be accessed at GenBank Accession: NM_002046.2. The targeting regions and PCR primers are as following:

```
5'-end region of 227 b.p./PCR product size:
227 b.p.
Forward primer (F1):
5'-AAGGTGAAGGTCGGAGTCAACG-3'        (SEQ ID No. 28)
Backward primer (B1):
5'-TGGAAGATGGTGATGGGATTTC-3'        (SEQ ID No. 29)

3'-end region of 477 b.p./PCR product size:
447 b.p.
Forward primer (F2):
5'-TGCCATCACTGCCACCCAGAAGAC-3'      (SEQ ID No. 30)
Backward primer (B2):
5'-ATGAGGTCCACCACCCTGTTGCTG-3'      (SEQ ID No. 31)

The sequence of 977 b.p./PCR product size: 977 b.p.
Forward primer (F1):
5'-AAGGTGAAGGTCGGAGTCAACG-3'        (SEQ ID No. 28)
Backward primer (B2):
5'-ATGAGGTCCACCACCCTGTTGCTG-3'      (SEQ ID No. 31)
```

PCR Profile: Initial Denaturation: 94° C., 45 Sec. Denaturation: 94° C. for 30 Sec. Annealing: 50° for 30 Sec. Extension: 72° C. for 90 Sec. for 30 Cycles. In other embodiment, PCR Profile: Initial Denaturation: 94° C., 45 Sec. Denaturation: 94° C. for 30 Sec. Annealing: 54° for 30 Sec. Extension: 72° C. for 90 Sec. for 25 Cycles. In one other embodiment, PCR Profile: Initial Denaturation: 94° C., 45 Sec. Denaturation: 94° C. for 30 Sec. Annealing: 58° for 30 Sec. Extension: 72° C. for 90 Sec. for 25 Cycles.

In one preferred embodiment, PCR Protocol: the final volume of each PCR reaction is 20 ul. It contains 1 to 25 ng of cDNA, 1.5 mM $MgCl_2$, 50 mM KCl, 20 mM Tris-HCl (pH 7.4), 0.1 mM EDTA, 0.1 mM DTT, 150 uM each of dNTPs (dATP, dCTP, dGTP and dTTP), 0.05% Tween 20, 10 to 25 pM of each primer and 1 to 2 units of Taq DNA polymerase in a PCR reaction tube.

cDNA pool or library was diluted in the range from 1:1000 to 1:10,000 to 100,000. The diluted cDNA library or pool was used as the template in all the PCR protocols for all the said cDNA quality control system.

The resulting PCR amplicons were loaded evenly and paralleled on three adjacent paralleled lanes of 1% Agarose gel containing Ethidium Bromide. Electrophoresis was performed as a matter of routine for one skilled in the art. Under the UV light, the evaluation of the integrity of the generated 5' end, 3' end and the entire cDNA fragments were performed by the comparison of the intensity of the three target bands. If the intensity of 5'-end fragment was equal to 3'-end fragment, it might imply that the targeting molecule (indicator) was intact. If the intensity of 5'-end fragment was higher than 3'-end fragment, it might imply that degradation happened on the 3'-end of the sequence. If the intensity of 5'-end fragment was lower than 3'-end fragment, it might imply that degradation happened on the 5'-end of the sequence. The present invention provides a working kit of cDNA Quality Control System containing the said PCR primers, relevant reagents and protocols for the immediate usage.

In an alternative embodiment, each of the said PCR primers was organized into the corresponding sets of oligonucleotide according to the above descriptions. Each of the said sets was being immobilized at a specific site on or to a suitable solid support such as DNA Arrays or DNA Microarrays to form the control part on the said DNA Arrays or DNA Microarrays. In another alternative embodiment, each of the said cDNA fragments specifically amplified by the said corresponding PCR primers was being immobilized at a specific site on or to a suitable solid support such as cDNA Arrays or DNA Microarrays to form the control part on the said cDNA Arrays or DNA Microarrays in according to the above descriptions. The present invention also provides a working kit of cDNA Quality Control System containing the said cDNA fragments specifically amplified by the said PCR primers, relevant reagents and protocols for the immediate usage.

XIII. EXAMPLES

The following examples are intended to provide detailed illustrations of the present invention but are by no means limited to the invention thereof.

Example 1

PCR Protocol 1 to 25 ng cDNA, 1.5 mM $MgCl_2$, 50 mM KCl, 20 mM Tris-HCl (pH 7.4), 0.1 mM EDTA, 0.1 mM DTT, 150 uM dNTPs (dATP, dCTP, dGTP and dTTP), 0.05% Tween 20, 10 to 25 pM primer and 1 to 2 units of Taq DNA polymerase in 20 ul. Thermostable DNA Polymerase was selected from a group of polymerases which includes, without limiting the generality of the foregoing, Taq DNA polymerase, AmpliTaq Gold DNA polymerase, Pfu DNA polymerase, Tfl DNA polymerase, Tli DNA polymerase, Tth DNA polymerase, $Vent_R$ (exo⁻) DNA polymerase and Deep $Vent_R$ (exo⁻) DNA polymerase. The analogues and modified dNTPs may be used in conjunction with the present invention which include, without limiting the generality of the foregoing, 5'-nitroindole, 3'-nitropyrrole, inosine, hypoxanthine, LNA, biotin–11-dUTP, biotin–16-dUTP, 5'-bromo-dUTP, dUTP, dig-11-dUTP and 7-deaza dGTP.

Example 2

PCR Temperature Profiles

The threshold cycle consists of denaturing temperature of 45 second at 94° C., annealing temperature of 90 second at 40° C. and extension temperature of 60 second at 72° C. The number of cycles for PCR amplification was 30, each of which consists of a denaturing step of 30 seconds at 94° C., an annealing step of 90 seconds at 40° C. and an extension step of 60 seconds at 72° C. The end cycle consists of 5 minutes at 72° C. following by 4° C. Each specified upstream primer is a distinct 9 mers 5'-ATG oriented oligonucleotide represented by the formula $5'-I_S(C_S)_{n1}-3'$. The common downstream primer is oligo-d(T)$_{18}$.

(1) Denaturation:

94° C. for 30sec. It is applicable to all the said primers.

(2) Annealing:

40° C. or 40° C. plus 1-5° C. or 40° C. minus 1-5° C. for 60sec.:

It is applicable to the said 49 upstream primers having 11.1% GC content after the incorporation of seven LNA in each 9 mers oligonucleotide sequence, such as 5'-ATGATAATA. It is applicable to the said 308 upstream primers having 22.2% GC content after the incorporation of six LNA in each 9 mers oligonucleotide sequence, such as 5'-ATGGAAATA. It is applicable to the said 820 upstream primers having 33.3% GC content after the incorporation of four LNA in each 9 mers oligonucleotide sequence, such as 5'-ATGGCAATA. It is applicable to the said 1,168 upstream primers having 44.4% GC content after the incorporation of two LNA in each 9 mers oligonucleotide sequence, such as 5'-ATGGCAGAA. It is applicable to the said 928 upstream primers having 55.6% GC content after the incorporation of one LNA in each 9 mers oligonucleotide sequence, such as 5'-ATGGCAGCA. It is applicable to the said 384 upstream primers having 66.7% GC content after without the incorporation of LNA in each 9 mers oligonucleotide sequence, such as 5'-ATGGCAGCC. It is applicable to the said 64 upstream primers having 77.8% GC content after the incorporation of one LNA at 5'-end of each 9 mers oligonucleotide sequence, such as 5'-ATGGCCGCC.

(3) Extension: 72° C. for 60sec.

(4) Cycle Number: 30

(5) Final Extension: 72° C. for 5 minus for all.

If no bands on an Agarose gel are observed, the annealing temperature might be adjusted in the range of 1° C. to 5° C. below the original annealing temperature and, if unwanted bands and/or several bands appeared, the annealing temperature might be adjusted in the range of 1° C. to 5° C. above the original annealing temperature in each subsequent optimization step. It is recommended that if the inventive 9 mers, 12 mers, 15 mers, 18 mers, 21 mers, and 24 mers oligonucleotides are used as the PCR primers, the range of annealing temperatures is often from 37° C. to 56° C. The higher the annealing temperature is increased, the more specific the PCR results may obtain. Therefore, the annealing temperature can be increased as high as the extension temperature in some cases under certain conditions.

Example 3

The Touchdown PCR Protocol

The Touchdown PCR protocol starts with an annealing temperature above the primer's ideal temperature. At each cycle, the annealing temperature is programmed to decrease 1° C. until reaching the targeting annealing temperature. In one preferred embodiment, 9 mers 5'-ATG oriented oligonucleotides represented by the formula $5'-I_S(C_S)_{n1}-3'$ such as 5'-ATGGCCGCC had three consecutive universal bases such as 5'-nitroindoles covalently added at each of their 5'-ends to form 12 mers oligonucleotides. The 12mers oligonucleotides were then used as PCR upstream primer. oligo-d(T)$_{18}$ was used as PCR downstream primer. In one preferred embodiment, the threshold cycle consists of a denaturing step of 45 seconds at 94° C. The second cycle consists of denaturing step of 30 seconds at 94° C., an annealing step of 90 seconds at 50° C. and an extension step of 60 seconds at 72° C. The third cycle consists of a denaturing step of 30 seconds at 94° C., an annealing step of 90 seconds at 49° C. and an extension step of 60 seconds at 72° C. The fourth cycle consists of a denaturing step of 30 seconds at 94° C., an annealing step of 90 seconds at 48° C. and an extension step of 60 seconds at 72° C. The fifth cycle consists of a denaturing step of 30 seconds at 94° C., an annealing step of 90 seconds at 47° C. and an extension step of 60 seconds at 72° C. The sixth cycle consists of a denaturing step of 30 seconds at 94° C., an annealing step of 90 seconds at 46° C. and an extension step of 60 seconds at 72° C. The seventh cycle consists of a denaturing step of 30 seconds at 94° C., an annealing step of 90 seconds at 45° C. and an extension step of 60 seconds at 72° C. The eighth cycle consists of a denaturing step of 30 seconds at 94° C., an annealing step of 90 seconds at 44° C. and an extension step of 60 seconds at 72° C. The ninth cycle consists of a denaturing step of 30 seconds at 94° C., an annealing step of 90 seconds at 43° C. and an extension step of 60 seconds at 72° C. The tenth cycle consists of a denaturing step of 30 seconds at 94° C., an annealing step of 90 seconds at 42° C. and an extension step of 60 seconds at 72° C. The number of cycles for subsequent PCR amplification was 30, with each cycle consisting of a denaturing step of 30 seconds at 94° C., an annealing step of 90 seconds at 42° C. and an extension step of 60 seconds at 72° C. The final cycle consists of 5 minutes at 72° C. following by 4° C.

While the preferred embodiments of the invention have been described above, it will be recognized and understood that various modifications may be made therein, and the appended claims are intended to cover all such modifications which may fall within the spirit and scope of the invention.

XIV. Equivalents

While the preferred embodiments of the invention have been described above, it will be recognized and understood that various modifications may be made therein, and the appended claims are intended to cover all such modifications which may fall within the spirit and scope of the invention. Taken together, the inventive methods, without limiting the generality of the foregoing, comprising a series of complex and combinatorial methods, working platforms and systems are comprehensive. Obviously, a unique, novel and useful method of gene signature, identification, profiling, cloning and determination has been described through the foregoing detailed illustrations and descriptions of various aspects, different examples and specific embodiments of the present invention. Although the specific embodiments and examples have been introduced and disclosed herein, it has been accomplished by way of example for the objectives of explanation and illustration only, without limiting the generality of the foregoing, regarding the spirit and scope of the claims made for the invention. Specifically, it is contemplated by the inventors that various substitutions, alterations, modification, revisions and developments may be made in part or as the whole regarding both the structures or and the functions of the invention without departing from the spirit and the scope of the invention as defined by the claims. For example, the choices of nucleotides and amino acids from natural, synthetic or chemically modified resources respectively, the form of nucleic acids strands, such as sense or anti-sense, the forms of cDNA, oligonulceotide, deoxyoligonulceotide, peptide, their corresponding analogues and derivatives, the forms of being immobilized at a specific discrete position on or to a suitable solid support whether covalently or non-covalently, the forms of being immobilized at a specific discrete position on or to a suitable solid support whether directly or indirectly, the forms of being immobilized at a specific discrete position on or to a suitable solid support whether through or not through a linker, the size and shape of the said specific discrete position, the size and shape of the said suitable solid support, the forms of said linker, the forms of Oligonulceotide Arrays, cDNA Arrays, cDNA Microarrays and peptide arrays respectively, the particular labelling substances and the corresponding signal detection measurements, or the particular single or the combinatorial oligonucleotide or deoxyoligonulceotide or peptide libraries are conceived as a matter of routine for one skilled in the art with knowledge of the embodiments described herein.

TABLE 1

61 Codons

| No. | Codons in DNA | Codons in mRNA | GC Content |
|---|---|---|---|
| 1 | 5'-GCA | 5'-GCA | 66.67% |
| 2 | 5'-TGC | 5'-UGC | 66.67% |
| 3 | 5'-GAC | 5'-GAC | 66.67% |
| 4 | 5'-GAA | 5'-GAA | 33.33% |
| 5 | 5'-TTC | 5'-UUC | 33.33% |
| 6 | 5'-GGA | 5'-GGA | 66.67% |
| 7 | 5'-CAC | 5'-CAC | 66.67% |
| 8 | 5'-ATA | 5'-AUA | 0% |
| 9 | 5'-AAA | 5'-AAA | 0% |
| 10 | 5'-TTA | 5'-UUA | 0% |
| 11 | 5'-ATG | 5'-AUG | 33.33% |
| 12 | 5'-AAC | 5'-AAC | 33.33% |
| 13 | 5'-CCA | 5'-CCA | 66.67% |
| 14 | 5'-CAA | 5'-CAA | 33.33% |
| 15 | 5'-AGA | 5'-AGA | 33.33% |
| 16 | 5'-AGC | 5'-AGC | 66.67% |
| 17 | 5'-ACA | 5'-ACA | 33.33% |
| 18 | 5'-GTA | 5'-GUA | 33.33% |
| 19 | 5'-TGG | 5'-UGG | 66.67% |
| 20 | 5'-TAC | 5'-UAC | 33.33% |
| 21 | 5'-GCC | 5'-GCC | 100% |
| 22 | 5'-TGT | 5'-UGU | 33.33% |
| 23 | 5'-GAT | 5'-GAU | 33.33% |
| 24 | 5'-GAG | 5'-GAG | 66.67% |
| 25 | 5'-TTT | 5'-UUU | 0% |
| 26 | 5'-GGC | 5'-GGC | 100% |
| 27 | 5'-CAT | 5'-CAU | 33.33% |
| 28 | 5'-ATC | 5'-AUC | 33.33% |
| 29 | 5'-AAG | 5'-AAG | 33.33% |
| 30 | 5'-TTG | 5'-UUG | 33.33% |
| 31 | 5'-AAT | 5'-AAU | 0% |
| 32 | 5'-CCC | 5'-CCC | 100% |
| 33 | 5'-CAG | 5'-CAG | 66.67% |

TABLE 1-continued

61 Codons

| No. | Codons in DNA | Codons in mRNA | GC Content |
|---|---|---|---|
| 34 | 5'-AGG | 5'-AGG | 66.67% |
| 35 | 5'-AGT | 5'-AGU | 33.33% |
| 36 | 5'-ACC | 5'-ACC | 66.67% |
| 37 | 5'-GTC | 5'-GUC | 66.67% |
| 38 | 5'-TAT | 5'-UAU | 0% |
| 39 | 5'-GCG | 5'-GCG | 100% |
| 40 | 5'-GGG | 5'-GGG | 100% |
| 41 | 5'-ATT | 5'-AUU | 0% |
| 42 | 5'-CTA | 5'-CUA | 33.33% |
| 43 | 5'-CCG | 5'-CCG | 100% |
| 44 | 5'-CGA | 5'-CGA | 66.67% |
| 45 | 5'-TCA | 5'-UCA | 33.33% |
| 46 | 5'-ACG | 5'-ACG | 66.67% |
| 47 | 5'-GTG | 5'-GUG | 66.67% |
| 48 | 5'-GCT | 5'-GCU | 66.67% |
| 49 | 5'-GGT | 5'-GGU | 66.67% |
| 50 | 5'-CTC | 5'-CUC | 66.67% |
| 51 | 5'-CCT | 5'-CCU | 66.67% |
| 52 | 5'-CGC | 5'-CGC | 100% |
| 53 | 5'-TCC | 5'-UCC | 66.67% |
| 54 | 5'-ACT | 5'-ACU | 33.33% |
| 55 | 5'-GTT | 5'-GUU | 33.33% |
| 56 | 5'-CTG | 5'-CUG | 66.67% |
| 57 | 5'-CGG | 5'-CGG | 100% |
| 58 | 5'-TCG | 5'-UCG | 66.67% |
| 59 | 5'-CTT | 5'-CUU | 33.33% |
| 60 | 5'-CGT | 5'-CGU | 66.67% |
| 61 | 5'-TCT | 5'-UCU | 33.33% |

GC Content of 61 Codons: 100%: 8 66.7%: 24 33.3%: 22 0%: 7

TABLE 2

61 Antisense Codons

| No. | Antisense Codons DNA | Antisense Codons in mRNA | GC Content |
|---|---|---|---|
| 1 | 5'-TGC | 5'-UGC | 66.67% |
| 2 | 5'-GCA | 5'-GCA | 66.67% |
| 3 | 5'-GTC | 5'-GUC | 66.67% |
| 4 | 5'-TTC | 5'-UUC | 33.33% |
| 5 | 5'-GAA | 5'-GAA | 33.33% |
| 6 | 5'-TCC | 5'-UCC | 66.67% |
| 7 | 5'-GTG | 5'-GUG | 66.67% |
| 8 | 5'-TAT | 5'-UAU | 0% |
| 9 | 5'-TTT | 5'-UUU | 0% |
| 10 | 5'-TAA | 5'-UAA | 0% |
| 11 | 5'-CAT | 5'-CAU | 33.33% |
| 12 | 5'-GTT | 5'-GUU | 33.33% |
| 13 | 5'-TGG | 5'-UGG | 66.67% |
| 14 | 5'-TTG | 5'-UUG | 33.33% |
| 15 | 5'-TCT | 5'-UCU | 33.33% |
| 16 | 5'-GCT | 5'-GCU | 66.67% |
| 17 | 5'-TGT | 5'-UGU | 33.33% |
| 18 | 5'-TAC | 5'-UAC | 33.33% |
| 19 | 5'-CCA | 5'-CCA | 66.67% |
| 20 | 5'-GTA | 5'-GUA | 33.33% |
| 21 | 5'-GGC | 5'-GGC | 100% |
| 22 | 5'-ACA | 5'-ACA | 33.33% |
| 23 | 5'-ATC | 5'-AUC | 33.33% |
| 24 | 5'-CTC | 5'-CUC | 66.67% |
| 25 | 5'-AAA | 5'-AAA | 0% |
| 26 | 5'-GCC | 5'-GCC | 100% |
| 27 | 5'-ATG | 5'-AUG | 33.33% |
| 28 | 5'-GAT | 5'-GAU | 33.33% |
| 29 | 5'-CTT | 5'-CUU | 33.33% |
| 30 | 5'-CAA | 5'-CAA | 33.33% |
| 31 | 5'-ATT | 5'-AUU | 0% |
| 32 | 5'-GGG | 5'-GGG | 100% |
| 33 | 5'-CTG | 5'-CUG | 66.67% |
| 34 | 5'-CCT | 5'-CCU | 66.67% |
| 35 | 5'-ACT | 5'-ACU | 33.33% |
| 36 | 5'-GGT | 5'-GGU | 66.67% |

TABLE 2-continued

61 Antisense Codons

| No. | Antisense Codons DNA | Antisense Codons in mRNA | GC Content |
|---|---|---|---|
| 37 | 5'-GAC | 5'-GAC | 66.67% |
| 38 | 5'-ATA | 5'-AUA | 0% |
| 39 | 5'-CGC | 5'-CGC | 100% |
| 40 | 5'-CCC | 5'-CCC | 100% |
| 41 | 5'-AAT | 5'-AAU | 0% |
| 42 | 5'-TAG | 5'-UAG | 33.33% |
| 43 | 5'-CGG | 5'-CGG | 100% |
| 44 | 5'-TCG | 5'-UCG | 66.67% |
| 45 | 5'-TGA | 5'-UGA | 33.33% |
| 46 | 5'-CGT | 5'-CGU | 66.67% |
| 47 | 5'-CAC | 5'-CAC | 66.67% |
| 48 | 5'-AGC | 5'-AGC | 66.67% |
| 49 | 5'-ACC | 5'-ACC | 66.67% |
| 50 | 5'-GAG | 5'-GAG | 66.67% |
| 51 | 5'-AGG | 5'-AGG | 66.67% |
| 52 | 5'-GCG | 5'-GCG | 100% |
| 53 | 5'-GGA | 5'-GGA | 66.67% |
| 54 | 5'-AGT | 5'-AGU | 33.33% |
| 55 | 5'-AAC | 5'-AAC | 33.33% |
| 56 | 5'-CAG | 5'-CAG | 66.67% |
| 57 | 5'-CCG | 5'-CCG | 100% |
| 58 | 5'-CGA | 5'-CGA | 66.67% |
| 59 | 5'-AAG | 5'-AAG | 33.33% |
| 60 | 5'-ACG | 5'-ACG | 66.67% |
| 61 | 5'-AGA | 5'-AGA | 33.33% |

GC Content of 61 Antisense Codons: 100%: 8 66.7%: 24 33.3%: 22 0%: 7

TABLE 3

64 Codons

| No. | Codons in DNA | Codons in mRNA | GC Content |
|---|---|---|---|
| 1 | 5'-GCA | 5'-GCA | 66.67% |
| 2 | 5'-TGC | 5'-UGC | 66.67% |
| 3 | 5'-GAC | 5'-GAC | 66.67% |
| 4 | 5'-GAA | 5'-GAA | 33.33% |
| 5 | 5'-TTC | 5'-UUC | 33.33% |
| 6 | 5'-GGA | 5'-GGA | 66.67% |
| 7 | 5'-CAC | 5'-CAC | 66.67% |
| 8 | 5'-ATA | 5'-AUA | 0% |
| 9 | 5'-AAA | 5'-AAA | 0% |
| 10 | 5'-TTA | 5'-UUA | 0% |
| 11 | 5'-ATG | 5'-AUG | 33.33% |
| 12 | 5'-AAC | 5'-AAC | 33.33% |
| 13 | 5'-CCA | 5'-CCA | 66.67% |
| 14 | 5'-CAA | 5'-CAA | 33.33% |
| 15 | 5'-AGA | 5'-AGA | 33.33% |
| 16 | 5'-AGC | 5'-AGC | 66.67% |
| 17 | 5'-ACA | 5'-ACA | 33.33% |
| 18 | 5'-GTA | 5'-GUA | 33.33% |
| 19 | 5'-TGG | 5'-UGG | 66.67% |
| 20 | 5'-TAC | 5'-UAC | 33.33% |
| 21 | 5'-GCC | 5'-GCC | 100% |
| 22 | 5'-TGT | 5'-UGU | 33.33% |
| 23 | 5'-GAT | 5'-GAU | 33.33% |
| 24 | 5'-GAG | 5'-GAG | 66.67% |
| 25 | 5'-TTT | 5'-UUU | 0% |
| 26 | 5'-GGC | 5'-GGC | 100% |
| 27 | 5'-CAT | 5'-CAU | 33.33% |
| 28 | 5'-ATC | 5'-AUC | 33.33% |
| 29 | 5'-AAG | 5'-AAG | 33.33% |
| 30 | 5'-TTG | 5'-UUG | 33.33% |
| 31 | 5'-AAT | 5'-AAU | 0% |
| 32 | 5'-CCC | 5'-CCC | 100% |
| 33 | 5'-CAG | 5'-CAG | 66.67% |
| 34 | 5'-AGG | 5'-AGG | 66.67% |
| 35 | 5'-AGT | 5'-AGU | 33.33% |
| 36 | 5'-ACC | 5'-ACC | 66.67% |
| 37 | 5'-GTC | 5'-GUC | 66.67% |
| 38 | 5'-TAT | 5'-UAU | 0% |
| 39 | 5'-GCG | 5'-GCG | 100% |

TABLE 3-continued

64 Codons

| No. | Codons in DNA | Codons in mRNA | GC Content |
|---|---|---|---|
| 40 | 5'-GGG | 5'-GGG | 100% |
| 41 | 5'-ATT | 5'-AUU | 0% |
| 42 | 5'-CTA | 5'-CUA | 33.33% |
| 43 | 5'-CCG | 5'-CCG | 100% |
| 44 | 5'-CGA | 5'-CGA | 66.67% |
| 45 | 5'-TCA | 5'-UCA | 33.33% |
| 46 | 5'-ACG | 5'-ACG | 66.67% |
| 47 | 5'-GTG | 5'-GUG | 66.67% |
| 48 | 5'-GCT | 5'-GCU | 66.67% |
| 49 | 5'-GGT | 5'-GGU | 66.67% |
| 50 | 5'-CTC | 5'-CUC | 66.67% |
| 51 | 5'-CCT | 5'-CCU | 66.67% |
| 52 | 5'-CGC | 5'-CGC | 100% |
| 53 | 5'-TCC | 5'-UCC | 66.67% |
| 54 | 5'-ACT | 5'-ACU | 33.33% |
| 55 | 5'-GTT | 5'-GUU | 33.33% |
| 56 | 5'-CTG | 5'-CUG | 66.67% |
| 57 | 5'-CGG | 5'-CGG | 100% |
| 58 | 5'-TCG | 5'-UCG | 66.67% |
| 59 | 5'-CTT | 5'-CUU | 33.33% |
| 60 | 5'-CGT | 5'-CGU | 66.67% |
| 61 | 5'-TCT | 5'-UCU | 33.33% |
| 62 | 5'-TAA | 5'-UAA | 0% |
| 63 | 5'-TGA | 5'-UGA | 33.33% |
| 64 | 5'-TAG | 5'-UAG | 33.33% |

GC Content of 64 Codons: 100%: 8 66.7%: 24 33.3%: 24 0%: 8

TABLE 4

64 Antisense Codons

| No. | Antisense Codons DNA | Antisense Codons in mRNA | GC Content |
|---|---|---|---|
| 1 | 5'-TGC | 5'-UGC | 66.67% |
| 2 | 5'-GCA | 5'-GCA | 66.67% |
| 3 | 5'-GTC | 5'-GUC | 66.67% |
| 4 | 5'-TTC | 5'-UUC | 33.33% |
| 5 | 5'-GAA | 5'-GAA | 33.33% |
| 6 | 5'-TCC | 5'-UCC | 66.67% |
| 7 | 5'-GTG | 5'-GUG | 66.67% |
| 8 | 5'-TAT | 5'-UAU | 0% |
| 9 | 5'-TTT | 5'-UUU | 0% |
| 10 | 5'-TAA | 5'-UAA | 0% |
| 11 | 5'-CAT | 5'-CAU | 33.33% |
| 12 | 5'-GTT | 5'-GUU | 33.33% |
| 13 | 5'-TGG | 5'-UGG | 66.67% |
| 14 | 5'-TTG | 5'-UUG | 33.33% |
| 15 | 5'-TCT | 5'-UCU | 33.33% |
| 16 | 5'-GCT | 5'-GCU | 66.67% |
| 17 | 5'-TGT | 5'-UGU | 33.33% |
| 18 | 5'-TAC | 5'-UAC | 33.33% |
| 19 | 5'-CCA | 5'-CCA | 66.67% |
| 20 | 5'-GTA | 5'-GUA | 33.33% |
| 21 | 5'-GGC | 5'-GGC | 100% |
| 22 | 5'-ACA | 5'-ACA | 33.33% |
| 23 | 5'-ATC | 5'-AUC | 33.33% |
| 24 | 5'-CTC | 5'-CUC | 66.67% |
| 25 | 5'-AAA | 5'-AAA | 0% |
| 26 | 5'-GCC | 5'-GCC | 100% |
| 27 | 5'-ATG | 5'-AUG | 33.33% |
| 28 | 5'-GAT | 5'-GAU | 33.33% |
| 29 | 5'-CTT | 5'-CUU | 33.33% |
| 30 | 5'-CAA | 5'-CAA | 33.33% |
| 31 | 5'-ATT | 5'-AUU | 0% |
| 32 | 5'-GGG | 5'-GGG | 100% |
| 33 | 5'-CTG | 5'-CUG | 66.67% |
| 34 | 5'-CCT | 5'-CCU | 66.67% |
| 35 | 5'-ACT | 5'-ACU | 33.33% |
| 36 | 5'-GGT | 5'-GGU | 66.67% |
| 37 | 5'-GAC | 5'-GAC | 66.67% |
| 38 | 5'-ATA | 5'-AUA | 0% |
| 39 | 5'-CGC | 5'-CGC | 100% |

TABLE 4-continued

64 Antisense Codons

| No. | Antisense Codons in DNA | Antisense Codons in mRNA | GC Content |
|---|---|---|---|
| 40 | 5'-CCC | 5'-CCC | 100% |
| 41 | 5'-AAT | 5'-AAU | 0% |
| 42 | 5'-TAG | 5'-UAG | 33.33% |
| 43 | 5'-CGG | 5'-CGG | 100% |
| 44 | 5'-TCG | 5'-UCG | 66.67% |
| 45 | 5'-TGA | 5'-UGA | 33.33% |
| 46 | 5'-CGT | 5'-CGU | 66.67% |
| 47 | 5'-CAC | 5'-CAC | 66.67% |
| 48 | 5'-AGC | 5'-AGC | 66.67% |
| 49 | 5'-ACC | 5'-ACC | 66.67% |
| 50 | 5'-GAG | 5'-GAG | 66.67% |
| 51 | 5'-AGG | 5'-AGG | 66.67% |
| 52 | 5'-GCG | 5'-GCG | 100% |
| 53 | 5'-GGA | 5'-GGA | 66.67% |
| 54 | 5'-AGT | 5'-AGU | 33.33% |
| 55 | 5'-AAC | 5'-AAC | 33.33% |
| 56 | 5'-CAG | 5'-CAG | 66.67% |
| 57 | 5'-CCG | 5'-CCG | 100% |
| 58 | 5'-CGA | 5'-CGA | 66.67% |
| 59 | 5'-AAG | 5'-AAG | 33.33% |
| 60 | 5'-ACG | 5'-ACG | 66.67% |
| 61 | 5'-AGA | 5'-AGA | 33.33% |
| 62 | 5'-TTA | 5'-UUA | 0% |
| 63 | 5'-TCA | 5'-UCA | 33.33% |
| 64 | 5'-CTA | 5'-CUA | 33.33% |

GC Content of 64 Antisense Codons: 100%: 8 66.7%: 24 33.3%: 24. 0%: 8

TABLE 5

Two-codon Restriction Endonuclease Recognition Sequences in Coding Regions

| No. | Restriction Enzyme | DNA Recognition Sense Sequence | Recognition Sequence of Amino Acids | DNA Anti-sense Recognition Sequence |
|---|---|---|---|---|
| 1 | Aat II | 5'-GACGTC | NH2-DV | 5'-GACGTC |
| 2 | Acc65 I | 5'-GGTACC | NH2-GT | 5'-GGTACC |
| 3 | Acl I | 5'-AACGTT | NH2-NV | 5'-AACGTT |
| 4 | Afe I | 5'-AGCGCT | NH2-SA | 5'-AGCGCT |
| 5 | Afl II | 5'-CTTAAG | NH2-LK | 5'-CTTAAG |
| 6 | Age I | 5'-ACCGGT | NH2-TG | 5'-ACCGGT |
| 7 | Apa I | 5'-GGGCCC | NH2-GP | 5'-GGGCCC |
| 8 | ApaL I | 5'-GTGCAC | NH2-VH | 5'-GTGCAC |
| 9 | Ase I | 5'-ATTAAT | NH2-IN | 5'-ATTAAT |
| 10 | Avr II | 5'-CCTAGG | NH2-PR | 5'-CCTAGG |
| 11 | BamH I | 5'-GGATCC | NH2-GS | 5'-GGATCC |
| 12 | Bfr B I | 5'-ATGCAT | NH2-MH | 5'-ATGCAT |
| 13 | Bmg B I | 5'-CACGTC | NH2-HV | 5'-GACGTG |
| 14 | Bgl II | 5'-AGATCT | NH2-RS | 5'-AGATCT |
| 15 | Bse Y I | 5'-CCCAGC | NH2-PS | 5'-GCTGGG |
| 16 | Btr I | 5'-CACGTC | NH2-HV | 5'-GACGTG |
| 17 | BsiW I | 5'-CGTACG | NH2-RT | 5'-CGTACG |
| 18 | BspD I | 5'-ATCGAT | NH2-ID | 5'-ATCGAT |
| 19 | BspE I | 5'-TCCGGA | NH2-SG | 5'-TCCGGA |
| 20 | BsrB I | 5'-GAGCGG | NH2-ER | 5'-CCGCTC |
| 21 | BsrG I | 5'-TGTACA | NH2-CT | 5'-TGTACA |
| 22 | BssH II | 5'-GCGCGC | NH2-AR | 5'-GCGCGC |
| 23 | BssS I | 5'-CTCGTG | NH2-LV | 5'-CACGAG |
| 24 | Bst B I | 5'-TTCGAA | NH2-FE | 5'-TTCGAA |
| 25 | BstZ17 I | 5'-GTATAC | NH2-VY | 5'-GTATAC |
| 26 | Cla I | 5'-ATCGAT | NH2-ID | 5'-ATCGAT |
| 27 | Dra I | 5'-TTTAAA | NH2-FK | 5'-TTTAAA |
| 28 | Eag I | 5'-CGGCCG | NH2-RP | 5'-CGGCCG |
| 29 | EcoR I | 5'-GAATTC | NH2-EF | 5'-GAATTC |
| 30 | EcoR V | 5'-GATATC | NH2-DI | 5'-GATATC |
| 31 | Fsp I | 5'-TGCGCA | NH2-CA | 5'-TGCGCA |
| 32 | Hind III | 5'-AAGCTT | NH2-KL | 5'-AAGCTT |
| 33 | Hpa I | 5'-GTTAAC | NH2-VN | 5'-GTTAAC |
| 34 | Kas I | 5'-GGCGCC | NH2-GA | 5'-GGCGCC |
| 35 | Kpn I | 5'-GGTACC | NH2-GT | 5'-GGTACC |
| 36 | Mfe I | 5'-CAATTG | NH2-QL | 5'-CAATTG |
| 37 | Mlu I | 5'-ACGCGT | NH2-TR | 5'-ACGCGT |
| 38 | Msc I | 5'-TGGCCA | NH2-WP | 5'-TGGCCA |
| 39 | Nae I | 5'-GCCGGC | NH2-AG | 5'-GCCGGC |
| 40 | Nar I | 5'-GGCGCC | NH2-GA | 5'-GGCGCC |
| 41 | Nco I | 5'-CCATGG | NH2-PW | 5'-CCATGG |
| 42 | Nde I | 5'-CATATG | NH2-HM | 5'-CATATG |
| 43 | NgoM IV | 5'-GCCGGC | NH2-AG | 5'-GCCGGC |
| 44 | Nhe I | 5'-GCTAGC | NH2-AS | 5'-GCTAGC |
| 45 | Nru I | 5'-TCGCGA | NH2-SR | 5'-TCGCGA |
| 46 | Nsi I | 5'-ATGCAT | NH2-MH | 5'-ATGCAT |
| 47 | PaeR7 I | 5'-CTCGAG | NH2-LE | 5'-CTCGAG |
| 48 | Pci I | 5'-ACATGT | NH2-TC | 5'-ACATGT |
| 49 | Pml I | 5'-CACGTG | NH2-HV | 5'-CACGTG |
| 50 | PspOM I | 5'-GGGCCC | NH2-GP | 5'-GGGCCC |
| 51 | Pst I | 5'-CTGCAG | NH2-LQ | 5'-CTGCAG |
| 52 | Pvu I | 5'-CGATCG | NH2-RS | 5'-CGATCG |
| 53 | Pvu II | 5'-CAGCTG | NH2-QL | 5'-CAGCTG |
| 54 | Sac I | 5'-GAGCTC | NH2-EL | 5'-GAGCTC |
| 55 | Sac II | 5'-CCGCGG | NH2-PR | 5'-CCGCGG |
| 56 | Sal I | 5'-GTCGAC | NH2-VD | 5'-GTCGAC |
| 57 | Sca I | 5'-AGTACT | NH2-ST | 5'-AGTACT |
| 58 | Sfo I | 5'-GGCGCC | NH2-GA | 5'-GGCGCC |
| 59 | Sma I | 5'-CCCGGG | NH2-PG | 5'-CCCGGG |
| 60 | SnaB I | 5'-TACGTA | NH2-YV | 5'-TACGTA |
| 61 | Spe I | 5'-ACTAGT | NH2-TS | 5'-ACTAGT |
| 62 | Sph I | 5'-GCATGC | NH2-AC | 5'-GCATGC |
| 63 | Ssp I | 5'-AATATT | NH2-NI | 5'-AATATT |
| 64 | Stu I | 5'-AGGCCT | NH2-RP | 5'-AGGCCT |
| 65 | Tli I | 5'-CTCGAG | NH2-LE | 5'-CTCGAG |
| 66 | Xba I | 5'-TCTAGA | NH2-SR | 5'-TCTAGA |
| 67 | Xho I | 5'-CTCGAG | NH2-LE | 5'-CTCGAG |
| 68 | Xma I | 5'-CCCGGG | NH2-PG | 5'-CCCGGG |
| 69-1 | Acc I | 5'-GTATAC | NH2-VY | 5'-GTATAC |
| 69-2 | Acc I | 5'-GTCTAC | NH2-VY | 5'-GTAGAC |
| 69-3 | Acc I | 5'-GTAGAC | NH2-VD | 5'-GTCTAC |
| 69-4 | Acc I | 5'-GTCGAC | NH2-VD | 5'-GTCGAC |
| 70-1 | Bme1580 I | 5'-GGGCAC | NH2-GH | 5'-GTGCCC |
| 70-2 | Bme1580 I | 5'-GGGCCC | NH2-GP | 5'-GGGCCC |
| 70-3 | Bme1580 I | 5'-GTGCAC | NH2-VH | 5'-GTGCAC |
| 70-4 | Bme1580 I | 5'-GTGCCC | NH2-VP | 5'-GGGCAC |
| 71-1 | BsaW I | 5'-ACCGGA | NH2-TG | 5'-TCCGGT |
| 71-2 | BsaW I | 5'-ACCGGT | NH2-TG | 5'-ACCGGT |
| 71-3 | BsaW I | 5'-TCCGGA | NH2-SG | 5'-TCCGGA |
| 71-4 | BsaW I | 5'-TCCGGT | NH2-SG | 5'-ACCGGA |
| 72-1 | BsiHKA I | 5'-GAGCAC | NH2-EH | 5'-GTGCTC |
| 72-2 | BsiHKA I | 5'-GAGCTC | NH2-EL | 5'-GAGCTC |
| 72-3 | BsiHKA I | 5'-GTGCAC | NH2-VH | 5'-GTGCAC |
| 72-4 | BsiHKA I | 5'-GTGCTC | NH2-VL | 5'-GAGCAC |
| 73-1 | Bsp1286 I | 5'-GGGCCC | NH2-GP | 5'-GGGCCC |
| 73-2 | Bsp1286 I | 5'-GAGCCC | NH2-EP | 5'-GGGCTC |
| 73-3 | Bsp1286 I | 5'-GTGCCC | NH2-VP | 5'-GGGCAC |
| 73-4 | Bsp1286 I | 5'-GAGCAC | NH2-EH | 5'-GTGCTC |
| 73-5 | Bsp1286 I | 5'-GTGCAC | NH2-VH | 5'-GTGCAC |
| 73-6 | Bsp1286 I | 5'-GAGCTC | NH2-EL | 5'-GAGCTC |
| 74-1 | MspA1 I | 5'-CAGCGG | NH2-QR | 5'-CCGCTG |
| 74-2 | MspA1 I | 5'-CAGCTG | NH2-QL | 5'-CAGCTG |
| 74-3 | MspA1 I | 5'-CCGCGG | NH2-PR | 5'-CCGCGG |
| 74-4 | MspA1 I | 5'-CCGCTG | NH2-PL | 5'-CAGCGG |
| 75-1 | Sty I | 5'-CCAAGG | NH2-PR | 5'-CCTTGG |
| 75-2 | Sty I | 5'-CCTAGG | NH2-PR | 5'-CCTAGG |
| 75-3 | Sty I | 5'-CCATGG | NH2-PW | 5'-CCATGG |
| 75-4 | Sty I | 5'-CCTTGG | NH2-PW | 5'-CCAAGG |

TABLE 6

Two-codon Restriction Endonuclease Recognition Sequences in Non-coding Regions

| No. | Restriction Enzyme | DNA Recognition Sense Sequence | Recognition Sequence of Amino Acids | DNA Anti-sense Recognition Sequence |
|---|---|---|---|---|
| 1 | Aat II | 5'-GACGTC | NH2-DV | 5'-GACGTC |
| 2 | Acc65 I | 5'-GGTACC | NH2-GT | 5'-GGTACC |
| 3 | Acl I | 5'-AACGTT | NH2-NV | 5'-AACGTT |
| 4 | Afe I | 5'-AGCGCT | NH2-SA | 5'-AGCGCT |
| 5 | Afl II | 5'-CTTAAG | NH2-LK | 5'-CTTAAG |
| 6 | Age I | 5'-ACCGGT | NH2-TG | 5'-ACCGGT |
| 7 | Apa I | 5'-GGGCCC | NH2-GP | 5'-GGGCCC |
| 8 | ApaL I | 5'-GTGCAC | NH2-VH | 5'-GTGCAC |
| 9 | Ase I | 5'-ATTAAT | NH2-IN | 5'-ATTAAT |
| 10 | Avr II | 5'-CCTAGG | NH2-PR | 5'-CCTAGG |
| 11 | BamH I | 5'-GGATCC | NH2-GS | 5'-GGATCC |
| 12 | Bfr B I | 5'-ATGCAT | NH2-MH | 5'-ATGCAT |
| 13 | Bmg B I | 5'-CACGTC | NH2-HV | 5'-GACGTG |
| 14 | Bgl II | 5'-AGATCT | NH2-RS | 5'-AGATCT |
| 15 | Bse Y I | 5'-CCCAGC | NH2-PS | 5'-GCTGGG |
| 16 | Btr I | 5'-CACGTC | NH2-HV | 5'-GACGTG |
| 17 | BsiW I | 5'-CGTACG | NH2-RT | 5'-CGTACG |
| 18 | BspD I | 5'-ATCGAT | NH2-ID | 5'-ATCGAT |
| 19 | BspE I | 5'-TCCGGA | NH2-SG | 5'-TCCGGA |
| 20 | BsrB I | 5'-GAGCGG | NH2-ER | 5'-CCGCTC |
| 21 | BsrG I | 5'-TGTACA | NH2-CT | 5'-TGTACA |
| 22 | BssH II | 5'-GCGCGC | NH2-AR | 5'-GCGCGC |
| 23 | BssS I | 5'-CTCGTG | NH2-LV | 5'-CACGAG |
| 24 | Bst B I | 5'-TTCGAA | NH2-FE | 5'-TTCGAA |
| 25 | BstZ17 I | 5'-GTATAC | NH2-VY | 5'-GTATAC |
| 26 | Cla I | 5'-ATCGAT | NH2-ID | 5'-ATCGAT |
| 27 | Dra I | 5'-TTTAAA | NH2-FK | 5'-TTTAAA |
| 28 | Eag I | 5'-CGGCCG | NH2-RP | 5'-CGGCCG |
| 29 | EcoR I | 5'-GAATTC | NH2-EF | 5'-GAATTC |
| 30 | EcoR V | 5'-GATATC | NH2-DI | 5'-GATATC |
| 31 | Fsp I | 5'-TGCGCA | NH2-CA | 5'-TGCGCA |
| 32 | Hind III | 5'-AAGCTT | NH2-KL | 5'-AAGCTT |
| 33 | Hpa I | 5'-GTTAAC | NH2-VN | 5'-GTTAAC |
| 34 | Kas I | 5'-GGCGCC | NH2-GA | 5'-GGCGCC |
| 35 | Kpn I | 5'-GGTACC | NH2-GT | 5'-GGTACC |
| 36 | Mfe I | 5'-CAATTG | NH2-QL | 5'-CAATTG |
| 37 | Mlu I | 5'-ACGCGT | NH2-TR | 5'-ACGCGT |
| 38 | Msc I | 5'-TGGCCA | NH2-WP | 5'-TGGCCA |
| 39 | Nae I | 5'-GCCGGC | NH2-AG | 5'-GCCGGC |
| 40 | Nar I | 5'-GGCGCC | NH2-GA | 5'-GGCGCC |
| 41 | Nco I | 5'-CCATGG | NH2-PW | 5'-CCATGG |
| 42 | Nde I | 5'-CATATG | NH2-HM | 5'-CATATG |
| 43 | NgoM IV | 5'-GCCGGC | NH2-AG | 5'-GCCGGC |
| 44 | Nhe I | 5'-GCTAGC | NH2-AS | 5'-GCTAGC |
| 45 | Nru I | 5'-TCGCGA | NH2-SR | 5'-TCGCGA |
| 46 | Nsi I | 5'-ATGCAT | NH2-MH | 5'-ATGCAT |
| 47 | PaeR7 I | 5'-CTCGAG | NH2-LE | 5'-CTCGAG |
| 48 | Pci I | 5'-ACATGT | NH2-TC | 5'-ACATGT |
| 49 | Pml I | 5'-CACGTG | NH2-HV | 5'-CACGTG |
| 50 | PspOM I | 5'-GGGCCC | NH2-GP | 5'-GGGCCC |
| 51 | Pst I | 5'-CTGCAG | NH2-LQ | 5'-CTGCAG |
| 52 | Pvu I | 5'-CGATCG | NH2-RS | 5'-CGATCG |
| 53 | Pvu II | 5'-CAGCTG | NH2-QL | 5'-CAGCTG |
| 54 | Sac I | 5'-GAGCTC | NH2-EL | 5'-GAGCTC |
| 55 | Sac II | 5'-CCGCGG | NH2-PR | 5'-CCGCGG |
| 56 | Sal I | 5'-GTCGAC | NH2-VD | 5'-GTCGAC |
| 57 | Sca I | 5'-AGTACT | NH2-ST | 5'-AGTACT |
| 58 | Sfo I | 5'-GGCGCC | NH2-GA | 5'-GGCGCC |
| 59 | Sma I | 5'-CCCGGG | NH2-PG | 5'-CCCGGG |
| 60 | SnaB I | 5'-TACGTA | NH2-YV | 5'-TACGTA |
| 61 | Spe I | 5'-ACTAGT | NH2-TS | 5'-ACTAGT |
| 62 | Sph I | 5'-GCATGC | NH2-AC | 5'-GCATGC |
| 63 | Ssp I | 5'-AATATT | NH2-NI | 5'-AATATT |
| 64 | Stu I | 5'-AGGCCT | NH2-RP | 5'-AGGCCT |
| 65 | Tli I | 5'-CTCGAG | NH2-LE | 5'-CTCGAG |
| 66 | Xba I | 5'-TCTAGA | NH2-SR | 5'-TCTAGA |
| 67 | Xho I | 5'-CTCGAG | NH2-LE | 5'-CTCGAG |
| 68 | Xma I | 5'-CCCGGG | NH2-PG | 5'-CCCGGG |
| 69-1 | Acc I | 5'-GTATAC | NH2-VY | 5'-GTATAC |
| 69-2 | Acc I | 5'-GTCTAC | NH2-VY | 5'-GTAGAC |
| 69-3 | Acc I | 5'-GTAGAC | NH2-VD | 5'-GTCTAC |
| 69-4 | Acc I | 5'-GTCGAC | NH2-VD | 5'-GTCGAC |
| 70-1 | Bme1580 I | 5'-GGGCAC | NH2-GH | 5'-GTGCCC |
| 70-2 | Bme1580 I | 5'-GGGCCC | NH2-GP | 5'-GGGCCC |
| 70-3 | Bme1580 I | 5'-GTGCAC | NH2-VH | 5'-GTGCAC |
| 70-4 | Bme1580 I | 5'-GTGCCC | NH2-VP | 5'-GGGCAC |
| 71-1 | BsaW I | 5'-ACCGGA | NH2-TG | 5'-TCCGGT |
| 71-2 | BsaW I | 5'-ACCGGT | NH2-TG | 5'-ACCGGT |
| 71-3 | BsaW I | 5'-TCCGGA | NH2-SG | 5'-TCCGGA |
| 71-4 | BsaW I | 5'-TCCGGT | NH2-SG | 5'-ACCGGA |
| 72-1 | BsiHKA I | 5'-GAGCAC | NH2-EH | 5'-GTGCTC |
| 72-2 | BsiHKA I | 5'-GAGCTC | NH2-EL | 5'-GAGCTC |
| 72-3 | BsiHKA I | 5'-GTGCAC | NH2-VH | 5'-GTGCAC |
| 72-4 | BsiHKA I | 5'-GTGCTC | NH2-VL | 5'-GAGCAC |
| 73-1 | Bsp1286 I | 5'-GGGCCC | NH2-GP | 5'-GGGCCC |
| 73-2 | Bsp1286 I | 5'-GAGCCC | NH2-EP | 5'-GGGCTC |
| 73-3 | Bsp1286 I | 5'-GTGCCC | NH2-VP | 5'-GGGCAC |
| 73-4 | Bsp1286 I | 5'-GAGCAC | NH2-EH | 5'-GTGCTC |
| 73-5 | Bsp1286 I | 5'-GTGCAC | NH2-VH | 5'-GTGCAC |
| 73-6 | Bsp1286 I | 5'-GAGCTC | NH2-EL | 5'-GAGCTC |
| 74-1 | MspA1 I | 5'-CAGCGG | NH2-QR | 5'-CCGCTG |
| 74-2 | MspA1 I | 5'-CAGCTG | NH2-QL | 5'-CAGCTG |
| 74-3 | MspA1 I | 5'-CCGCGG | NH2-PR | 5'-CCGCGG |
| 74-4 | MspA1 I | 5'-CCGCTG | NH2-PL | 5'-CAGCGG |
| 75-1 | Sty I | 5'-CCAAGG | NH2-PR | 5'-CCTTGG |
| 75-2 | Sty I | 5'-CCTAGG | NH2-PR | 5'-CCTAGG |
| 75-3 | Sty I | 5'-CCATGG | NH2-PW | 5'-CCATGG |
| 75-4 | Sty I | 5'-CCTTGG | NH2-PW | 5'-CCAAGG |
| 76 | Bcl I | 5'-TGATCA | n/a | 5'-TGATCA |
| 77 | BspH I | 5'-TCATGA | n/a | 5'-TCATGA |
| 78 | Psi I | 5'-TTATAA | n/a | 5'-TTATAA |

TABLE 7

5'-Start Codon Oriented ORF Sense Sequence Deducing

| Codon Position | Nucleotide Position | | | Length of Nucleotide Sequence 3n (mers) | Number of 3n-length-long Nucleotide Sequences |
|---|---|---|---|---|---|
| 1 | +1, | +2, | +3, | 3 mers | $61^{1-1}$ |
| 2 | +4, | +5, | +6, | 6 mers | $61^{2-1}$ |
| 3 | +7, | +8, | +9, | 9 mers | $61^{3-1}$ |
| 4 | +10, | +11, | +12, | 12 mers | $61^{4-1}$ |
| 5 | +13, | +14, | +15, | 15 mers | $61^{5-1}$ |
| 6 | +16, | +17, | +18, | 18 mers | $61^{6-1}$ |
| 7 | +19, | +20, | +21, | 21 mers | $61^{7-1}$ |
| 8 | +22, | +23, | +24, | 24 mers | $61^{8-1}$ |
| 9 | +25, | +26, | +27, | 27 mers | $61^{9-1}$ |
| 10 | +28, | +29, | +30, | 30 mers | $61^{10-1}$ |
| 11 | +31, | +32, | +33, | 33 mers | $61^{11-1}$ |
| 12 | +34, | +35, | +36, | 36 mers | $61^{12-1}$ |
| 13 | +37, | +38, | +39, | 39 mers | $61^{13-1}$ |
| 14 | +40, | +41, | +42, | 42 mers | $61^{14-1}$ |
| 15 | +43, | +44, | +45, | 45 mers | $61^{15-1}$ |
| 16 | +46, | +47, | +48, | 48 mers | $61^{16-1}$ |
| 17 | +49, | +50, | +51, | 51 mers | $61^{17-1}$ |
| 18 | +52, | +53, | +54, | 54 mers | $61^{18-1}$ |
| 19 | +55, | +56, | +57, | 57 mers | $61^{19-1}$ |
| 20 | +58, | +59, | +60, | 60 mers | $61^{20-1}$ |
| 21 | +61, | +62, | +63, | 63 mers | $61^{21-1}$ |
| 22 | +64, | +65, | +66, | 66 mers | $61^{22-1}$ |
| 23 | +67, | +68, | +69, | 69 mers | $61^{23-1}$ |
| 24 | +70, | +71, | +72, | 72 mers | $61^{24-1}$ |
| 25 | +73, | +74, | +75, | 75 mers | $61^{25-1}$ |
| 26 | +76, | +77, | +78, | 78 mers | $61^{26-1}$ |
| 27 | +79, | +80, | +81, | 81 mers | $61^{27-1}$ |
| 28 | +82, | +83, | +84, | 84 mers | $61^{28-1}$ |
| 29 | +85, | +86, | +87, | 87 mers | $61^{29-1}$ |
| 30 | +88, | +89, | +90, | 90 mers | $61^{30-1}$ |

TABLE 7-continued

5'-Start Codon Oriented ORF Sense Sequence Deducing

| Codon Position | Nucleotide Position | | | Length of Nucleotide Sequence 3n (mers) | Number of 3n-length-long Nucleotide Sequences |
|---|---|---|---|---|---|
| 31 | +91, | +92, | +93, | 93 mers | $61^{31-1}$ |
| 32 | +94, | +95, | +96, | 96 mers | $61^{32-1}$ |
| 33 | +97, | +98, | +99, | 99 mers | $61^{33-1}$ |
| 34 | +100, | +101, | +102, | 102 mers | $61^{34-1}$ |
| n | +(3n − 2), | +(3n − 1), | +3n | 3n mers | $61^{n-m}/m = 1$ |

TABLE 8

3'-Stop Codon Oriented ORF Sense Sequence Deducing

| Codon Position | Nucleotide Position | | | Length of Nucleotide Sequence 3n (mers) | Number of 3n-length-long Nucleotide Sequences |
|---|---|---|---|---|---|
| 1 | +3, | +2, | +1, | 3 mers | $61^{1-1}$ |
| 2 | +6, | +5, | +4, | 6 mers | $61^{2-1}$ |
| 3 | +9, | +8, | +7, | 9 mers | $61^{3-1}$ |
| 4 | +12, | +11, | +10, | 12 mers | $61^{4-1}$ |
| 5 | +15, | +14, | +13, | 15 mers | $61^{5-1}$ |
| 6 | +18, | +17, | +16, | 18 mers | $61^{6-1}$ |
| 7 | +21, | +20, | +19, | 21 mers | $61^{7-1}$ |
| 8 | +24, | +23, | +22, | 24 mers | $61^{8-1}$ |
| 9 | +27, | +26, | +25, | 27 mers | $61^{9-1}$ |
| 10 | +30, | +29, | +28, | 30 mers | $61^{10-1}$ |
| 11 | +33, | +32, | +31, | 33 mers | $61^{11-1}$ |
| 12 | +36, | +35, | +34, | 36 mers | $61^{12-1}$ |
| 13 | +39, | +38, | +37, | 39 mers | $61^{13-1}$ |
| 14 | +42, | +41, | +40, | 42 mers | $61^{14-1}$ |
| 15 | +45, | +44, | +43, | 45 mers | $61^{15-1}$ |
| 16 | +48, | +47, | +46, | 48 mers | $61^{16-1}$ |
| 17 | +51, | +50, | +49, | 51 mers | $61^{17-1}$ |
| 18 | +54, | +53, | +52, | 54 mers | $61^{18-1}$ |
| 19 | +57, | +56, | +55, | 57 mers | $61^{19-1}$ |
| 20 | +60, | +59, | +58, | 60 mers | $61^{20-1}$ |
| 21 | +63, | +62, | +61, | 63 mers | $61^{21-1}$ |
| 22 | +66, | +65, | +64, | 66 mers | $61^{22-1}$ |
| 23 | +69, | +68, | +67, | 69 mers | $61^{23-1}$ |
| 24 | +72, | +71, | +70, | 72 mers | $61^{24-1}$ |
| 25 | +75, | +74, | +73, | 75 mers | $61^{25-1}$ |
| 26 | +78, | +77, | +76, | 78 mers | $61^{26-1}$ |
| 27 | +81, | +80, | +79, | 81 mers | $61^{27-1}$ |
| 28 | +84, | +83, | +82, | 84 mers | $61^{28-1}$ |
| 29 | +87, | +86, | +85, | 87 mers | $61^{29-1}$ |
| 30 | +90, | +89, | +88, | 90 mers | $61^{30-1}$ |
| 31 | +93, | +92, | +91, | 93 mers | $61^{31-1}$ |
| 32 | +96, | +95, | +94, | 96 mers | $61^{32-1}$ |
| 33 | +99, | +98, | +97, | 99 mers | $61^{33-1}$ |
| 34 | +102, | +101, | +100, | 102 mers | $61^{34-1}$ |
| n | +3n, | +(3n − 1), | +(3n − 2) | 3n mers | $61^{n-m}/m = 1$ |

TABLE 9

3'-Start Codon Oriented 5'-UTR Sense Sequence Deducing

| Codon Position | Nucleotide Position | | | Length of Nucleotide Sequence 3n (mers) | Number of 3n-length-long Nucleotide Sequences |
|---|---|---|---|---|---|
| 1 | +1, | +2, | +3, | 3 mers | $64^{1-1}$ |
| 2 | −3, | −2, | −1, | 6 mers | $64^{2-1}$ |
| 3 | −6, | −5, | −4, | 9 mers | $64^{3-1}$ |
| 4 | −9, | −8, | −7, | 12 mers | $64^{4-1}$ |
| 5 | −12, | −11, | −11, | 15 mers | $64^{5-1}$ |
| 6 | −15, | −14, | −13, | 18 mers | $64^{6-1}$ |
| 7 | −18, | −17, | −16, | 21 mers | $64^{7-1}$ |
| 8 | −21, | −20, | −19, | 24 mers | $64^{8-1}$ |
| 9 | −24, | −23, | −22, | 27 mers | $64^{9-1}$ |
| 10 | −27, | −26, | −25, | 30 mers | $64^{10-1}$ |
| 11 | −30, | −29, | −28, | 33 mers | $64^{11-1}$ |
| 12 | −33, | −32, | −31, | 36 mers | $64^{12-1}$ |
| 13 | −36, | −35, | −34, | 39 mers | $64^{13-1}$ |

TABLE 9-continued

3'-Start Codon Oriented 5'-UTR Sense Sequence Deducing

| Codon Position | Nucleotide Position | | | Length of Nucleotide Sequence 3n (mers) | Number of 3n-length-long Nucleotide Sequences |
|---|---|---|---|---|---|
| 14 | −39, | −38, | −37, | 42 mers | $64^{14-1}$ |
| 15 | −42, | −41, | −40, | 45 mers | $64^{15-1}$ |
| 16 | −45, | −44, | −43, | 48 mers | $64^{16-1}$ |
| 17 | −48, | −47, | −46, | 51 mers | $64^{17-1}$ |
| 18 | −51, | −50, | −49, | 54 mers | $64^{18-1}$ |
| 19 | −54, | −53, | −52, | 57 mers | $64^{19-1}$ |
| 20 | −57, | −56, | −55, | 60 mers | $64^{20-1}$ |
| 21 | −60, | −59, | −58, | 63 mers | $64^{21-1}$ |
| 22 | −63, | −62, | −61, | 66 mers | $64^{22-1}$ |
| 23 | −66, | −65, | −64, | 69 mers | $64^{23-1}$ |
| 24 | −69, | −68, | −67, | 72 mers | $64^{24-1}$ |
| 25 | −72, | −71, | −70, | 75 mers | $64^{25-1}$ |
| 26 | −75, | −74, | −73, | 78 mers | $64^{26-1}$ |
| 27 | −78, | −77, | −76, | 81 mers | $64^{27-1}$ |
| 28 | −81, | −80, | −79, | 84 mers | $64^{28-1}$ |
| 29 | −84, | −83, | −82, | 87 mers | $64^{29-1}$ |
| 30 | −87, | −86, | −85, | 90 mers | $64^{30-1}$ |
| 31 | −90, | −89, | −88, | 93 mers | $64^{31-1}$ |
| 32 | −93, | −92, | −91, | 96 mers | $64^{32-1}$ |
| 33 | −96, | −95, | −94, | 99 mers | $64^{33-1}$ |
| 34 | −99, | −98, | −97, | 102 mers | $64^{34-1}$ |
| n = m, m = 1 | $3(1-n)+1,$ | $3(1-n)+2,$ | $3(1-n)+3$ | 3n mers | $64^{n-m}$ |
| n > m, m = 1 | $3(1-n),$ | $3(1-n)+1,$ | $3(1-n)+2$ | −3n mers | m = 1 |

TABLE 10

5'-Stop Codon Oriented 3'-UTR Sense Sequence Deducing

| Codon Position | Nucleotide Position | | | Length of Nucleotide Sequence 3n (mers) | Number of 3n-length-long Nucleotide Sequences |
|---|---|---|---|---|---|
| 1 | +1, | +2, | +3, | 3 mers | $64^{1-1}$ |
| 2 | +4, | +5, | +6 | 6 mers | $64^{2-1}$ |
| 3 | +7, | +8, | +9, | 9 mers | $64^{3-1}$ |
| 4 | +10, | +11, | +12, | 12 mers | $64^{4-1}$ |
| 5 | +13, | +14, | +15, | 15 mers | $64^{5-1}$ |
| 6 | +16, | +17, | +18, | 18 mers | $64^{6-1}$ |
| 7 | +19, | +20, | +21, | 21 mers | $64^{7-1}$ |
| 8 | +22, | +23, | +24, | 24 mers | $64^{8-1}$ |
| 9 | +25, | +26, | +27, | 27 mers | $64^{9-1}$ |
| 10 | +28, | +29, | +30, | 30 mers | $64^{10-1}$ |
| 11 | +31, | +32, | +33, | 33 mers | $64^{11-1}$ |
| 12 | +34, | +35, | +36, | 36 mers | $64^{12-1}$ |
| 13 | +37, | +38, | +39, | 39 mers | $64^{13-1}$ |
| 14 | +40, | +41, | +42, | 42 mers | $64^{14-1}$ |
| 15 | +43, | +44, | +45, | 45 mers | $64^{15-1}$ |
| 16 | +46, | +47, | +48, | 48 mers | $64^{16-1}$ |
| 17 | +49, | +50, | +51, | 51 mers | $64^{17-1}$ |
| 18 | +52, | +53, | +54, | 54 mers | $64^{18-1}$ |
| 19 | +55, | +56, | +57, | 57 mers | $64^{19-1}$ |
| 20 | +58, | +59, | +60, | 60 mers | $64^{20-1}$ |
| 21 | +61, | +62, | +63, | 63 mers | $64^{21-1}$ |
| 22 | +64, | +65, | +66, | 66 mers | $64^{22-1}$ |
| 23 | +67, | +68, | +69, | 69 mers | $64^{23-1}$ |
| 24 | +70, | +71, | +72, | 72 mers | $64^{24-1}$ |
| 25 | +73, | +74, | +75, | 75 mers | $64^{25-1}$ |
| 26 | +76, | +77, | +78, | 78 mers | $64^{26-1}$ |
| 27 | +79, | +80, | +81, | 81 mers | $64^{27-1}$ |
| 28 | +82, | +83, | +84, | 84 mers | $64^{28-1}$ |
| 29 | +85, | +86, | +87, | 87 mers | $64^{29-1}$ |
| 30 | +88, | +89, | +90, | 90 mers | $64^{30-1}$ |
| 31 | +91, | +92, | +93, | 93 mers | $64^{31-1}$ |
| 32 | +94, | +95, | +96, | 96 mers | $64^{32-1}$ |
| 33 | +97, | +98, | +99, | 99 mers | $64^{33-1}$ |
| 34 | +100, | +101, | +102, | 102 mers | $64^{34-1}$ |
| n | $+(3n-2),$ | $+(3n-1),$ | $+3n$ | 3n mers | $64^{n-m}/m=1$ |

TABLE 11

3'-Anti-sense Start Codon Oriented Anti-sense ORF Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 1 | +3, | +2, | +1, | 3 mers | $61^{1-1}$ |
| 2 | +6, | +5, | +4, | 6 mers | $61^{2-1}$ |
| 3 | +9, | +8, | +7, | 9 mers | $61^{3-1}$ |
| 4 | +12, | +11, | +10, | 12 mers | $61^{4-1}$ |
| 5 | +15, | +14, | +13, | 15 mers | $61^{5-1}$ |
| 6 | +18, | +7, | +16, | 18 mers | $61^{6-1}$ |
| 7 | +21, | +20, | +19, | 21 mers | $61^{7-1}$ |
| 8 | +24, | +23, | +22, | 24 mers | $61^{8-1}$ |
| 9 | +27, | +26, | +25, | 27 mers | $61^{9-1}$ |
| 10 | +30, | +29, | +28, | 30 mers | $61^{10-1}$ |
| 11 | +33, | +32, | +31, | 33 mers | $61^{11-1}$ |
| 12 | +36, | +35, | +34, | 36 mers | $61^{12-1}$ |
| 13 | +39, | +38, | +37, | 39 mers | $61^{13-1}$ |
| 14 | +42, | +41, | +40, | 42 mers | $61^{14-1}$ |
| 15 | +45, | +44, | +43, | 45 mers | $61^{15-1}$ |
| 16 | +48, | +47, | +46, | 48 mers | $61^{16-1}$ |
| 17 | +51, | +50, | +49, | 51 mers | $61^{17-1}$ |
| 18 | +54, | +53, | +52, | 54 mers | $61^{18-1}$ |
| 19 | +57, | +56, | +55, | 57 mers | $61^{19-1}$ |
| 20 | +60, | +59, | +58, | 60 mers | $61^{20-1}$ |
| 21 | +63, | +62, | +61, | 63 mers | $61^{21-1}$ |
| 22 | +66, | +65, | +64, | 66 mers | $61^{22-1}$ |
| 23 | +69, | +68, | +67, | 69 mers | $61^{23-1}$ |
| 24 | +72, | +71, | +70, | 72 mers | $61^{24-1}$ |
| 25 | +75, | +74, | +73, | 75 mers | $61^{25-1}$ |
| 26 | +78, | +77, | +76, | 78 mers | $61^{26-1}$ |
| 27 | +81, | +80, | +79, | 81 mers | $61^{27-1}$ |
| 28 | +84, | +83, | +82, | 84 mers | $61^{28-1}$ |
| 29 | +87, | +86, | +85, | 81 mers | $61^{29-1}$ |
| 30 | +90, | +89, | +88, | 90 mers | $61^{30-1}$ |
| 31 | +93, | +92, | +91, | 93 mers | $61^{31-1}$ |
| 32 | +96, | +95, | +94, | 96 mers | $61^{32-1}$ |
| 33 | +99, | +98, | +97, | 99 mers | $61^{33-1}$ |
| 34 | +102, | +101, | +100, | 102 mers | $61^{34-1}$ |
| n | +3n, | +(3n − 1), | +(3n − 2) | 3n mers | $61^{n-m}/m = 1$ |

TABLE 12

5'-Anti-sense Stop Codon Oriented Anti-sense ORF Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 1 | +1, | +2, | +3, | 3 mers | $61^{1-1}$ |
| 2 | +4, | +5, | +6, | 6 mers | $61^{2-1}$ |
| 3 | +7, | +8, | +9, | 9 mers | $61^{3-1}$ |
| 4 | +10, | +11, | +12, | 12 mers | $61^{4-1}$ |
| 5 | +13, | +14, | +15, | 15 mers | $61^{5-1}$ |
| 6 | +16, | +17, | +18, | 18 mers | $61^{6-1}$ |
| 7 | +19, | +20, | +21, | 21 mers | $61^{7-1}$ |
| 8 | +22, | +23, | +24, | 24 mers | $61^{8-1}$ |
| 9 | +25, | +26, | +27, | 27 mers | $61^{9-1}$ |
| 10 | +28, | +29, | +30, | 30 mers | $61^{10-1}$ |
| 11 | +31, | +32, | +33, | 33 mers | $61^{11-1}$ |
| 12 | +34, | +35, | +36, | 36 mers | $61^{12-1}$ |
| 13 | +37, | +38, | +39, | 39 mers | $61^{13-1}$ |
| 14 | +40, | +41, | +42, | 42 mers | $61^{14-1}$ |
| 15 | +43, | +44, | +45, | 45 mers | $61^{15-1}$ |
| 16 | +46, | +47, | +48, | 48 mers | $61^{16-1}$ |
| 17 | +49, | +50, | +51, | 51 mers | $61^{17-1}$ |
| 18 | +52, | +53, | +54, | 54 mers | $61^{18-1}$ |
| 19 | +55, | +56, | +57, | 57 mers | $61^{19-1}$ |
| 20 | +58, | +59, | +60, | 60 mers | $61^{20-1}$ |
| 21 | +61, | +62, | +63, | 63 mers | $61^{21-1}$ |
| 22 | +64, | +65, | +66, | 66 mers | $61^{22-1}$ |
| 23 | +67, | +68, | +69, | 69 mers | $61^{23-1}$ |
| 24 | +70, | +71, | +72, | 72 mers | $61^{24-1}$ |
| 25 | +73, | +74, | +75, | 75 mers | $61^{25-1}$ |
| 26 | +76, | +77, | +78, | 78 mers | $61^{26-1}$ |
| 27 | +79, | +80, | +81, | 81 mers | $61^{27-1}$ |
| 28 | +82, | +83, | +84, | 84 mers | $61^{28-1}$ |

TABLE 12-continued

5'-Anti-sense Stop Codon Oriented Anti-sense ORF Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 29 | +85, | +86, | +87, | 87 mers | $61^{29-1}$ |
| 30 | +88, | +89, | +90, | 90 mers | $61^{30-1}$ |
| 31 | +91, | +92, | +93, | 93 mers | $61^{31-1}$ |
| 32 | +94, | +95, | +96, | 96 mers | $61^{32-1}$ |
| 33 | +97, | +98, | +99, | 99 mers | $61^{33-1}$ |
| 34 | +100, | +101, | +102, | 102 mers | $61^{34-1}$ |
| n | +(3n − 2), | +(3n − 1), | +3n | 3n mers | $61^{n-m}/m = 1$ |

TABLE 13

5'-Anti-sense Start Codon Oriented 5'-UTR Anti-sense Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 1 | +3, | +2, | +1, | 3 mers | $64^{1-1}$ |
| 2 | −1, | −2, | −3, | 6 mers | $64^{2-1}$ |
| 3 | −4, | −5, | −6, | 9 mers | $64^{3-1}$ |
| 4 | −7, | −8, | −9, | 12 mers | $64^{4-1}$ |
| 5 | −10, | −11, | −12, | 15 mers | $64^{5-1}$ |
| 6 | −13, | −14, | −15, | 18 mers | $64^{6-1}$ |
| 7 | −16, | −17, | −18, | 21 mers | $64^{7-1}$ |
| 8 | −19, | −20, | −21, | 24 mers | $64^{8-1}$ |
| 9 | −22, | −23, | −24, | 27 mers | $64^{9-1}$ |
| 10 | −25, | −26, | −27, | 30 mers | $64^{10-1}$ |
| 11 | −28, | −29, | −30, | 33 mers | $64^{11-1}$ |
| 12 | −31, | −32, | −33, | 36 mers | $64^{12-1}$ |
| 13 | −34, | −35, | −36, | 39 mers | $64^{13-1}$ |
| 14 | −37, | −38, | −39, | 42 mers | $64^{14-1}$ |
| 15 | −40, | −41, | −42, | 45 mers | $64^{15-1}$ |
| 16 | −44, | −44, | −45, | 48 mers | $64^{16-1}$ |
| 17 | −46, | −47, | −48, | 51 mers | $64^{17-1}$ |
| 18 | −49, | −50, | −51, | 54 mers | $64^{18-1}$ |
| 19 | −52, | −53, | −54, | 57 mers | $64^{19-1}$ |
| 20 | −55, | −56, | −57, | 60 mers | $64^{20-1}$ |
| 21 | −58, | −59, | −60, | 63 mers | $64^{21-1}$ |
| 22 | −61, | −62, | −63, | 66 mers | $64^{22-1}$ |
| 23 | −64, | −65, | −66, | 69 mers | $64^{23-1}$ |
| 24 | −67, | −68, | −69, | 72 mers | $64^{24-1}$ |
| 25 | −70, | −71, | −72, | 75 mers | $64^{25-1}$ |
| 26 | −73, | −74, | −75, | 78 mers | $64^{26-1}$ |
| 27 | −76, | −77, | −78, | 81 mers | $64^{27-1}$ |
| 28 | −79, | −80, | −81, | 84 mers | $64^{28-1}$ |
| 29 | −82, | −83, | −84, | 87 mers | $64^{29-1}$ |
| 30 | −85, | −86, | −87, | 90 mers | $64^{30-1}$ |
| 31 | −88, | −89, | −90, | 93 mers | $64^{31-1}$ |
| 32 | −91, | −92, | −93, | 96 mers | $64^{32-1}$ |
| 33 | −94, | −95, | −96, | 99 mers | $64^{33-1}$ |
| 34 | −97, | −98, | −99, | 102 mers | $64^{34-1}$ |
| n = m, m = 1 | 3(1 − n) + 3, | 3(1 − n) + 2, | 3(1 − n) + 1 | 3n mers | $64^{n-m}$ |
| n > m, m = 1 | 3(1 − n) + 2, | 3(1 − n) + 1, | 3(1 − n) | −3n mers | m = 1 |

TABLE 14

3'-Anti-sense Stop Codon Oriented 3'-UTR Anti-sense Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 1 | +3, | +2, | +1, | 3 mers | $64^{1-1}$ |
| 2 | +6, | +5, | +4, | 6 mers | $64^{2-1}$ |
| 3 | +9, | +8, | +7, | 9 mers | $64^{3-1}$ |
| 4 | +12, | +11, | +10, | 12 mers | $64^{4-1}$ |
| 5 | +15, | +14, | +13, | 15 mers | $64^{5-1}$ |
| 6 | +18, | +17, | +16, | 18 mers | $64^{6-1}$ |
| 7 | +21, | +20, | +19, | 21 mers | $64^{7-1}$ |

TABLE 14-continued

3'-Anti-sense Stop Codon Oriented 3'-UTR Anti-sense Sequence Deducing

| Anti-sense Codon Position | Nucleotide Position | | | Length of Nucleotide Sequence 3n (mers) | Number of 3n-length-long Nucleotide Sequences |
|---|---|---|---|---|---|
| 8 | +24, | +23, | +22, | 24 mers | $64^{8-1}$ |
| 9 | +27, | +26, | +25, | 27 mers | $64^{9-1}$ |
| 10 | +30, | +29, | +28, | 30 mers | $64^{10-1}$ |
| 11 | +33, | +32, | +31, | 33 mers | $64^{11-1}$ |
| 12 | +36, | +35, | +34, | 36 mers | $64^{12-1}$ |
| 13 | +39, | +38, | +37, | 39 mers | $64^{13-1}$ |
| 14 | +42, | +41, | +40, | 42 mers | $64^{14-1}$ |
| 15 | +45, | +44, | +43, | 45 mers | $64^{15-1}$ |
| 16 | +48, | +47, | +46, | 48 mers | $64^{16-1}$ |
| 17 | +51, | +50, | +49, | 51 mers | $64^{17-1}$ |
| 18 | +54, | +53, | +52, | 54 mers | $64^{18-1}$ |
| 19 | +57, | +56, | +55, | 57 mers | $64^{19-1}$ |
| 20 | +60, | +59, | +58, | 60 mers | $64^{20-1}$ |
| 21 | +63, | +62, | +61, | 63 mers | $64^{21-1}$ |
| 22 | +66, | +65, | +64, | 66 mers | $64^{22-1}$ |
| 23 | +69, | +68, | +67, | 69 mers | $64^{23-1}$ |
| 24 | +72, | +71, | +70, | 72 mers | $64^{24-1}$ |
| 25 | +75, | +74, | +73, | 75 mers | $64^{25-1}$ |
| 26 | +78, | +77, | +76, | 78 mers | $64^{26-1}$ |
| 27 | +81, | +80, | +79, | 81 mers | $64^{27-1}$ |
| 28 | +84, | +83, | +82, | 84 mers | $64^{28-1}$ |
| 29 | +87, | +86, | +85, | 87 mers | $64^{29-1}$ |
| 30 | +90, | +89, | +88, | 90 mers | $64^{30-1}$ |
| 31 | +93, | +92, | +91, | 93 mers | $64^{31-1}$ |
| 32 | +96, | +95, | +94, | 96 mers | $64^{32-1}$ |
| 33 | +99, | +98, | +97, | 99 mers | $64^{33-1}$ |
| 34 | +102, | +101, | +100, | 102 mers | $64^{34-1}$ |
| n | +3n, | +(3n − 1), | +(3n − 2) | 3n mers | $64^{n-m}/m = 1$ |

TABLE 15

N-terminal Oriented Peptide Sequence Deducing

| Amino Acid Position Number N-terminal Oriented Peptide | Peptide Length | Number of N-terminal Oriented n-amino acid-length-long Peptides |
|---|---|---|
| 1 | 1 Peptide | $20^{1-1}$ |
| 2 | 2 Peptides | $20^{2-1}$ |
| 3 | 3 Peptides | $20^{3-1}$ |
| 4 | 4 Peptides | $20^{4-1}$ |
| 5 | 5 Peptides | $20^{5-1}$ |
| 6 | 6 Peptides | $20^{6-1}$ |
| 7 | 7 Peptides | $20^{7-1}$ |
| 8 | 8 Peptides | $20^{8-1}$ |
| 9 | 9 Peptides | $20^{9-1}$ |
| 10 | 10 Peptides | $20^{10-1}$ |
| 11 | 11 Peptides | $20^{11-1}$ |
| 12 | 12 Peptides | $20^{12-1}$ |
| 13 | 13 Peptides | $20^{13-1}$ |
| 14 | 14 Peptides | $20^{14-1}$ |
| 15 | 15 Peptides | $20^{15-1}$ |
| 16 | 16 Peptides | $20^{16-1}$ |
| 17 | 17 Peptides | $20^{17-1}$ |
| 18 | 18 Peptides | $20^{18-1}$ |
| 19 | 19 Peptides | $20^{19-1}$ |
| 20 | 20 Peptides | $20^{20-1}$ |
| 21 | 21 Peptides | $20^{21-1}$ |
| 22 | 22 Peptides | $20^{22-1}$ |
| 23 | 23 Peptides | $20^{23-1}$ |
| 24 | 24 Peptides | $20^{24-1}$ |
| 25 | 25 Peptides | $20^{25-1}$ |
| 26 | 26 Peptides | $20^{26-1}$ |
| 27 | 27 Peptides | $20^{27-1}$ |
| 28 | 28 Peptides | $20^{28-1}$ |
| 29 | 29 Peptides | $20^{29-1}$ |
| 30 | 30 Peptides | $20^{30-1}$ |
| 31 | 31 Peptides | $20^{31-1}$ |
| 32 | 32 Peptides | $20^{32-1}$ |
| 33 | 33 Peptides | $20^{33-1}$ |
| 34 | 34 Peptides | $20^{34-1}$ |
| n | n Peptides | $20^{n-m}/m = 1$ |

TABLE 16

C-terminal Oriented Peptide Sequence Deducing

| Amino Acid Position Number C-terminal Oriented Peptide | Peptide Length | Number of C-terminal Oriented n-amino acid-length-long Peptides |
|---|---|---|
| 1 | 1 Peptide | $20^{1}$ |
| 2 | 2 Peptides | $20^{2}$ |
| 3 | 3 Peptides | $20^{3}$ |
| 4 | 4 Peptides | $20^{4}$ |
| 5 | 5 Peptides | $20^{5}$ |
| 6 | 6 Peptides | $20^{6}$ |
| 7 | 7 Peptides | $20^{7}$ |
| 8 | 8 Peptides | $20^{8}$ |
| 9 | 9 Peptides | $20^{9}$ |
| 10 | 10 Peptides | $20^{10}$ |
| 11 | 11 Peptides | $20^{11}$ |
| 12 | 12 Peptides | $20^{12}$ |
| 13 | 13 Peptides | $20^{13}$ |
| 14 | 14 Peptides | $20^{14}$ |
| 15 | 15 Peptides | $20^{15}$ |
| 16 | 16 Peptides | $20^{16}$ |
| 17 | 17 Peptides | $20^{17}$ |
| 18 | 18 Peptides | $20^{18}$ |
| 19 | 19 Peptides | $20^{19}$ |
| 20 | 20 Peptides | $20^{20}$ |

TABLE 16-continued

C-terminal Oriented Peptide Sequence Deducing

| Amino Acid Position Number C-terminal Oriented Peptide | Peptide Length | Number of C-terminal Oriented n-amino acid-length-long Peptides |
|---|---|---|
| 21 | 21 Peptides | $20^{21}$ |
| 22 | 22 Peptides | $20^{22}$ |
| 23 | 23 Peptides | $20^{23}$ |
| 24 | 24 Peptides | $20^{24}$ |
| 25 | 25 Peptides | $20^{25}$ |
| 26 | 26 Peptides | $20^{26}$ |
| 27 | 27 Peptides | $20^{27}$ |
| 28 | 28 Peptides | $20^{28}$ |
| 29 | 29 Peptides | $20^{29}$ |
| 30 | 30 Peptides | $20^{30}$ |
| 31 | 31 Peptides | $20^{31}$ |
| 32 | 32 Peptides | $20^{32}$ |
| 33 | 33 Peptides | $20^{33}$ |
| 34 | 34 Peptides | $20^{34}$ |
| n | n Peptides | $20^n/m$ = zero |

TABLE 17

Comparison of codon-based Oligonucleotide libraries and nucleotide-based Oligonucleotide libraries

| Design based on all Possible Combinations of 61 Codons with One Start Codon at 5'-end or One Stop Codon at 3'-end | | Design based on all Possible Combinations of 4 bases (A. T. G. C.) or (A. U. G. C.) | | Efficiency 4 bases/ 61 codons |
|---|---|---|---|---|
| Length | Total Numbers | Length | Total Numbers | |
| 1 Codon | $61^{(1-1)} = 1$ | 3 mers | $4^{3 \times 1} = 64$ | 64.00 |
| 2 Codons | $61^{(2-1)} = 61$ | 6 mers | $4^{3 \times 2} = 4,096$ | 67.15 |
| 3 Codons | $61^{(3-1)} = 3,721$ | 9 mers | $4^{3 \times 3} = 262,144$ | 70.45 |
| 4 Codons | $61^{(4-1)} = 226,981$ | 12 mers | $4^{3 \times 4} = 16,777,216$ | 73.91 |
| 5 Codons | $61^{(5-1)} = 13,845,841$ | 15 mers | $4^{3 \times 5} = 1,073,741,824$ | 77.55 |
| 6 Codons | $61^{(6-1)} = 844,596,301$ | 18 mers | $4^{3 \times 6} = 68,719,476,736$ | 81.36 |
| 7 Codons | $61^{(7-1)} = 51,520,374,361$ | 21 mers | $4^{3 \times 7} = 4,398,046,511,104$ | 85.37 |
| 8 Codons | $61^{(8-1)} = 3,142,742,836,021$ | 24 mers | $4^{3 \times 8} = 281,474,976,710,656$ | 89.56 |
| 9 Codons | $61^{(9-1)} = 191,707,312,997,281$ | 27 mers | $4^{3 \times 9} = 18,014,398,509,481,984$ | 93.97 |
| 10 Codons | $61^{(10-1)} = 11,694,146,092,834,141$ | 30 mers | $4^{3 \times 10} = 1,152,921,504,606,846,976$ | 98.59 |
| 11 Codons | $61^{(11-1)} = 713,342,911,662,882,601$ | 33 mers | $4^{3 \times 11} = 73,786,976,294,838,206,464$ | 103.44 |
| 12 Codons | $61^{(12-1)} = 43,513,917,611,435,838,661$ | 36 mers | $4^{3 \times 12} = 4,722,366,482,869,645,213,696$ | 108.53 |
| 13 Codons | $61^{(13-1)} = 2,654,348,974,297,586,158,321$ | 39 mers | $4^{3 \times 13} = 302,231,454,903,657,293,676,544$ | 113.86 |
| 14 Codons | $61^{(14-1)} = 161,915,287,432,152,755,657,581$ | 42 mers | $4^{3 \times 14} = 19,342,813,113,834,066,795,298,816$ | 119.46 |
| 15 Codons | $61^{(15-1)} = 9,876,832,533,361,318,095,112,441$ | 45 mers | $4^{3 \times 15} = 1,237,940,039,285,380,274,899,124,224$ | 125.34 |
| 16 Codons | $61^{(16-1)} = 602,486,784,535,040,403,801,858,901$ | 48 mers | $4^{3 \times 16} = 79,228,162,514,264,337,593,543,950,336$ | 131.50 |
| n Codons | $61^{(n-1)} = (4^3 - 3)^{(n-1)}$ | 3n mers | $4^{3n}$ | $4^{3n}/(4^3 - 3)^{(n-1)}$ or $4^{3n}/61^{(n-1)}$ |

TABLE 18

Classification of Oligonucleotide by GC Content

| GC Content | 6 mers (2 codons) | 9 mers (3 codons) | 12 mers (4 codons) | 15 mers (5 codons) | 18 mers (6 codons) | 21 mers (7 codons) | 24 mers (8 codons) |
|---|---|---|---|---|---|---|---|
| 0 | 0% | 0% | 0% | 0% | 0% | 0% | 0% |
| 1 | 16.67% | 11.11% | 8.33% | 6.67% | 5.56% | 4.76% | 4.17% |
| 2 | 33.30% | 22.22% | 16.67% | 13.33% | 11.11% | 9.52% | 8.33% |
| 3 | 50.00% | 33.33% | 25.00% | 20.00% | 16.67% | 14.29% | 12.50% |
| 4 | 66.67% | 44.44% | 33.33% | 26.67% | 22.22% | 19.05% | 16.67% |
| 5 | 83.33% | 55.56% | 41.67% | 33.33% | 27.78% | 23.81% | 20.83% |
| 6 | 100% | 66.67% | 50.00% | 40.00% | 33.33% | 28.57% | 25.00% |
| 7 | | 77.78% | 58.33% | 46.67% | 38.89% | 33.33% | 29.17% |
| 8 | | 88.89% | 66.67% | 53.33% | 44.44% | 38.10% | 33.33% |
| 9 | | 100% | 75.00% | 60.00% | 50.00% | 42.86% | 37.50% |
| 10 | | | 83.33% | 66.67% | 55.56% | 47.62% | 41.67% |
| 11 | | | 91.67% | 73.33% | 61.11% | 52.38% | 45.83% |
| 12 | | | 100% | 80.00% | 66.67% | 57.14% | 50.00% |
| 13 | | | | 86.67% | 72.22% | 61.90% | 54.17% |
| 14 | | | | 93.33% | 77.78% | 66.67% | 58.33% |
| 15 | | | | 100% | 83.33% | 71.43% | 62.50% |
| 16 | | | | | 88.89% | 76.19% | 66.67% |
| 17 | | | | | 94.44% | 80.95% | 70.83% |
| 18 | | | | | 100% | 85.71% | 75.00% |
| 19 | | | | | | 90.48% | 79.17% |

TABLE 18-continued

| | Classification of Oligonucleotide by GC Content | | | | | | |
|---|---|---|---|---|---|---|---|
| GC Content | 6 mers (2 codons) | 9 mers (3 codons) | 12 mers (4 codons) | 15 mers (5 codons) | 18 mers (6 codons) | 21 mers (7 codons) | 24 mers (8 codons) |
| 20 | | | | | | 95.24% | 83.33% |
| 21 | | | | | | 100% | 87.50% |
| 22 | | | | | | | 91.67% |
| 23 | | | | | | | 95.83% |
| 24 | | | | | | | 100% |

The invention claimed is:

1. A method of preparing a cDNA library comprising the following method steps:
   a. preparing an oligonucleotide library comprising all possible combinations of 61 codons that encode the 20 essential amino acids and each oligonucleotide has an orientation sequence wherein the orientation sequence is selected from the group consisting of a 5' end start codon, a 3' end stop codon, a 3' end antisense start codon, a 5' end antisense stop codon, a 5' end two codon restriction endonuclease recognition sequence, a 3' end two codon restriction endonuclease recognition sequence, a 5' end antisense two codon restriction endonuclease recognition sequence, and a 3' end antisense two codon restriction endonuclease recognition sequence and wherein the length of each oligonucleotide is a multiple of three based on the codon length,
   b. mixing an mRNA sample containing a plurality of different mRNA molecules with the oligonucleotide library of method step a wherein the orientation sequence orients each oligonucleotide,
   c. incubating the mixture of method step b with oligo-d(T)s and reagents needed for reverse transcription under conditions suitable for mRNA reverse transcription thereby producing first strands of a cDNA library,
   d. incubating the first strands of a cDNA library of method step c with reagents needed for cDNA synthesis under conditions suitable for cDNA synthesis thereby producing a double stranded cDNA library,
   e. amplifying the double stranded cDNA library of method step d via polymerase chain reaction, and
   f. isolating each cDNA of method step e.

2. The method of claim 1, wherein said oligonucleotides are grouped according to GC content.

3. The method of claim 1, wherein said oligonucleotide library comprises at least 80% of said oligonucleotides.

4. The method of claim 1, wherein each of said cDNA is immobilized to or on a suitable solid support in a set of each of said cDNA at a specific discrete position to form an array, the said set comprising at least two copies of said cDNA, the said array comprising at least two said sets.

* * * * *

UNITED STATES PATENT AND TRADEMARK OFFICE
CERTIFICATE OF CORRECTION

PATENT NO. : 8,697,607 B2
APPLICATION NO. : 10/869055
DATED : April 15, 2014
INVENTOR(S) : Tao Chen et al.

It is certified that error appears in the above-identified patent and that said Letters Patent is hereby corrected as shown below:

Title Page, correct Item (76) Inventors, to read:

-- (76) Inventors: Tao Chen, London (CA); Te-Ming Chen, Bejing (CN); Jianghan Li, legal representative, Bejing (CN) --.

Signed and Sealed this
Third Day of February, 2015

Michelle K. Lee
*Deputy Director of the United States Patent and Trademark Office*

SEQUENCE LISTING

```
<160> NUMBER OF SEQ ID NOS: 31

<210> SEQ ID NO 1
<211> LENGTH: 18
<212> TYPE: DNA
<213> ORGANISM: Artificial
<220> FEATURE:
<223> OTHER INFORMATION: conservative motif of six amino acids of a zinc
      finger gene family

<400> SEQUENCE: 1
cacacaggag aaaagcca                                                 18

<210> SEQ ID NO 2
<211> LENGTH: 6
<212> TYPE: PRT
<213> ORGANISM: Artificial
<220> FEATURE:
<223> OTHER INFORMATION: conservative motif of six amino acids of zinc
      finger gene family

<400> SEQUENCE: 2

His Thr Gly Glu Phe Pro
1               5

<210> SEQ ID NO 3
<211> LENGTH: 12
<212> TYPE: DNA
<213> ORGANISM: Artificial
<220> FEATURE:
<223> OTHER INFORMATION: forward pcr primer

<400> SEQUENCE: 3
atggcagcat cg                                                       12

<210> SEQ ID NO 4
<211> LENGTH: 12
<212> TYPE: DNA
<213> ORGANISM: Artificial
<220> FEATURE:
<223> OTHER INFORMATION: sample primer
<220> FEATURE:
<221> NAME/KEY: misc_feature
<222> LOCATION: (10)..(12)
<223> OTHER INFORMATION: 5'-nitroindole
<220> FEATURE:
<221> NAME/KEY: misc_feature
<222> LOCATION: (10)..(12)
<223> OTHER INFORMATION: 5'-nitroindole-2'-deoxyriboside

<400> SEQUENCE: 4
atggcagcan nn                                                       12
```

```
<210> SEQ ID NO 5
<211> LENGTH: 15
<212> TYPE: DNA
<213> ORGANISM: Artificial
<220> FEATURE:
<223> OTHER INFORMATION: sample primer
<220> FEATURE:
<221> NAME/KEY: misc_feature
<222> LOCATION: (10)..(12)
<223> OTHER INFORMATION: 5'-nitroindole
<220> FEATURE:
<221> NAME/KEY: misc_feature
<222> LOCATION: (10)..(12)
<223> OTHER INFORMATION: 5'-nitroindole-2'-deoxyriboside

<400> SEQUENCE: 5
atggcagcan nngca                                                     15

<210> SEQ ID NO 6
<211> LENGTH: 6
<212> TYPE: PRT
<213> ORGANISM: Artificial
<220> FEATURE:
<223> OTHER INFORMATION: exemplary antigenic epitope

<400> SEQUENCE: 6

Glu Phe Cys Met His Trp
1               5

<210> SEQ ID NO 7
<211> LENGTH: 18
<212> TYPE: DNA
<213> ORGANISM: Artificial
<220> FEATURE:
<223> OTHER INFORMATION: exemplary primer

<400> SEQUENCE: 7
gaattctgca tgcactgg                                                  18

<210> SEQ ID NO 8
<211> LENGTH: 18
<212> TYPE: DNA
<213> ORGANISM: Artificial
<220> FEATURE:
<223> OTHER INFORMATION: exemplary primer

<400> SEQUENCE: 8
gaattttgca tgcactgg                                                  18

<210> SEQ ID NO 9
<211> LENGTH: 18
<212> TYPE: DNA
<213> ORGANISM: Artificial
<220> FEATURE:
<223> OTHER INFORMATION: exemplary primer

<400> SEQUENCE: 9
gaattctgta tgcactgg                                                  18

<210> SEQ ID NO 10
<211> LENGTH: 18
<212> TYPE: DNA
<213> ORGANISM: Artificial
<220> FEATURE:
<223> OTHER INFORMATION: exemplary primer

<400> SEQUENCE: 10
gaattctgta tgcattgg                                                  18
```

```
<210> SEQ ID NO 11
<211> LENGTH: 18
<212> TYPE: DNA
<213> ORGANISM: Artificial
<220> FEATURE:
<223> OTHER INFORMATION: exemplary primer

<400> SEQUENCE: 11
gagttctgca tgcactgg                                                 18

<210> SEQ ID NO 12
<211> LENGTH: 18
<212> TYPE: DNA
<213> ORGANISM: Artificial
<220> FEATURE:
<223> OTHER INFORMATION: exemplary primer

<400> SEQUENCE: 12
gagttttgca tgcactgg                                                 18

<210> SEQ ID NO 13
<211> LENGTH: 18
<212> TYPE: DNA
<213> ORGANISM: Artificial
<220> FEATURE:
<223> OTHER INFORMATION: exemplary primer

<400> SEQUENCE: 13
gagttctgta tgcactgg                                                 18

<210> SEQ ID NO 14
<211> LENGTH: 18
<212> TYPE: DNA
<213> ORGANISM: Artificial
<220> FEATURE:
<223> OTHER INFORMATION: exemplary primer

<400> SEQUENCE: 14
gagttctgta tgcattgg                                                 18

<210> SEQ ID NO 15
<211> LENGTH: 18
<212> TYPE: DNA
<213> ORGANISM: Artificial
<220> FEATURE:
<223> OTHER INFORMATION: exemplary primer

<400> SEQUENCE: 15
gaattctgca tgcattgg                                                 18

<210> SEQ ID NO 16
<211> LENGTH: 18
<212> TYPE: DNA
<213> ORGANISM: Artificial
<220> FEATURE:
<223> OTHER INFORMATION: exemplary primer

<400> SEQUENCE: 16
gaattttgca tgcattgg                                                 18

<210> SEQ ID NO 17
<211> LENGTH: 18
<212> TYPE: DNA
<213> ORGANISM: Artificial
<220> FEATURE:
<223> OTHER INFORMATION: exemplary primer
```

```
<400> SEQUENCE: 17
gaattctgta tgcattgg                                                    18

<210> SEQ ID NO 18
<211> LENGTH: 18
<212> TYPE: DNA
<213> ORGANISM: Artificial
<220> FEATURE:
<223> OTHER INFORMATION: exemplary primer

<400> SEQUENCE: 18
gaattctgta tgcactgg                                                    18

<210> SEQ ID NO 19
<211> LENGTH: 18
<212> TYPE: DNA
<213> ORGANISM: Artificial
<220> FEATURE:
<223> OTHER INFORMATION: exemplary primer

<400> SEQUENCE: 19
gagttctgca tgcattgg                                                    18

<210> SEQ ID NO 20
<211> LENGTH: 18
<212> TYPE: DNA
<213> ORGANISM: Artificial
<220> FEATURE:
<223> OTHER INFORMATION: exemplary primer

<400> SEQUENCE: 20
gagttttgca tgcattgg                                                    18

<210> SEQ ID NO 21
<211> LENGTH: 18
<212> TYPE: DNA
<213> ORGANISM: Artificial
<220> FEATURE:
<223> OTHER INFORMATION: exemplary primer

<400> SEQUENCE: 21
gagttctgta tgcattgg                                                    18

<210> SEQ ID NO 22
<211> LENGTH: 18
<212> TYPE: DNA
<213> ORGANISM: Artificial
<220> FEATURE:
<223> OTHER INFORMATION: exemplary primer

<400> SEQUENCE: 22
gagttctgta tgcactgg                                                    18

<210> SEQ ID NO 23
<211> LENGTH: 18
<212> TYPE: DNA
<213> ORGANISM: Artificial
<220> FEATURE:
<223> OTHER INFORMATION: consolidated primer
<220> FEATURE:
<221> NAME/KEY: misc_feature
<222> LOCATION: (3)..(3)
<223> OTHER INFORMATION: universal base analogue
<220> FEATURE:
<221> NAME/KEY: misc_feature
<222> LOCATION: (6)..(6)
<223> OTHER INFORMATION: universal base analogue
<220> FEATURE:
```

```
<221> NAME/KEY: misc_feature
<222> LOCATION: (9)..(9)
<223> OTHER INFORMATION: universal base analogue
<220> FEATURE:
<221> NAME/KEY: misc_feature
<222> LOCATION: (15)..(15)
<223> OTHER INFORMATION: universal base analogue such as
      5'-nitroindole-2'-deoxyriboside, 3'-nitropyrrole, inosine,
      pypoxanthine, etc.

<400> SEQUENCE: 23
ganttntgna tgcantgg                                                      18

<210> SEQ ID NO 24
<211> LENGTH: 24
<212> TYPE: DNA
<213> ORGANISM: Artificial
<220> FEATURE:
<223> OTHER INFORMATION: beta-actin forward primer

<400> SEQUENCE: 24
atggtgggaa tgggtcagaa ggac                                               24

<210> SEQ ID NO 25
<211> LENGTH: 21
<212> TYPE: DNA
<213> ORGANISM: Artificial
<220> FEATURE:
<223> OTHER INFORMATION: beta-actin backward primer

<400> SEQUENCE: 25
ggtcatcttt tcacggttgg c                                                  21

<210> SEQ ID NO 26
<211> LENGTH: 20
<212> TYPE: DNA
<213> ORGANISM: Artificial
<220> FEATURE:
<223> OTHER INFORMATION: beta-actin forward primer

<400> SEQUENCE: 26
tgagagggaa atcgtgcgtg                                                    20

<210> SEQ ID NO 27
<211> LENGTH: 24
<212> TYPE: DNA
<213> ORGANISM: Artificial
<220> FEATURE:
<223> OTHER INFORMATION: beta-actin backward primer

<400> SEQUENCE: 27
atctgctgga aggtggacag tgag                                               24

<210> SEQ ID NO 28
<211> LENGTH: 22
<212> TYPE: DNA
<213> ORGANISM: artificial
<220> FEATURE:
<223> OTHER INFORMATION: gapd forward primer

<400> SEQUENCE: 28
aaggtgaagg tcggagtcaa cg                                                 22

<210> SEQ ID NO 29
<211> LENGTH: 22
<212> TYPE: DNA
<213> ORGANISM: artificial
<220> FEATURE:
```

```
<223> OTHER INFORMATION: gapd backward primer

<400> SEQUENCE: 29
tggaagatgg tgatgggatt tc                                              22

<210> SEQ ID NO 30
<211> LENGTH: 24
<212> TYPE: DNA
<213> ORGANISM: artificial
<220> FEATURE:
<223> OTHER INFORMATION: gapd forward primer

<400> SEQUENCE: 30
tgccatcact gccacccaga agac                                            24

<210> SEQ ID NO 31
<211> LENGTH: 24
<212> TYPE: DNA
<213> ORGANISM: artificial
<220> FEATURE:
<223> OTHER INFORMATION: gapd backward primer

<400> SEQUENCE: 31
atgaggtcca ccaccctgtt gctg                                            24
```